US010538782B2

(12) United States Patent
Schachtschabel et al.

(10) Patent No.: US 10,538,782 B2
(45) Date of Patent: Jan. 21, 2020

(54) PLANTS HAVING INCREASED TOLERANCE TO HERBICIDES

(71) Applicant: BASF SE, Ludwigshafen (DE)

(72) Inventors: Doreen Schachtschabel, Mannheim (DE); Birgit Steinhardt, Hassloch (DE); Mihiret Tekeste Sisay, Mannheim (DE); Stefan Tresch, Neustadt Hambach (DE); Julia Major, Freinsheim (DE); Florian Vogt, Mannheim (DE); Frederick Calo, Dusseldorf (DE); Jens Lerchl, Potsdam OT Golm (DE)

(73) Assignee: BASF SE, Ludwigshafen (DE)

( * ) Notice: Subject to any disclaimer, the term of this patent is extended or adjusted under 35 U.S.C. 154(b) by 50 days.

(21) Appl. No.: 15/545,161

(22) PCT Filed: Jan. 20, 2016

(86) PCT No.: PCT/IB2016/050268
§ 371 (c)(1),
(2) Date: Jul. 20, 2017

(87) PCT Pub. No.: WO2016/116870
PCT Pub. Date: Jul. 28, 2016

(65) Prior Publication Data
US 2018/0179550 A1 Jun. 28, 2018

(30) Foreign Application Priority Data
Jan. 21, 2015 (EP) .................................. 15151966

(51) Int. Cl.
*C12N 15/82* (2006.01)
*C12N 9/78* (2006.01)

(52) U.S. Cl.
CPC ........... *C12N 15/8274* (2013.01); *C12N 9/78* (2013.01); *C12N 2820/55* (2013.01); *C12N 2840/007* (2013.01); *C12N 2840/65* (2013.01)

(58) Field of Classification Search
None
See application file for complete search history.

(56) References Cited

U.S. PATENT DOCUMENTS

| 6,369,299 | B1 | 4/2002 | Sadowsky et al. |
| 9,822,082 | B2 | 11/2017 | Major et al. |
| 9,822,105 | B2 | 11/2017 | Major et al. |
| 2016/0159770 | A1 | 6/2016 | Major et al. |
| 2017/0022170 | A1 | 1/2017 | Major et al. |
| 2017/0029383 | A1 | 2/2017 | Major et al. |
| 2017/0101383 | A1 | 4/2017 | Major et al. |
| 2017/0144985 | A1 | 5/2017 | Major et al. |

FOREIGN PATENT DOCUMENTS

| CN | 1546673 A | 11/2004 |
| CN | 102954959 A | 3/2013 |
| WO | WO-01/64912 A2 | 9/2001 |
| WO | WO-2009/076711 A1 | 6/2009 |
| WO | WO-2010/025499 A1 | 3/2010 |
| WO | WO-2014/107660 A2 | 7/2014 |
| WO | WO-2015/007711 A1 | 1/2015 |
| WO | WO-2015/144881 A1 | 10/2015 |
| WO | WO-2015/150541 A1 | 10/2015 |
| WO | WO-2015/155129 A1 | 10/2015 |
| WO | WO-2015/155271 A1 | 10/2015 |
| WO | WO-2015/155272 A1 | 10/2015 |
| WO | WO-2015/155273 A1 | 10/2015 |
| WO | WO-2015/162169 A1 | 10/2015 |
| WO | WO-2016/116870 A1 | 7/2016 |

OTHER PUBLICATIONS

European patent application No. 16739858.5, Extended European Search Report, dated May 11, 2018.
Seffernick et al., Melamine deaminase and atrazine chlorohydrolase: 98 percent identical but functionally different, J. Bacteriol., 183(8):2405-10 (2001).
De Souza et al., Atrazine chlorohydrolase from *Pseudomonas* sp. strain ADP: gene sequence, enzyme purification, and protein characterization, J. Bacteriol., 178(16):4894-900 (1996).
Genbank Accession No. WP_019372648.1, hypothetical protein [*Alicycliphilus* sp. CRZ1], (Jun. 29, 2013).
Gen Bank Accession No. WP_052862785.1, hypothetical protein [*Delftia lacustris*] (Aug. 20, 2015).
International Application No. PCT/IB2016/050268, International Preliminary Report on Patentability, dated Jul. 25, 2017.
International Application No. PCT/IB2016/050268, International Search Report, dated Jun. 6, 2016.
Seffernick et al., Atrazine chlorohydrolase from *Pseudomonas* sp. strain ADP is a metalloenzyme, Biochemistry, 41(48):14430-7 (2002).
Wackett et al., Biodegradation of atrazine and related s-triazine compounds: from enzymes to field studies, Appl. Microbiol. Biotechnol., 58(1):39-45 (2002).
Zhang et al., Recent advances in cellulose biosynthesis inhibiting (CBI) herbicides, World Pesticides, 35(2): 12 pp. (2013).
U.S. Appl. No. 15/545,161, filed Jul. 20, 2017, "Plants Having Increased Tolerance to Herbicides".

*Primary Examiner* — Eileen B O Hara
(74) *Attorney, Agent, or Firm* — Marshall, Gerstein & Borun LLP

(57) ABSTRACT

The present invention provides a plant or plant part comprising a polynucleotide encoding a wildtype or mutant TriA polypeptide, the expression of said polynucleotide confers to the plant or plant part tolerance to herbicides.

30 Claims, 5 Drawing Sheets
Specification includes a Sequence Listing.

SEQUENCE LISTING

```
<160> NUMBER OF SEQ ID NOS: 32

<210> SEQ ID NO 1
<211> LENGTH: 1425
<212> TYPE: DNA
<213> ORGANISM: Artificial Sequence
<220> FEATURE:
<223> OTHER INFORMATION: Pseudomonas

<400> SEQUENCE: 1
atgcagaccc tgagcattca gcatggcacc ctggttacaa tggatcagta tcgtcgtgtt      60
ctgggtgata gctgggttca tgttcaggat ggtcgtattg ttgcactggg tgttcatgca     120
gaaagcgttc cgcctccggc agatcgtgtt attgatgcac gtggtaaagt tgttctgcct     180
ggttttatca atgcacatac ccatgttaat cagattctgc tgcgtggtgg tccgagtcat     240
ggtcgtcagc tgtatgattg gctgtttaat gttctgtatc cgggtcagaa agcaatgcgt     300
ccggaagatg ttgcagttgc agttcgtctg tattgtgcag aagcagttcg tagcggtatt     360
accaccatta atgataatgc agatagcgcc atttatccgg gtaatattga agcagcaatg     420
gccgtttatg gtgaagttgg tgttcgtgtt gtttatgccc gtatgttttt tgatcgtatg     480
gatggtcgca ttcagggtta tgttgatgca ctgaaagcac gtagtccgca ggttgaactg     540
tgtagcatta tggaagaaac cgcagttgca aaagatcgta ttaccgcact gagcgatcaa     600
tatcatggta cagcaggcgg tcgtattagc gtttggcctg caccggcaat tacaccggca     660
gttaccgttg aaggtatgcg ttgggcacag gcatttgcac gtgatcgtgc agttatgtgg     720
accctgcata tggccgaaag cgatcatgat gaacgtctgc attggatgag tccggcagaa     780
tatatggaat gttatggtct gctggatgag cgcctgcagg ttgcacattg tgtttatttt     840
gatcgcaaag atgttcgtct gctgcatcgt cataatgtta aagttgcaag ccaggttgtt     900
agcaatgcat atctgggtag cggtgttgca ccggttccgg aaatggttga acgtggtatg     960
gcagttggta ttggcaccga tgatggtaat tgtaatgata gcgtgaacat gatcggcgat    1020
atgaaattta tggcccatat tcatcgtgcc gttcatcgtg atgcagatgt tctgacaccg    1080
gaaaaaattc tggaaatggc aaccattgat ggtgcacgta gcctgggtat ggatcatgaa    1140
attggtagca ttgaaaccgg taaacgtgca gatctgatcc tgctggatct gcgtcatccg    1200
cagacaacac cgcatcatca tctggcagcc accattgttt tcaggcata tggtaatgaa    1260 gttgacaccg ttctgattga tggcaatgtt gttatggaaa atcgtcgtct gagctttctg    1320
```

```
cctccggaac gtgaactggc atttctggaa gaagcacaga gtcgcgcaac cgcaattctg    1380
cagcgtgcaa atatggttgc aaatccggca tggcgtagcc tgtga                    1425
```

<210> SEQ ID NO 2
<211> LENGTH: 474
<212> TYPE: PRT
<213> ORGANISM: Artificial Sequence
<220> FEATURE:
<223> OTHER INFORMATION: Pseudomonas

<400> SEQUENCE: 2

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Arg Leu Tyr Cys
            100                 105                 110

Ala Glu Ala Val Arg Ser Gly Ile Thr Thr Ile Asn Asp Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Ile Thr Pro Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                325                 330                 335

Met Ile Gly Asp Met Lys Phe Met Ala His Ile His Arg Ala Val His
```

```
                    340                 345                 350
Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470
```

<210> SEQ ID NO 3
<211> LENGTH: 473
<212> TYPE: PRT
<213> ORGANISM: Artificial Sequence
<220> FEATURE:
<223> OTHER INFORMATION: Pseudomonas
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid

<400> SEQUENCE: 3

```
Met Gln Thr Leu Ser Ile Gln His Gly Thr Leu Val Thr Met Asp Xaa
1               5                   10                  15
```

-continued

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Ala Xaa
        35                  40                  45

Arg Val Ile Asp Ala Arg Gly Lys Val Val Leu Pro Gly Phe Ile Xaa
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Xaa
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Xaa
        115                 120                 125

Ser Ala Ile Tyr Pro Gly Asn Ile Glu Ala Ala Met Ala Val Tyr Xaa
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Xaa
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Xaa
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Ala Xaa
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Leu
385                 390                 395                 400

Arg Arg Leu Ser His His Leu Ala Ala Thr Ile Val Phe Gln Ala Tyr
                405                 410                 415

Gly Asn Glu Val Asp Thr Val Leu Ile Asp Gly Asn Val Val Met Xaa
            420                 425                 430

Asn Arg Arg Leu Ser Phe Leu Pro Pro Glu Arg Glu Leu Ala Phe Leu

```
                435                 440                 445
Glu Glu Ala Gln Ser Arg Ala Thr Ala Ile Leu Gln Arg Ala Asn Met
450                 455                 460

Val Ala Asn Pro Ala Trp Arg Ser Leu
465                 470

<210> SEQ ID NO 4
<211> LENGTH: 473
<212> TYPE: PRT
<213> ORGANISM: Artificial Sequence
<220> FEATURE:
<223> OTHER INFORMATION: Pseudomonas

<400> SEQUENCE: 4

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

Arg Val Ile Asp Ala Arg Gly Lys Val Val Leu Pro Gly Phe Ile Asn
        50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Ser Asn Ala Tyr
290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Ala Asn
```

```
                325                 330                 335
Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
            370                 375                 380

Glu Thr Gly Lys Arg Ala Asp Leu Ile Leu Asp Leu Arg His Leu
385                 390                 395                 400

Arg Arg Leu Ser His His Leu Ala Ala Thr Ile Val Phe Gln Ala Tyr
                405                 410                 415

Gly Asn Glu Val Asp Thr Val Leu Ile Asp Gly Asn Val Val Met Glu
            420                 425                 430

Asn Arg Arg Leu Ser Phe Leu Pro Pro Glu Arg Glu Leu Ala Phe Leu
            435                 440                 445

Glu Glu Ala Gln Ser Arg Ala Thr Ala Ile Leu Gln Arg Ala Asn Met
450                 455                 460

Val Ala Asn Pro Ala Trp Arg Ser Leu
465                 470

<210> SEQ ID NO 5
<211> LENGTH: 601
<212> TYPE: PRT
<213> ORGANISM: Artificial Sequence
<220> FEATURE:
<223> OTHER INFORMATION: Pseudomonas

<400> SEQUENCE: 5

Ala Ser Met Val Thr Leu Thr Pro Leu Phe Ser Phe Ser Leu Leu Asn
1               5                  10                  15

Cys Thr Arg Lys Ala Ser Arg Ser Val Met Ser Ala Ser Ser Trp Leu
                20                  25                  30

Val Thr Cys Gly Met Thr Thr Gln Leu Arg Cys Arg Phe Phe Asp Gly
            35                  40                  45

Ile Ile Ser Ala Leu Arg Arg Val Thr His Tyr Trp Arg His Ile Met
50                  55                  60

Gln Thr Leu Ser Ile Gln His Gly Thr Leu Val Thr Met Asp Gln Tyr
65                  70                  75                  80

Arg Arg Val Leu Gly Asp Ser Trp Val His Val Gln Asp Gly Arg Ile
                85                  90                  95

Val Ala Leu Gly Val His Ala Glu Ser Val Pro Pro Ala Asp Arg
            100                 105                 110

Val Ile Asp Ala Arg Gly Lys Val Leu Pro Gly Phe Ile Asn Ala
            115                 120                 125

His Thr His Val Asn Gln Ile Leu Leu Arg Gly Gly Pro Ser His Gly
            130                 135                 140

Arg Gln Phe Tyr Asp Trp Leu Phe Asn Val Val Tyr Pro Gly Gln Lys
145                 150                 155                 160

Ala Met Arg Pro Glu Asp Val Ala Val Ala Val Arg Leu Tyr Cys Ala
                165                 170                 175

Glu Ala Val Arg Ser Gly Ile Thr Thr Ile Asn Glu Asn Ala Asp Ser
            180                 185                 190

Ala Ile Tyr Pro Gly Asn Ile Glu Ala Ala Met Ala Val Tyr Gly Glu
            195                 200                 205

Val Gly Val Arg Val Val Tyr Ala Arg Met Phe Phe Asp Arg Met Asp
```

```
            210                 215                 220
Gly Arg Ile Gln Gly Tyr Val Asp Ala Leu Lys Ala Arg Ser Pro Gln
225                 230                 235                 240

Val Glu Leu Cys Ser Ile Met Glu Gly Thr Ala Val Ala Lys Asp Arg
                245                 250                 255

Ile Thr Ala Leu Ser Asp Gln Tyr His Gly Thr Ala Gly Arg Ile
                260                 265                 270

Ser Val Trp Pro Ala Pro Ala Thr Thr Thr Ala Val Thr Val Glu Gly
                275                 280                 285

Met Arg Trp Ala Gln Ala Phe Ala Arg Asp Arg Ala Val Met Trp Thr
                290                 295                 300

Leu His Met Ala Glu Ser Asp His Asp Glu Arg Ile His Gly Met Ser
305                 310                 315                 320

Pro Ala Glu Tyr Met Glu Cys Tyr Gly Leu Leu Asp Glu Arg Leu Gln
                325                 330                 335

Val Ala His Cys Val Tyr Phe Asp Arg Lys Asp Val Arg Leu Leu His
                340                 345                 350

Arg His Asn Val Lys Val Ala Ser Gln Val Val Ser Asn Ala Tyr Leu
                355                 360                 365

Gly Ser Gly Val Ala Pro Val Pro Glu Met Val Glu Arg Gly Met Ala
                370                 375                 380

Val Gly Ile Gly Thr Asp Asn Gly Asn Ser Asn Asp Ser Val Asn Met
385                 390                 395                 400

Ile Gly Asp Met Lys Phe Met Ala His Ile His Arg Ala Val His Arg
                405                 410                 415

Asp Ala Asp Val Leu Thr Pro Glu Lys Ile Leu Glu Met Ala Thr Ile
                420                 425                 430

Asp Gly Ala Arg Ser Leu Gly Met Asp His Glu Ile Gly Ser Ile Glu
                435                 440                 445

Thr Gly Lys Arg Ala Asp Leu Ile Leu Leu Asp Leu Arg His Pro Gln
                450                 455                 460

Thr Thr Pro His His His Leu Ala Ala Thr Ile Val Phe Gln Ala Tyr
465                 470                 475                 480

Gly Asn Glu Val Asp Thr Val Leu Ile Asp Gly Asn Val Val Met Glu
                485                 490                 495

Asn Arg Arg Leu Ser Phe Leu Pro Pro Glu Arg Glu Leu Ala Phe Leu
                500                 505                 510

Glu Glu Ala Gln Ser Arg Ala Thr Ala Ile Leu Gln Arg Ala Asn Met
                515                 520                 525

Val Ala Asn Pro Ala Trp Arg Ser Leu Glu Met Thr Pro Leu Leu His
530                 535                 540

Pro Pro Pro Leu Glu Glu Ile Ala Ala Ile Leu Ala Arg Leu Gly Leu
545                 550                 555                 560

Gly Gly Gly His Asp Leu Asp Gly Tyr Arg Ile Ala Met Asn Ala Ala
                565                 570                 575

Leu Pro Ser Phe Ala Arg Val Glu Ser Leu Val Gly Glu Gly Arg Leu
                580                 585                 590

Arg Ala Pro Ala Ser Arg Arg Ser Glu
                595                 600

<210> SEQ ID NO 6
<211> LENGTH: 614
<212> TYPE: PRT
<213> ORGANISM: Artificial Sequence
```

```
<220> FEATURE:
<223> OTHER INFORMATION: Pseudomonas

<400> SEQUENCE: 6

Ser Ala Ala Thr Ala Ala Leu Ile Met Lys Ala Ser Met Val Thr Leu
1               5                   10                  15

Thr Pro Leu Phe Ser Phe Ser Leu Leu Asn Cys Thr Arg Lys Ala Ser
            20                  25                  30

Arg Ser Val Met Ser Ala Ser Ser Trp Leu Val Thr Cys Gly Met Thr
        35                  40                  45

Thr Gln Leu Arg Cys Arg Phe Phe Asp Gly Val Ile Ser Ala Leu Arg
50                  55                  60

Arg Val Thr His Tyr Trp Arg His Ile Met Gln Thr Leu Ser Ile Gln
65                  70                  75                  80

His Gly Thr Leu Val Thr Met Asp Gln Tyr Arg Arg Val Leu Gly Asp
                85                  90                  95

Ser Trp Val His Val Gln Asp Gly Arg Ile Val Ala Leu Gly Val His
            100                 105                 110

Ala Glu Ser Val Pro Pro Ala Asp Arg Val Ile Asp Ala Arg Gly
        115                 120                 125

Lys Val Val Leu Pro Gly Phe Ile Asn Ala His Thr His Val Asn Gln
130                 135                 140

Ile Leu Leu Arg Gly Gly Pro Ser His Gly Arg Gln Phe Tyr Asp Trp
145                 150                 155                 160

Leu Phe Asn Val Val Tyr Pro Gly Gln Lys Ala Met Arg Pro Glu Asp
            165                 170                 175

Val Ala Val Ala Val Arg Leu Tyr Cys Ala Glu Ala Val Arg Ser Gly
        180                 185                 190

Ile Thr Thr Ile Asn Glu Asn Ala Asp Ser Ala Ile Tyr Pro Gly Asn
            195                 200                 205

Ile Glu Ala Ala Met Ala Val Tyr Gly Glu Val Gly Val Arg Val Val
        210                 215                 220

Tyr Ala Arg Met Phe Phe Asp Arg Met Asp Gly Arg Ile Gln Gly Tyr
225                 230                 235                 240

Val Asp Ala Leu Lys Ala Arg Ser Pro Gln Val Glu Leu Cys Ser Ile
            245                 250                 255

Met Glu Glu Thr Ala Val Ala Lys Asp Arg Ile Thr Ala Leu Ser Asp
        260                 265                 270

Gln Tyr His Gly Thr Ala Gly Gly Arg Ile Ser Val Trp Pro Ala Pro
            275                 280                 285

Ala Thr Thr Thr Ala Val Thr Val Glu Gly Met Arg Trp Ala Gln Ala
290                 295                 300

Phe Ala Arg Asp Arg Ala Val Met Trp Thr Leu His Met Ala Glu Ser
305                 310                 315                 320

Asp His Asp Glu Arg Ile His Gly Met Ser Pro Ala Asp Tyr Met Glu
            325                 330                 335

Cys Tyr Gly Leu Leu Asp Glu Arg Leu Gln Val Ala His Cys Val Tyr
        340                 345                 350

Phe Asp Arg Lys Asp Val Arg Leu Leu His Arg His Asn Val Lys Val
            355                 360                 365

Ala Ser Gln Val Val Ser Asn Ala Tyr Leu Gly Ser Gly Val Ala Pro
370                 375                 380

Val Pro Glu Met Val Glu Arg Gly Met Ala Val Gly Ile Gly Thr Asp
385                 390                 395                 400
```

```
Asn Gly Asn Ser Asn Asp Ser Val Asn Met Ile Gly Asp Met Lys Phe
            405                 410                 415

Met Ala His Ile His Arg Ala Val His Arg Asp Ala Asp Val Leu Thr
            420                 425                 430

Pro Glu Lys Ile Leu Glu Met Ala Thr Ile Asp Gly Ala Arg Ser Leu
            435                 440                 445

Gly Met Asp His Glu Ile Gly Ser Ile Glu Thr Gly Lys Arg Ala Asp
            450                 455                 460

Leu Ile Leu Leu Asp Leu Arg His Pro Gln Thr Thr Pro His His His
465                 470                 475                 480

Leu Ala Ala Thr Ile Val Phe Gln Ala Tyr Gly Asn Glu Val Asp Thr
            485                 490                 495

Val Leu Ile Asp Gly Asn Val Val Met Glu Asn Arg Arg Leu Ser Phe
            500                 505                 510

Leu Pro Pro Glu Arg Glu Leu Ala Phe Leu Glu Glu Ala Gln Ser Arg
            515                 520                 525

Ala Thr Ala Ile Leu Gln Arg Ala Asn Met Val Ala Asn Pro Ala Trp
            530                 535                 540

Arg Ser Leu Glu Met Thr Pro Leu Leu His Pro Pro Leu Glu Glu
545                 550                 555                 560

Ile Ala Ala Ile Leu Ala Arg Leu Gly Leu Gly Gly His Asp Leu
            565                 570                 575

Asp Gly Tyr Arg Ile Ala Met Asn Ala Ala Leu Pro Ser Phe Ala Arg
            580                 585                 590

Val Glu Ser Leu Val Gly Glu Gly Arg Leu Arg Ala Pro Ala Ser Arg
            595                 600                 605

Arg Ser Glu Arg Pro Glu
            610

<210> SEQ ID NO 7
<211> LENGTH: 144
<212> TYPE: PRT
<213> ORGANISM: Artificial Sequence
<220> FEATURE:
<223> OTHER INFORMATION: Pseudomonas

<400> SEQUENCE: 7

Pro His Gly Arg Gln Phe Tyr Asp Trp Leu Phe Asn Val Leu Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Ala Leu Lys Ala Arg
            85                  90                  95

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
            115                 120                 125

Gly Arg Ile Ser Val Trp Pro Ala Pro Ala Thr Thr Thr Ala Val Thr
            130                 135                 140
```

<210> SEQ ID NO 8
<211> LENGTH: 144
<212> TYPE: PRT
<213> ORGANISM: Artificial Sequence
<220> FEATURE:
<223> OTHER INFORMATION: Pseudomonas

<400> SEQUENCE: 8

Ser His Gly Arg Gln Phe Tyr Asp Trp Leu Phe Asn Val Leu Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Thr Leu Lys Ala Arg
                85                  90                  95

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
        115                 120                 125

Gly Arg Ile Ser Val Trp Pro Ala Pro Ala Thr Thr Thr Ala Val Thr
    130                 135                 140

<210> SEQ ID NO 9
<211> LENGTH: 144
<212> TYPE: PRT
<213> ORGANISM: Artificial Sequence
<220> FEATURE:
<223> OTHER INFORMATION: Pseudomonas

<400> SEQUENCE: 9

Pro His Gly Arg Gln Phe Tyr Asp Trp Leu Phe Asn Val Val Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Ala Leu Lys Ala Arg
                85                  90                  95

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
        115                 120                 125

Gly Arg Ile Ser Val Trp Pro Ala Pro Ala Thr Thr Thr Ala Val Thr
    130                 135                 140

<210> SEQ ID NO 10
<211> LENGTH: 145
<212> TYPE: PRT

<213> ORGANISM: Artificial Sequence
<220> FEATURE:
<223> OTHER INFORMATION: Pseudomonas

<400> SEQUENCE: 10

Ser His Gly Arg Gln Phe Tyr Asp Trp Leu Phe Asn Val Leu Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Asn Ala Asp Ser Ala Ile Tyr Pro Gly Asn Ile Glu Ala Ala Met Ala
    50                  55                  60

Val Tyr Gly Glu Val Gly Val Arg Val Val Tyr Ala Arg Met Phe Phe
65                  70                  75                  80

Asp Arg Met Asp Gly Arg Ile Gln Gly Tyr Val Asp Thr Leu Lys Ala
                85                  90                  95

Arg Ser Pro Gln Val Glu Leu Cys Ser Ile Met Glu Glu Thr Ala Val
            100                 105                 110

Ala Lys Asp Arg Ile Thr Ala Leu Ser Asp Gln Tyr His Gly Thr Ala
        115                 120                 125

Gly Gly Arg Ile Ser Val Trp Pro Ala Pro Thr Thr Thr Ala Val
    130                 135                 140

Thr
145

<210> SEQ ID NO 11
<211> LENGTH: 144
<212> TYPE: PRT
<213> ORGANISM: Artificial Sequence
<220> FEATURE:
<223> OTHER INFORMATION: Pseudomonas

<400> SEQUENCE: 11

Ser His Gly Arg Gln Phe Tyr Asp Trp Leu Phe Asn Val Val Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Ala Leu Lys Ala Arg
                85                  90                  95

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
        115                 120                 125

Gly Arg Ile Ser Val Trp Pro Ala Pro Ala Thr Thr Thr Ala Val Thr
    130                 135                 140

<210> SEQ ID NO 12
<211> LENGTH: 496
<212> TYPE: PRT
<213> ORGANISM: Artificial Sequence
<220> FEATURE:

<223> OTHER INFORMATION: Pseudomonas

<400> SEQUENCE: 12

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Lys Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Gly Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400
```

```
Gln Thr Thr Pro His His His Leu Ala Ala Thr Ile Val Phe Gln Ala
                405                 410                 415
Tyr Gly Asn Glu Val Asp Thr Val Leu Ile Asp Gly Asn Val Val Met
            420                 425                 430
Glu Asn Arg Cys Leu Ser Phe Leu Pro Pro Glu Arg Glu Leu Ala Phe
        435                 440                 445
Leu Glu Gly Ala Gln Ser Arg Ala Thr Ala Ile Leu Gln Arg Ala Asn
    450                 455                 460
Met Val Ala Asn Pro Ala Trp Arg Ser Leu Glu Met Thr Pro Leu Leu
465                 470                 475                 480
His Pro Pro Pro Leu Glu Glu Ile Ala Ala Ile Leu Ala Arg Leu Gly
                485                 490                 495

<210> SEQ ID NO 13
<211> LENGTH: 496
<212> TYPE: PRT
<213> ORGANISM: Artificial Sequence
<220> FEATURE:
<223> OTHER INFORMATION: Pseudomonas

<400> SEQUENCE: 13

Met Gln Thr Leu Ser Ile Gln His Gly Thr Leu Val Thr Met Asp Gln
1               5                   10                  15
Tyr Arg Arg Val Leu Gly Asp Ser Trp Val His Val Gln Asp Gly Arg
            20                  25                  30
Ile Val Ala Leu Gly Val His Ala Glu Ser Val Pro Pro Pro Ala Asp
        35                  40                  45
Arg Val Ile Asp Ala Arg Gly Lys Val Val Leu Pro Gly Phe Ile Asn
    50                  55                  60
Ala His Thr His Val Asn Gln Ile Leu Leu Arg Gly Gly Pro Ser His
65                  70                  75                  80
Gly Arg Gln Phe Tyr Asp Trp Leu Phe Asn Val Val Tyr Pro Gly Gln
                85                  90                  95
Lys Ala Met Arg Pro Glu Asp Val Ala Val Ala Val Arg Leu Tyr Cys
            100                 105                 110
Ala Glu Ala Val Arg Ser Gly Ile Thr Thr Ile Asn Glu Asn Ala Asp
        115                 120                 125
Ser Ala Ile Tyr Pro Gly Asn Ile Glu Ala Ala Met Ala Val Tyr Gly
    130                 135                 140
Glu Val Gly Val Arg Val Val Tyr Ala Arg Met Phe Phe Asp Arg Met
145                 150                 155                 160
Asp Gly Arg Ile Gln Gly Tyr Val Asp Ala Leu Lys Ala Arg Ser Pro
                165                 170                 175
Gln Val Glu Leu Cys Ser Ile Met Glu Glu Thr Ala Val Ala Lys Asp
            180                 185                 190
Arg Ile Thr Ala Leu Ser Asp Gln Tyr His Gly Thr Ala Gly Gly Arg
        195                 200                 205
Ile Ser Val Trp Pro Ala Pro Ala Thr Thr Thr Ala Val Thr Val Glu
    210                 215                 220
Gly Met Arg Trp Ala Gln Ala Phe Ala Arg Asp Arg Ala Val Met Trp
225                 230                 235                 240
Thr Leu His Met Ala Glu Ser Asp His Asp Glu Arg Ile His Gly Met
                245                 250                 255
Ser Pro Ala Glu Tyr Met Glu Cys His Gly Leu Leu Asp Glu Arg Leu
            260                 265                 270
```

```
Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
290                 295                 300

Leu Gly Ser Gly Val Ala Pro Val Pro Glu Met Val Glu Arg Gly Met
305                 310                 315                 320

Ala Met Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu Glu Met Thr Pro Leu Leu
465                 470                 475                 480

His Pro Pro Pro Leu Glu Glu Ile Ala Ala Ile Leu Ala Arg Leu Gly
                485                 490                 495
```

<210> SEQ ID NO 14
<211> LENGTH: 496
<212> TYPE: PRT
<213> ORGANISM: Artificial Sequence
<220> FEATURE:
<223> OTHER INFORMATION: Pseudomonas

<400> SEQUENCE: 14

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

Arg Val Ile Asp Ala Arg Gly Lys Val Val Leu Pro Gly Phe Ile Asn
50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
130                 135                 140
```

Glu Val Gly Val Arg Val Tyr Ala Arg Met Phe Phe Asp Arg Met
145                 150                 155                 160

Asp Gly Arg Ile Gln Gly Tyr Val Asp Ala Leu Lys Ala Arg Ser Pro
            165                 170                 175

Gln Val Glu Leu Cys Ser Ile Met Glu Glu Thr Ala Val Ala Lys Asp
        180                 185                 190

Arg Ile Thr Ala Leu Ser Asp Gln Tyr His Gly Thr Ala Gly Gly Arg
    195                 200                 205

Ile Ser Val Trp Pro Ala Pro Ala Thr Thr Thr Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu Glu Met Thr Pro Leu Leu
465                 470                 475                 480

His Pro Leu Pro Leu Glu Glu Ile Ala Ala Ile Leu Ala Arg Leu Gly
                485                 490                 495

<210> SEQ ID NO 15
<211> LENGTH: 496
<212> TYPE: PRT
<213> ORGANISM: Artificial Sequence
<220> FEATURE:
<223> OTHER INFORMATION: Pseudomonas

<400> SEQUENCE: 15

Met Gln Thr Leu Ser Ile Gln His Gly Thr Leu Val Thr Met Asp Gln
1               5                   10                  15

-continued

```
Tyr Arg Arg Val Leu Gly Asp Ser Trp Val His Val Gln Asp Gly Arg
             20                  25                  30

Ile Val Ala Leu Gly Val His Ala Glu Ser Val Pro Pro Pro Ala Asp
         35                  40                  45

Gln Val Ile Asp Ala Arg Gly Lys Val Val Leu Pro Gly Phe Ile Asn
     50                  55                  60

Ala His Thr His Val Asn Gln Ile Leu Leu Arg Gly Gly Pro Ser His
 65                  70                  75                  80

Gly Arg Gln Phe His Asp Trp Leu Phe Asn Val Val Tyr Pro Gly Gln
                 85                  90                  95

Lys Ala Met Arg Pro Glu Asp Val Ala Val Ala Val Arg Leu Tyr Cys
             100                 105                 110

Ala Glu Ala Val Arg Ser Gly Ile Thr Thr Ile Asn Glu Asn Ala Asp
         115                 120                 125

Ser Ala Ile Tyr Pro Gly Asn Ile Glu Ala Ala Met Ala Val Tyr Gly
     130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Gly Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
```

```
                435                 440                 445
Leu Glu Glu Ala Gln Ser Arg Ala Thr Ala Ile Leu Gln Arg Ala Asn
450                 455                 460

Met Val Ala Asn Pro Ala Trp Arg Ser Leu Glu Met Thr Pro Leu Leu
465                 470                 475                 480

His Pro Pro Leu Glu Ile Ala Ala Ile Leu Ala Arg Leu Gly
                485                 490                 495

<210> SEQ ID NO 16
<211> LENGTH: 496
<212> TYPE: PRT
<213> ORGANISM: Artificial Sequence
<220> FEATURE:
<223> OTHER INFORMATION: Pseudomonas

<400> SEQUENCE: 16

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Arg Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
            195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Ile Arg Leu Leu
            275                 280                 285

His Arg His Asn Val Lys Val Ala Ser Gln Ala Val Ser Asn Ala Tyr
    290                 295                 300

Leu Gly Ser Gly Val Ala Pro Val Pro Glu Met Val Glu Arg Gly Met
```

```
                305                 310                 315                 320
        Ala Val Gly Ile Gly Thr Asp Asn Gly Asn Ser Asn Asp Ser Val Asn
                        325                 330                 335

Met Ile Gly Asp Met Lys Phe Met Ala His Ile His Arg Ala Val His
                        340                 345                 350

Arg Asp Ala Asp Val Leu Thr Pro Glu Lys Ile Leu Glu Met Ala Thr
                        355                 360                 365

Ile Asp Gly Ala Arg Ser Leu Gly Met Asp His Glu Ile Gly Ser Ile
                        370                 375                 380

Glu Thr Gly Lys Arg Ala Asp Leu Ile Leu Asp Leu Arg His Pro
        385                 390                 395                 400

Gln Thr Thr Pro His His Leu Ala Ala Thr Ile Val Phe Gln Ala
                        405                 410                 415

Tyr Gly Asn Glu Val Asp Thr Val Leu Ile Asp Gly Asn Val Val Met
                        420                 425                 430

Glu Asn Arg Arg Leu Ser Phe Leu Pro Pro Glu Arg Glu Leu Ala Phe
                        435                 440                 445

Leu Glu Glu Ala Gln Ser Arg Ala Thr Ala Ile Leu Gln Arg Ala Asn
        450                 455                 460

Met Val Ala Asn Pro Ala Trp Arg Ser Leu Glu Met Thr Pro Leu Leu
        465                 470                 475                 480

His Pro Pro Leu Glu Glu Ile Ala Ala Ile Leu Ala Gln Leu Gly
                        485                 490                 495

<210> SEQ ID NO 17
<211> LENGTH: 474
<212> TYPE: PRT
<213> ORGANISM: Artificial Sequence
<220> FEATURE:
<223> OTHER INFORMATION: Pseudomonas

<400> SEQUENCE: 17

Met Gln Thr Leu Ser Ile Gln His Gly Thr Leu Val Thr Met Asp Gln
        1               5                   10                  15

Tyr Arg Arg Val Leu Gly Asp Ser Trp Val His Val Gln Asp Gly Arg
                        20                  25                  30

Ile Val Ala Leu Gly Val His Ala Glu Ser Val Pro Pro Pro Ala Asp
                        35                  40                  45

Arg Val Ile Asp Ala Arg Gly Lys Val Val Leu Pro Gly Phe Ile Asn
                        50                  55                  60

Ala His Thr His Val Asn Gln Ile Leu Leu Arg Gly Gly Pro Ser His
        65                  70                  75                  80

Gly Arg Gln Phe Tyr Asp Trp Leu Phe Asn Val Val Tyr Pro Gly Gln
                        85                  90                  95

Lys Ala Met Arg Pro Glu Asp Val Ala Val Ala Val Arg Leu Tyr Cys
                        100                 105                 110

Ala Glu Ala Val Arg Ser Gly Ile Thr Thr Ile Asn Glu Asn Ala Asp
                        115                 120                 125

Ser Ala Ile Tyr Pro Gly Asn Ile Glu Ala Ala Met Ala Val Tyr Gly
                        130                 135                 140

Glu Val Gly Val Arg Val Val Tyr Ala Arg Met Phe Phe Asp Arg Met
        145                 150                 155                 160

Asp Gly Arg Ile Gln Gly Tyr Val Asp Ala Leu Lys Ala Arg Ser Pro
                        165                 170                 175

Gln Val Glu Leu Cys Ser Ile Met Glu Glu Thr Ala Val Ala Lys Asp
```

```
                180             185              190
Arg Ile Thr Ala Leu Ser Asp Gln Tyr His Gly Thr Ala Gly Gly Arg
            195                 200             205
Ile Ser Val Trp Pro Ala Pro Ala Thr Thr Thr Ala Val Thr Val Glu
            210                 215                 220
Gly Met Arg Trp Ala Gln Ala Phe Ala Arg Asp Arg Ala Val Met Trp
225                 230                 235                 240
Thr Leu His Met Ala Glu Ser Asp His Asp Glu Arg Ile His Gly Met
                245                 250                 255
Ser Pro Ala Glu Tyr Met Glu Cys Tyr Gly Leu Leu Asp Glu Arg Leu
                260                 265                 270
Gln Val Ala His Cys Val Tyr Phe Asp Arg Lys Asp Val Arg Leu Leu
                275                 280                 285
His Arg His Asn Val Lys Val Ala Ser Gln Val Val Ser Asn Ala Tyr
                290                 295                 300
Leu Gly Ser Gly Val Ala Pro Val Pro Glu Met Val Glu Arg Gly Met
305                 310                 315                 320
Ala Val Gly Ile Gly Thr Asp Asn Gly Asn Ser Asn Asp Ser Val Asn
                325                 330                 335
Met Ile Gly Asp Met Lys Phe Met Ala His Ile His Arg Ala Val His
                340                 345                 350
Arg Asp Ala Asp Val Leu Thr Pro Glu Lys Ile Leu Glu Met Ala Thr
                355                 360                 365
Ile Asp Gly Ala Arg Ser Leu Gly Met Asp His Glu Ile Gly Ser Ile
                370                 375                 380
Glu Thr Gly Lys Arg Ala Asp Leu Ile Leu Leu Asp Leu Arg His Pro
385                 390                 395                 400
Gln Thr Thr Pro His His His Leu Ala Ala Thr Ile Val Phe Gln Ala
                405                 410                 415
Tyr Gly Asn Glu Val Asp Thr Val Leu Ile Asp Gly Asn Val Val Met
                420                 425                 430
Glu Asn Arg Arg Leu Ser Phe Leu Pro Pro Glu Arg Glu Leu Ala Phe
                435                 440                 445
Leu Glu Glu Ala Gln Ser Arg Ala Thr Ala Ile Leu Gln Arg Ala Asn
                450                 455                 460
Met Val Ala Asn Pro Ala Trp Arg Ser Leu
465                 470

<210> SEQ ID NO 18
<211> LENGTH: 474
<212> TYPE: PRT
<213> ORGANISM: Artificial Sequence
<220> FEATURE:
<223> OTHER INFORMATION: Bacterial

<400> SEQUENCE: 18

Met Gln Thr Leu Ser Ile Gln His Gly Thr Leu Val Thr Met Asp Gln
1               5                   10                  15
Tyr Arg Arg Val Leu Gly Asp Ser Trp Val His Val Gln Asp Gly Arg
                20                  25                  30
Ile Val Ala Leu Gly Val His Ala Glu Ser Val Pro Pro Ala Asp
                35                  40                  45
Arg Val Ile Asp Ala Arg Gly Lys Val Val Leu Pro Gly Phe Ile Asn
            50                  55                  60
Ala His Thr His Val Asn Gln Ile Leu Leu Arg Gly Gly Pro Ser His
```

```
                65                  70                  75                  80
Gly Arg Gln Leu Tyr Asp Trp Leu Phe Asn Val Val Tyr Pro Gly Gln
                    85                  90                  95

Arg Ala Met Arg Pro Glu Asp Val Ala Val Arg Leu Tyr Cys
                100                 105                 110

Ala Glu Ala Val Arg Ser Gly Ile Thr Thr Ile Asn Glu Asn Ala Asp
                115                 120                 125

Ser Ala Ile Tyr Pro Gly Asn Ile Glu Ala Ala Met Ala Val Tyr Gly
            130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                    165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
            195                 200                 205

Ile Ser Val Trp Pro Ala Pro Ala Thr Thr Thr Ala Val Thr Val Glu
        210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                    245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
        290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                    325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
        370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                    405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
        450                 455                 460

Met Val Ala Asn Pro Ala Trp Arg Ser Leu
465                 470

<210> SEQ ID NO 19
```

<211> LENGTH: 474
<212> TYPE: PRT
<213> ORGANISM: Artificial Sequence
<220> FEATURE:
<223> OTHER INFORMATION: Bacterial

<400> SEQUENCE: 19

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380
```

```
Glu Thr Gly Lys Arg Ala Asp Leu Ile Leu Leu Asp Leu Arg His Pro
385                 390                 395                 400

Gln Thr Thr Pro His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470
```

<210> SEQ ID NO 20
<211> LENGTH: 474
<212> TYPE: PRT
<213> ORGANISM: Artificial Sequence
<220> FEATURE:
<223> OTHER INFORMATION: Bacterial

<400> SEQUENCE: 20

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270
```

```
Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
        290                 295                 300

Leu Gly Ser Gly Val Ala Pro Val Pro Glu Met Val Glu Arg Gly Met
305                 310                 315                 320

Ala Val Gly Ile Gly Thr Asp Gly Asn Ser Asn Asp Ser Val Asn
            325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
        370                 375                 380

Glu Thr Gly Lys Arg Ala Asp Leu Ile Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu
465                 470

<210> SEQ ID NO 21
<211> LENGTH: 474
<212> TYPE: PRT
<213> ORGANISM: Artificial Sequence
<220> FEATURE:
<223> OTHER INFORMATION: Bacterial

<400> SEQUENCE: 21

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Tyr Pro Gly Gln
            85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160
```

Asp Gly Arg Ile Gln Gly Tyr Val Asp Ala Leu Lys Ala Arg Ser Pro
            165                 170                 175

Gln Val Glu Leu Cys Ser Ile Met Glu Thr Ala Val Ala Lys Asp
        180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
        290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
        370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
        450                 455                 460

Met Val Ala Asn Pro Ala Trp Arg Ser Leu
465                 470

<210> SEQ ID NO 22
<211> LENGTH: 474
<212> TYPE: PRT
<213> ORGANISM: Artificial Sequence
<220> FEATURE:
<223> OTHER INFORMATION: Bacterial

<400> SEQUENCE: 22

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Ala Asp
        35                  40                  45

```
Arg Val Ile Asp Ala Arg Gly Lys Val Val Leu Pro Gly Phe Ile Asn
         50                  55                  60

Ala His Thr His Val Asn Gln Ile Leu Leu Arg Gly Gly Pro Ser His
 65                  70                  75                  80

Gly Arg Gln Leu Tyr Asp Trp Leu Phe Asn Val Val Tyr Pro Gly Gln
                     85                  90                  95

Lys Ala Met Arg Pro Glu Asp Val Ala Val Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                    165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
        210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
                275                 280                 285

His Arg His Asn Val Lys Val Ala Ser Gln Val Val Ser Asn Ala Tyr
        290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
    450                 455                 460
```

Met Val Ala Asn Pro Ala Trp Arg Ser Leu
465                 470

<210> SEQ ID NO 23
<211> LENGTH: 474
<212> TYPE: PRT
<213> ORGANISM: Artificial Sequence
<220> FEATURE:
<223> OTHER INFORMATION: Bacterial

<400> SEQUENCE: 23

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Pro Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

```
Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
370                 375                 380

Glu Thr Gly Lys Arg Ala Asp Leu Ile Leu Leu Asp Leu Arg His Pro
385                 390                 395                 400

Gln Thr Thr Pro His His Leu Ala Ala Thr Ile Val Phe Gln Ala
            405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu
465                 470
```

<210> SEQ ID NO 24
<211> LENGTH: 474
<212> TYPE: PRT
<213> ORGANISM: Artificial Sequence
<220> FEATURE:
<223> OTHER INFORMATION: Bacterial

<400> SEQUENCE: 24

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

Arg Val Ile Asp Ala Arg Gly Lys Val Val Leu Pro Gly Phe Ile Asn
50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
210                 215                 220

Gly Met Arg Trp Ala Gln Ala Phe Ala Arg Asp Arg Ala Val Met Trp
225                 230                 235                 240
```

```
Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470

<210> SEQ ID NO 25
<211> LENGTH: 474
<212> TYPE: PRT
<213> ORGANISM: Artificial Sequence
<220> FEATURE:
<223> OTHER INFORMATION: Bacterial

<400> SEQUENCE: 25

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125
```

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470

<210> SEQ ID NO 26
<211> LENGTH: 481
<212> TYPE: PRT
<213> ORGANISM: Artificial Sequence
<220> FEATURE:
<223> OTHER INFORMATION: Bacterial

<400> SEQUENCE: 26

Met Thr Thr Thr Leu Tyr Thr Gly Phe His Gln Leu Val Thr Gly Asp
1               5                   10                  15

-continued

Val Ala Gly Thr Val Leu Asn Gly Val Asp Ile Leu Val Arg Asp Gly
            20                  25                  30

Glu Ile Ile Gly Leu Gly Pro Asp Leu Pro Arg Thr Leu Ala Pro Ile
        35                  40                  45

Gly Val Gly Gln Glu Gln Gly Val Glu Val Val Asn Cys Arg Gly Leu
    50                  55                  60

Thr Ala Tyr Pro Gly Leu Ile Asn Thr His His Phe Gln Ala
65                  70                  75                  80

Phe Val Arg Asn Leu Ala Pro Leu Asp Trp Thr Gln Leu Asp Val Leu
                85                  90                  95

Ala Trp Leu Arg Lys Ile Tyr Pro Val Phe Ala Leu Val Asp Glu Asp
            100                 105                 110

Cys Ile Tyr His Ser Thr Val Val Ser Met Ala Glu Leu Ile Lys His
            115                 120                 125

Gly Cys Thr Thr Ala Phe Asp His Gln Tyr Asn Tyr Ser Arg Arg Gly
        130                 135                 140

Gly Pro Phe Leu Val Asp Arg Gln Phe Asp Ala Ala Asn Leu Leu Gly
145                 150                 155                 160

Leu Arg Phe His Ala Gly Arg Gly Cys Ile Thr Leu Pro Met Ala Glu
                165                 170                 175

Gly Ser Thr Ile Pro Asp Ala Met Arg Glu Ser Thr Asp Thr Phe Leu
            180                 185                 190

Ala Asp Cys Glu Arg Leu Val Ser Arg Phe His Asp Pro Arg Pro Phe
        195                 200                 205

Ala Met Gln Arg Val Val Ala Pro Ser Ser Pro Val Ile Ala Tyr
    210                 215                 220

Pro Glu Thr Phe Val Glu Ser Ala Arg Leu Ala Arg His Leu Gly Val
225                 230                 235                 240

Ser Leu His Thr His Leu Gly Glu Gly Glu Thr Pro Ala Met Val Ala
                245                 250                 255

Arg Phe Gly Glu Arg Ser Leu Asp Trp Cys Glu Asn Arg Gly Phe Val
            260                 265                 270

Gly Pro Asp Val Trp Leu Ala His Gly Trp Glu Phe Thr Ala Ala Asp
        275                 280                 285

Ile Ala Arg Leu Ala Ala Thr Gly Thr Gly Val Ala His Cys Pro Ala
    290                 295                 300

Pro Val Phe Leu Val Gly Ala Glu Val Thr Asp Ile Pro Ala Met Ala
305                 310                 315                 320

Ala Ala Gly Val Arg Val Gly Phe Gly Val Asp Gly His Ala Ser Asn
                325                 330                 335

Asp Ser Ser Asn Leu Ala Glu Cys Ile Arg Leu Ala Tyr Leu Leu Gln
            340                 345                 350

Cys Leu Lys Ala Ser Glu Arg Gln His Pro Val Pro Ala Pro Tyr Asp
        355                 360                 365

Phe Leu Arg Met Ala Thr Gln Gly Gly Ala Asp Cys Leu Asn Arg Pro
    370                 375                 380

Asp Leu Gly Ala Leu Ala Val Gly Arg Ala Ala Asp Phe Phe Ala Val
385                 390                 395                 400

Asp Leu Asn Arg Ile Glu Tyr Ile Gly Ala Asn His Asp Pro Arg Ser
                405                 410                 415

Leu Pro Ala Lys Val Gly Phe Ser Gly Pro Val Asp Met Thr Val Ile
            420                 425                 430

Asn Gly Lys Val Val Trp Arg Asn Gly Glu Phe Pro Gly Leu Asp Glu

```
              435                 440                 445
Met Glu Leu Ala Arg Ala Ala Asp Gly Val Phe Arg Arg Val Ile Tyr
    450                 455                 460

Gly Asp Pro Leu Val Ala Ala Leu Arg Arg Gly Thr Gly Val Thr Pro
465                 470                 475                 480

Cys

<210> SEQ ID NO 27
<211> LENGTH: 403
<212> TYPE: PRT
<213> ORGANISM: Artificial Sequence
<220> FEATURE:
<223> OTHER INFORMATION: Bacterial

<400> SEQUENCE: 27

Met Ser Lys Asp Phe Asp Leu Ile Ile Arg Asn Ala Tyr Leu Ser Glu
1               5                   10                  15

Lys Asp Ser Val Tyr Asp Ile Gly Ile Val Gly Asp Arg Ile Ile Lys
            20                  25                  30

Ile Glu Ala Lys Ile Glu Gly Thr Val Lys Asp Glu Ile Asp Ala Lys
        35                  40                  45

Gly Asn Leu Val Ser Pro Gly Phe Val Asp Ala His Thr His Met Asp
    50                  55                  60

Lys Ser Phe Thr Ser Thr Gly Glu Arg Leu Pro Lys Phe Trp Ser Arg
65                  70                  75                  80

Pro Tyr Thr Arg Asp Ala Ala Ile Glu Asp Gly Leu Lys Tyr Tyr Lys
                85                  90                  95

Asn Ala Thr His Glu Glu Ile Lys Arg His Val Ile Glu His Ala His
            100                 105                 110

Met Gln Val Leu His Gly Thr Leu Tyr Thr Arg Thr His Val Asp Val
        115                 120                 125

Asp Ser Val Ala Lys Thr Lys Ala Val Glu Ala Val Leu Glu Ala Lys
    130                 135                 140

Glu Glu Leu Lys Asp Leu Ile Asp Ile Gln Val Val Ala Phe Ala Gln
145                 150                 155                 160

Ser Gly Phe Phe Val Asp Leu Glu Ser Glu Ser Leu Ile Arg Lys Ser
                165                 170                 175

Leu Asp Met Gly Cys Asp Leu Val Gly Gly Val Asp Pro Ala Thr Arg
            180                 185                 190

Glu Asn Asn Val Glu Gly Ser Leu Asp Leu Cys Phe Lys Leu Ala Lys
        195                 200                 205

Glu Tyr Asp Val Asp Ile Asp Tyr His Ile His Asp Ile Gly Thr Val
    210                 215                 220

Gly Val Tyr Ser Ile Asn Arg Leu Ala Gln Lys Thr Ile Glu Asn Gly
225                 230                 235                 240

Tyr Lys Gly Arg Val Thr Thr Ser His Ala Trp Cys Phe Ala Asp Ala
                245                 250                 255

Pro Ser Glu Trp Leu Asp Glu Ala Ile Pro Leu Tyr Lys Asp Ser Gly
            260                 265                 270

Met Lys Phe Val Thr Cys Phe Ser Ser Thr Pro Pro Thr Met Pro Val
        275                 280                 285

Ile Lys Leu Leu Glu Ala Gly Ile Asn Leu Gly Cys Ala Ser Asp Asn
    290                 295                 300

Ile Arg Asp Phe Trp Val Pro Phe Gly Asn Gly Asp Met Val Gln Gly
305                 310                 315                 320
```

Ala Leu Ile Glu Thr Gln Arg Leu Glu Leu Lys Thr Asn Arg Asp Leu
            325                 330                 335

Gly Leu Ile Trp Lys Met Ile Thr Ser Glu Gly Ala Arg Val Leu Gly
            340                 345                 350

Ile Glu Lys Asn Tyr Gly Ile Glu Val Gly Lys Lys Ala Asp Leu Val
            355                 360                 365

Val Leu Asn Ser Leu Ser Pro Gln Trp Ala Ile Asp Gln Ala Lys
370                 375                 380

Arg Leu Cys Val Ile Lys Asn Gly Arg Ile Val Lys Asp Glu Val
385                 390                 395                 400

Ile Val Ala

<210> SEQ ID NO 28
<211> LENGTH: 363
<212> TYPE: PRT
<213> ORGANISM: Artificial Sequence
<220> FEATURE:
<223> OTHER INFORMATION: Bacterial

<400> SEQUENCE: 28

Met Tyr His Ile Asp Val Phe Arg Ile Pro Cys His Ser Pro Gly Asp
1               5                   10                  15

Thr Ser Gly Leu Glu Asp Leu Ile Glu Thr Gly Arg Val Ala Pro Ala
            20                  25                  30

Asp Ile Val Ala Val Met Gly Lys Thr Glu Gly Asn Gly Cys Val Asn
            35                  40                  45

Asp Tyr Thr Arg Glu Tyr Ala Thr Ala Met Leu Ala Ala Cys Leu Gly
        50                  55                  60

Arg His Leu Gln Leu Pro Pro His Glu Val Lys Arg Val Ala Phe
65                  70                  75                  80

Val Met Ser Gly Gly Thr Glu Gly Val Leu Ser Pro His His Thr Val
                85                  90                  95

Phe Ala Arg Arg Pro Ala Ile Asp Ala His Arg Pro Ala Gly Lys Arg
            100                 105                 110

Leu Thr Leu Gly Ile Ala Phe Thr Arg Asp Phe Leu Pro Glu Glu Ile
            115                 120                 125

Gly Arg His Ala Gln Ile Thr Glu Thr Ala Gly Ala Val Lys Arg Ala
        130                 135                 140

Met Arg Asp Ala Gly Ile Ala Ser Ile Asp Asp Leu His Phe Val Gln
145                 150                 155                 160

Val Lys Cys Pro Leu Leu Thr Pro Ala Lys Ile Ala Ser Ala Arg Ser
                165                 170                 175

Arg Gly Cys Ala Pro Val Thr Thr Asp Thr Tyr Glu Ser Met Gly Tyr
            180                 185                 190

Ser Arg Gly Ala Ser Ala Leu Gly Ile Ala Leu Ala Thr Glu Glu Val
        195                 200                 205

Pro Ser Ser Met Leu Val Asp Glu Ser Val Leu Asn Asp Trp Ser Leu
210                 215                 220

Ser Ser Ser Leu Ala Ser Ala Ser Ala Gly Ile Glu Leu Glu His Asn
225                 230                 235                 240

Val Val Ile Ala Ile Gly Met Ser Glu Gln Ala Thr Ser Glu Leu Val
                245                 250                 255

Ile Ala His Gly Val Met Ser Asp Ala Ile Asp Ala Ala Ser Val Arg
            260                 265                 270

```
Arg Thr Ile Glu Ser Leu Gly Ile Arg Ser Asp Asp Glu Met Asp Arg
            275                 280                 285

Ile Val Asn Val Phe Ala Lys Ala Glu Ala Ser Pro Asp Gly Val Val
290                 295                 300

Arg Gly Met Arg His Thr Met Leu Ser Asp Ser Asp Ile Asn Ser Thr
305                 310                 315                 320

Arg His Ala Arg Ala Val Thr Gly Ala Ala Ile Ala Ser Val Val Gly
                325                 330                 335

His Gly Met Val Tyr Val Ser Gly Ala Glu His Gln Gly Pro Ala
                340                 345                 350

Gly Gly Gly Pro Phe Ala Val Ile Ala Arg Ala
            355                 360
```

<210> SEQ ID NO 29
<211> LENGTH: 457
<212> TYPE: PRT
<213> ORGANISM: Artificial Sequence
<220> FEATURE:
<223> OTHER INFORMATION: Bacterial

<400> SEQUENCE: 29

```
Met Lys Thr Val Glu Ile Ile Glu Gly Ile Ala Ser Gly Arg Thr Ser
1               5                   10                  15

Ala Arg Asp Val Cys Glu Glu Ala Leu Ala Thr Ile Gly Ala Thr Asp
                20                  25                  30

Gly Leu Ile Asn Ala Phe Thr Cys Arg Thr Val Glu Arg Ala Arg Ala
            35                  40                  45

Glu Ala Asp Ala Ile Asp Val Arg Arg Ala Arg Gly Glu Val Leu Pro
50                  55                  60

Pro Leu Ala Gly Leu Pro Tyr Ala Val Lys Asn Leu Phe Asp Ile Glu
65                  70                  75                  80

Gly Val Thr Thr Leu Ala Gly Ser Lys Ile Asn Arg Thr Leu Pro Pro
                85                  90                  95

Ala Arg Ala Asp Ala Val Leu Val Gln Arg Leu Lys Ala Ala Gly Ala
            100                 105                 110

Val Leu Leu Gly Gly Leu Asn Met Asp Glu Phe Ala Tyr Gly Phe Thr
        115                 120                 125

Thr Glu Asn Thr His Tyr Gly Pro Thr Arg Asn Pro His Asp Thr Gly
130                 135                 140

Arg Ile Ala Gly Gly Ser Ser Gly Ser Gly Ala Ala Ile Ala Ala
145                 150                 155                 160

Gly Gln Val Pro Leu Ser Leu Gly Ser Asp Thr Asn Gly Ser Ile Arg
                165                 170                 175

Val Pro Ala Ser Leu Cys Gly Val Trp Gly Leu Lys Pro Thr Phe Gly
            180                 185                 190

Arg Leu Ser Arg Arg Gly Thr Tyr Pro Phe Val His Ser Ile Asp His
        195                 200                 205

Leu Gly Pro Leu Ala Asp Ser Val Glu Gly Leu Ala Leu Ala Tyr Asp
210                 215                 220

Ala Met Gln Gly Pro Asp Pro Leu Asp Pro Gly Cys Ser Ala Ser Arg
225                 230                 235                 240

Ile Gln Pro Ser Val Pro Val Leu Ser Gln Gly Ile Ala Gly Leu Arg
                245                 250                 255

Ile Gly Val Leu Gly Gly Trp Phe Arg Asp Asn Ala Gly Pro Ala Ala
            260                 265                 270
```

```
Arg Ala Ala Val Asp Val Ala Leu Thr Leu Gly Ala Ser Glu Val
            275                 280                 285
Val Met Trp Pro Asp Ala Glu Ile Gly Arg Ala Ala Phe Val Ile
290                 295                 300
Thr Ala Ser Glu Gly Gly Cys Leu His Leu Asp Asp Leu Arg Ile Arg
305                 310                 315                 320
Pro Gln Asp Phe Glu Pro Leu Ser Val Asp Arg Phe Ile Ser Gly Val
                325                 330                 335
Leu Gln Pro Val Ala Trp Tyr Leu Arg Ala Gln Arg Phe Arg Arg Val
            340                 345                 350
Tyr Arg Asp Lys Val Asn Ala Leu Phe Arg Asp Trp Asp Ile Leu Ile
355                 360                 365
Ala Pro Ala Thr Pro Ile Ser Ala Pro Ala Ile Gly Thr Glu Trp Ile
370                 375                 380
Glu Val Asn Gly Thr Arg His Pro Cys Arg Pro Ala Met Gly Leu Leu
385                 390                 395                 400
Thr Gln Pro Val Ser Phe Ala Gly Cys Pro Val Val Ala Ala Pro Thr
                405                 410                 415
Trp Pro Gly Glu Asn Asp Gly Met Pro Ile Gly Val Gln Leu Ile Ala
                420                 425                 430
Ala Pro Trp Asn Glu Ser Leu Cys Leu Arg Ala Gly Lys Val Leu Gln
            435                 440                 445
Asp Thr Gly Ile Ala Arg Leu Lys Cys
            450                 455

<210> SEQ ID NO 30
<211> LENGTH: 605
<212> TYPE: PRT
<213> ORGANISM: Artificial Sequence
<220> FEATURE:
<223> OTHER INFORMATION: Bacterial

<400> SEQUENCE: 30

Met Asn Asp Arg Ala Pro His Pro Glu Arg Ser Gly Arg Val Thr Pro
1               5                   10                  15
Asp His Leu Thr Asp Leu Ala Ser Tyr Gln Ala Ala Tyr Ala Ala Gly
            20                  25                  30
Thr Asp Ala Ala Asp Val Ile Ser Asp Leu Tyr Ala Arg Ile Lys Glu
        35                  40                  45
Asp Gly Glu Asn Pro Ile Trp Ile Ser Leu Leu Pro Leu Glu Ser Ala
    50                  55                  60
Leu Ala Met Leu Ala Asp Ala Gln Gln Arg Lys Asp Lys Gly Glu Ala
65                  70                  75                  80
Leu Pro Leu Phe Gly Ile Pro Phe Gly Val Lys Asp Asn Ile Asp Val
                85                  90                  95
Ala Gly Leu Pro Thr Thr Ala Gly Cys Thr Gly Phe Ala Arg Thr Pro
            100                 105                 110
Arg Gln His Ala Phe Val Val Gln Arg Leu Val Asp Ala Gly Ala Ile
        115                 120                 125
Pro Ile Gly Lys Thr Asn Leu Asp Gln Phe Ala Thr Gly Leu Asn Gly
    130                 135                 140
Thr Arg Thr Pro Phe Gly Ile Pro Arg Cys Val Phe Asn Glu Asn Tyr
145                 150                 155                 160
Val Ser Gly Gly Ser Ser Gly Ser Ala Val Ala Val Ala Asn Gly
                165                 170                 175
```

```
Thr Val Pro Phe Ser Leu Gly Thr Asp Thr Ala Gly Ser Gly Arg Ile
                180                 185                 190
Pro Ala Ala Phe Asn Asn Leu Val Gly Leu Lys Pro Thr Lys Gly Leu
            195                 200                 205
Phe Ser Gly Ser Gly Leu Val Pro Ala Ala Arg Ser Leu Asp Cys Ile
        210                 215                 220
Ser Val Leu Ala His Thr Val Asp Asp Ala Leu Ala Val Ala Arg Val
225                 230                 235                 240
Ala Ala Gly Tyr Asp Ala Asp Asp Ala Phe Ser Arg Lys Ala Gly Ala
                245                 250                 255
Ala Ala Leu Thr Glu Lys Ser Trp Pro Arg Arg Phe Asn Phe Gly Val
            260                 265                 270
Pro Ala Ala Glu His Arg Gln Phe Phe Gly Asp Ala Glu Ala Glu Ala
        275                 280                 285
Leu Phe Asn Lys Ala Val Arg Lys Leu Glu Glu Met Gly Gly Thr Cys
    290                 295                 300
Ile Ser Phe Asp Tyr Thr Pro Phe Arg Gln Ala Ala Glu Leu Leu Tyr
305                 310                 315                 320
Ala Gly Pro Trp Val Ala Glu Arg Leu Ala Ala Ile Glu Ser Leu Ala
                325                 330                 335
Asp Glu His Pro Glu Val Leu His Pro Val Val Arg Asp Ile Ile Leu
            340                 345                 350
Ser Ala Lys Arg Met Ser Ala Val Asp Thr Phe Asn Gly Ile Tyr Arg
        355                 360                 365
Leu Ala Asp Leu Val Arg Ala Ala Glu Ser Thr Trp Glu Lys Ile Asp
    370                 375                 380
Val Met Leu Leu Pro Thr Ala Pro Thr Ile Tyr Thr Val Glu Asp Met
385                 390                 395                 400
Leu Ala Asp Pro Val Arg Leu Asn Ser Asn Leu Gly Phe Tyr Thr Asn
                405                 410                 415
Phe Val Asn Leu Met Asp Leu Ser Ala Ile Ala Val Pro Ala Gly Phe
            420                 425                 430
Arg Thr Asn Gly Leu Pro Phe Gly Val Thr Phe Ile Gly Arg Ala Phe
        435                 440                 445
Glu Asp Gly Ala Ile Ala Ser Leu Gly Lys Ala Phe Val Glu His Asp
    450                 455                 460
Leu Ala Lys Gly Asn Ala Ala Thr Ala Ala Pro Pro Lys Asp Thr Val
465                 470                 475                 480
Ala Ile Ala Val Val Gly Ala His Leu Ser Asp Gln Pro Leu Asn His
                485                 490                 495
Gln Leu Thr Glu Ser Gly Gly Lys Leu Arg Ala Thr Thr Arg Thr Ala
            500                 505                 510
Pro Gly Tyr Ala Leu Tyr Ala Leu Arg Asp Ala Thr Pro Ala Lys Pro
        515                 520                 525
Gly Met Leu Arg Asp Gln Asn Ala Val Gly Ser Ile Glu Val Glu Ile
    530                 535                 540
Trp Asp Leu Pro Val Ala Gly Phe Gly Ala Phe Val Ser Glu Ile Pro
545                 550                 555                 560
Ala Pro Leu Gly Ile Gly Thr Ile Thr Leu Glu Asp Gly Ser His Val
                565                 570                 575
Lys Gly Phe Leu Cys Glu Pro His Ala Ile Glu Thr Ala Leu Asp Ile
            580                 585                 590
Thr His Tyr Gly Gly Trp Arg Ala Tyr Leu Ala Ala Gln
```

<210> SEQ ID NO 31
<211> LENGTH: 225
<212> TYPE: PRT
<213> ORGANISM: Artificial Sequence
<220> FEATURE:
<223> OTHER INFORMATION: Bacterial

<400> SEQUENCE: 31

```
Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 32
<211> LENGTH: 3199
<212> TYPE: DNA
<213> ORGANISM: Glycine max

<400> SEQUENCE: 32

```
aaatttaatc gcttgtcaaa gaattcaaaa caacacagtc tgagaattct tttgattctt    60
ccatttccct aatacaaaag tgttcaaagg actaaccgtc tgagaattat tttgtatccc   120
cattcacaaa gtatcaaaga tttaacagcc taagatcttt gtcttaacac attggagggt   180
acatcctttg tggtacaagt agagggtaca tctacttggg tttgactgag aacaagagag   240
ggtacatctc ttgtggatta gttctagtgg agggtacatc cactaggttc aaagagaaca   300
agggagggta catcccttgt ggatctttgc ttgtaaaagg attttatata ggttgaaaga   360
aatctcaagg accgcaggtc acttggggac tggatgtagg cacaggttgt tgccgaacca   420
```

```
gtataaaaac tcttgtgtgt ttgtcttctt cttccctact cttttacttt ccgctgtgca    480
tttaatttcc tcttttactt tctgttaagt ttctcttcta ctcctcattc tcttaacaat    540
ttagtaaaag ccttagaaga gtaatttta attagtaaag gtttaggaat aattaattca     600
accccccctt cttaattatt ttgaggccac tcgatccaac aggaatgaca ggtcttcta     660 gcctgagcga tgaggaagaa agggagaagg gttttggtaa ctgatcgcgt ggtgggaaag    720 cagatttgg ggttttaagt tatgaataag acaacatcgg tttcttaaac aaaaccgatg    780
ttaactttac aatgttaaca tcattttttc aaaatccgat gttaactttc tacagttaac    840
atcgattttt caataaccga tgttaagata ttaaagttaa catcgggttt tagaaaaacc    900
gatttaacat caacttgtta acattggttg tttaaaaacc gatgttaatt aagtcaactt    960
atttaccaaa atgccaccat gcttttattt acatcggttt tccgaaaaac cgatgttaag   1020
cttgcgatgt taaatcaata aattgtagta atgaatcttc atacgattcg acaaatccta   1080
gaagaatggt tttacaaaga agatctcaga cacaataaat gaggtcttaa atgatatcac   1140
acatgtcgta tcaaatcatg actccatttg cctatcatct aaaatatcag agcatattg    1200 attttttaacg catgatttga aaaaaaaaa tcagatacaa aatatcaaac acataacaca   1260 actttaact tttatgttta tttacatctt atcaaaataa ttaagagtca tgatttatct    1320
ttaaaacgca aatatctttt ttactcaaca aaattatacc atgacactct tcaaattaga   1380
catttgaaaa ccaatttgct tagtcctcag tcctctcttc tcactcccaa tcaccaattg   1440
taatctgaaa aactaaaatg tagccctcat cattgttttt ctgatgataa gacaaaaata   1500
tatatcatta tacagagtat atatgggta ttcttcacatc aagcatcaca gtatatgacc    1560
aaatttcagc ctcccttgc taactgttat aaaggtatga aaataatgc acatgtaacc    1620 accattcgtt ctatatatga tgataacata tgctctgatt tccctttac ctatgatatt    1680 aaagtcctaa tcttaatcca aaactcatat atgcttgcaa attaaactat ctgtaatttt   1740
ttgttattat caatctacaa cttcgttttt acaccagaaa atagaaatgc catgtcaatg   1800
tcaaacacaa ctgagagttt cattttcaca tttctcttctt cctttggat gttcttggtt   1860 cgattggaaa ttgaaatgaa cccgttccag aaacgcctag gagaccatgt ccttgtttaa   1920 gcaattaaaaa acataaatgg agagttttt tcattgacta gtcaactcaa gttctgggtg   1980
atcacgttac cctaattgtg tgttccccat tttgtgttcc cattatttta tattgtccta   2040
tataaataat aatagactta aatatatttt ttttatttt aataaatatt tgaatttatg    2100 tttttttcagt aataatttt tttcattaaa ttttaataa aataatactt ttatttttta    2160
tccttgatat tttatttat tatatgataa attagtaaat tttatgttta ttttctaata    2220
aattaaagaa ttttgtttta atcttgacta ataataaatg aaaaaaaatt atcaagtaac    2280
agatacaaaa tttactaaat tatgagagac taaaaaagtg tcaaaaataa aaaataaaaa    2340 aattattttta ttaaggattc aacataaaaa attattagaa aataaaaata aaaataaaat    2400
atttattaaa aatataaaat ataattaagc ctaaataata tctataaaga tcttggatga    2460 aactttcat tgctgctaat gctggttaat catttgctta tttaataag cagtgacctc    2520 actcgcagct cacacaaaat tgtacattgg tattattgga aagagtcgtt taagattttg   2580
ttaaataggt tgcaactagc tcttgtatca aaagggctac accctcaaaa ttaattaaaa    2640
tatcccaaga atataaatagt aattttttttt tgcactatgg cattgttgga aatctttaga   2700
taacatggta ttgcgtgtag agactggcac agactgagaa ggtcgaaaac aaaagaacaa    2760
ggctttcttt ctctctctct ctttcttgtt cattttctct cacttgaaac atgcacacgg   2820
```

-continued

```
tgctctgaaa gttctaaccc caaagttggg aacacactgg gacgatatta tagcatatct   2880
ctagaaaggt gattcttctc actctctctc tccaacacac tatttaaata caactatagc   2940
cctcttcttt ctcccatgca acttgtctta atttcttttct cgatccccaa catcactagc   3000
tagctccttt tgtacacact ctacaacccc acctagctac atcacttaat tagttttccc   3060
atatctataa ccaatttcaa attctcaccc ttaactagct agctatattt cataactgat   3120
tattaccaac tcactacata ttattggcta ggattcacca ttagacttaa aagtagttga   3180
tttattatat atataaggg                                                3199
```

PLANTS HAVING INCREASED TOLERANCE TO HERBICIDES

This application is a National Stage Application of International Application No. PCT/IB2016/050268, filed Jan. 20, 2016, which claims priority to European Application No. EP15151966.7, filed on Jan. 21, 2015, the entire content of which is incorporated herein by reference.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "77560_SeqListing.txt", what was created on Jul. 17, 2017 and is 117,093 bytes in size. The subject matter of the Sequence Listing is incorporated herein in its entirety by reference.

FIELD OF THE INVENTION

The present invention relates in general to methods for conferring on plants agricultural level tolerance to herbicides. Particularly, the invention refers to plants having an increased tolerance to herbicides, more specifically to herbicides which inhibit cellulose biosynthesis, thus, interfere with cell wall biosynthesis.

BACKGROUND OF THE INVENTION

Microorganisms often respond to the input of xenobiotics into the environment by evolving mechanisms to use them as sources of nutrients and energy for their growth. As the structure of the herbicides based on a s-triazine ring differ from naturally occurring compounds (Esser et al. 1975), microorganisms slowly evolved enzymes and pathways capable of degrading them. The amidohydrolase superfamily comprises a remarkable set of enzymes that catalyze the hydrolysis of a wide range of substrates bearing amide or ester functional groups at carbon and phosphorus centers. In all cases, the nucleophilic water molecule is activated through complexation with a mononuclear or binuclear metal center. In the mononuclear metal centers, the substrate is activated by a proton transfer from the active site, and the water is activated by metal ligation and general base catalysis. The metal centers are perched at the C-terminal end of the beta-barrel core within a (beta alpha) 8 structural domain. One prominent example is the Atrazine chlorohydrolase (AtzA) an Fe(II)-dependent homohexamer (Seffernick et al. 2002; Wackett et al. 2002a) catalyzing the hydrolytic dechlorination of atrazine, a herbicide, yielding the nonherbicidal product 2-hydroxyatrazine (de Souza et al. 1996; Seffernick et al. 2002; Sadowsky and Wackett 2000). The closest known relative of AtzA is melamine deaminase (TriA from *Pseudomonas* sp. strain NRRL B-12227; 98% sequence identity). Despite their high sequence similarity, AtzA and TriA are catalytically distinct; TriA is a deaminase with a dechlorinase activity several orders below its physiological deaminase activity, while AtzA a dechlorinase with no detectable deaminase activity. Previous work has shown that three of the nine amino acids that differ between the two proteins (S331C; N328D; and F84I AtzA) are largely responsible for the differences in catalytic specificity.

The present invention provides new methods to increase herbicide tolerance in plants by the introduction of bacterial genes encoding target proteins that biodegrade the herbicide, in particular cellulose biosynthesis inhibitors named azines. The bacterial enzyme TriA was engineered in a form to remain or increase the amidohydrolase activity and to expand the enzyme pocket towards a more bulky substrate acceptance. The inventors of the present invention have surprisingly found that over-expression of wildtype or mutant melamine deaminase TriA forms confers in plants tolerance/resistance to particular classes of herbicides as compared to the non-transformed and/or non-mutagenized plants or plant cells, respectively. More specifically, the inventors of the present invention have found that TriA expression confers tolerance/resistance to azines.

The problem of the present invention can be seen as to the provision of novel traits by identifying target polypeptides, the manipulation of which makes plants tolerant to herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor.

The problem is solved by the subject-matter of the present invention.

SUMMARY OF THE INVENTION

Accordingly, in one aspect, the present invention provides a plant or plant part comprising a polynucleotide encoding a wildtype or mutated TriA polypeptide, the expression of said polynucleotide confers to the plant or plant part tolerance to herbicides.

In some aspects, the present invention provides a seed capable of germination into a plant comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In one aspect, the present invention provides a plant cell capable of regenerating a plant comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides, wherein the plant cell comprises the polynucleotide operably linked to a promoter.

In another aspect, the present invention provides a plant cell comprising a polynucleotide operably linked to a promoter operable in a cell, the promoter capable of expressing a wildtype or mutated TriA polypeptide encoded by the polynucleotide, the expression of the wildtype or mutated TriA polypeptide conferring to the plant tolerance to herbicides.

In other aspects, the present invention provides a plant product prepared from a plant or plant part comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In some aspects, the present invention provides a progeny or descendant plant derived from a plant comprising in at least some of its cells a polynucleotide operably linked to a promoter operable in plant cells, the promoter capable of expressing a wildtype or mutated TriA polypeptide encoded by the polynucleotide, wherein the progeny or descendant plant comprises in at least some of its cells the recombinant polynucleotide operably linked to the promoter, the expression of the wildtype or mutated TriA polypeptide conferring to the progeny or descendant plant tolerance to the herbicides.

In other aspects, the present invention provides a method for controlling weeds at a locus for growth of a plant, the method comprising: (a) applying an herbicide composition comprising herbicides to the locus; and (b) planting a seed at the locus, wherein the seed is capable of producing a plant that comprises in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In some aspects, the present invention provides a method for controlling weeds at a locus for growth of a plant, the method comprising: applying an herbicidal composition comprising herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In one aspect, step (a) occurs before, after, or concurrently with step (b).

In other aspects, the present invention provides a method of producing a plant having tolerance to herbicides, the method comprising regenerating a plant from a plant cell transformed with a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In one aspect, the present invention provides a method of producing a progeny plant having tolerance to herbicides, the method comprising: crossing a first herbicide-tolerant plant with a second plant to produce a herbicide-tolerant progeny plant, wherein the first plant and the progeny plant comprise in at least some of their cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

In addition, the present invention refers to a method for identifying a herbicide by using a wild-type or mutated TriA of the present invention encoded by a nucleic acid which comprises the nucleotide sequence of SEQ ID NO: 1, or a variant, homologue, paralogue or orthologue thereof.

Said method comprises the steps of:

a) generating a transgenic cell or plant comprising a nucleic acid encoding a mutated TriA of the present invention, wherein the mutated TriA of the present invention is expressed;
b) applying a herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a mutated TriA which is resistant or tolerant to a herbicide, the method comprising:

a) generating a library of mutated TriA-encoding nucleic acids,
b) screening a population of the resulting mutated TriA-encoding nucleic acids by expressing each of said nucleic acids in a cell or plant and treating said cell or plant with a herbicide,
c) comparing the herbicide-tolerance levels provided by said population of mutated TriA encoding nucleic acids with the herbicide-tolerance level provided by a control TriA-encoding nucleic acid,
d) selecting at least one mutated TriA-encoding nucleic acid that provides a significantly increased level of tolerance to a herbicide as compared to that provided by the control TriA-encoding nucleic acid.

In a preferred embodiment, the mutated TriA-encoding nucleic acid selected in step d) provides at least 2-fold as much tolerance to a herbicide as compared to that provided by the control TriA-encoding nucleic acid.

The resistance or tolerance can be determined by generating a transgenic plant comprising a nucleic acid sequence of the library of step a) and comparing said transgenic plant with a control plant.

Another object refers to an isolated, recombinant and/or chemically synthesized nucleic acid encoding a mutated TriA, the nucleic acid comprising the sequence of SEQ ID NO: 1, or a variant thereof, as defined hereinafter.

A preferred embodiment refers to an isolated and/or recombinantly produced and/or synthetic nucleic acid molecule comprising a nucleic acid molecule encoding a mutated TriA polypeptide selected from the group consisting of:

(a) a nucleic acid molecule encoding a mutated TriA polypeptide comprising the sequence of SEQ ID NO: 2, or a variant, paralogue, orthologue or homolog thereof;
(b) a nucleic acid molecule comprising the sequence of SEQ ID NO: 1, or a variant, paralogue, orthologue or homolog thereof;
(c) a nucleic acid molecule, which, as a result of the degeneracy of the genetic code, can be derived from a TriA polypeptide sequence of SEQ ID NO: 2, or a variant, paralogue, orthologue or homolog thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO:

1, or a variant, paralogue, orthologue or homolog thereof, and confers increased herbicide tolerance or resistance, as compared to a corresponding, e.g. non-transformed, wild type plant cell, a plant or a part thereof;

(e) a nucleic acid molecule encoding a mutated TriA polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the TriA polypeptide sequence of SEQ ID NO: 2, and confers increased herbicide tolerance or resistance, as compared to a corresponding, e.g. non-transformed, wild type plant cell, a plant or a part thereof;

(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;

wherein the amino acid sequence of the mutated TriA polypeptide differs from the wildtype amino acid sequence of a TriA polypeptide at one or more positions corresponding to the following positions of SEQ ID NO:2: 70, 71, 88, 91, 92, 96, 126, 128, 155, 157, 167, 220.

Another object refers to an expression cassette comprising the nucleic acid molecule of the present invention and a promoter operable in plant cells.

Preferably, the promoter is a root-specific promoter from *Glycine max*.

Another object refers to an isolated, recombinant and/or chemically synthesized mutated TriA polypeptide, the polypeptide comprising the sequence set forth in SEQ ID NO: 2, a variant, derivative, orthologue, paralogue or homologue thereof, as defined hereinafter.

Preferably, the amino acid sequence of the mutated TriA polypeptide differs from the wildtype amino acid sequence of a TriA polypeptide at one or more positions corresponding to the following positions of SEQ ID NO:2: 70, 71, 88, 91, 92, 96, 126, 128, 155, 157, 167, 220.

In still further aspects, the present invention provides a plant or plant part comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides, wherein the plant or plant part further exhibits a second or third herbicide-tolerant trait.

In another embodiment, the invention refers to a plant cell transformed by and expressing a wild-type or a mutated TriA nucleic acid according to the present invention or a plant which has been mutated to obtain a plant expressing, preferably over-expressing a wild-type or a mutated TriA nucleic acid according to the present invention, wherein expression of said nucleic acid in the plant cell results in increased resistance or tolerance to a herbicide as compared to a wild type variety of the plant cell In another embodiment, the invention refers to a plant comprising a plant cell according to the present invention, wherein expression of the nucleic acid in the plant results in the plant's increased resistance to herbicide as compared to a wild type variety of the plant.

Preferably, the expression of the nucleic acid of the invention in the plant results in the plant's increased resistance to herbicides as compared to a wild type variety of the plant.

In another embodiment, the invention refers to a seed produced by a transgenic plant comprising a plant cell of the present invention, wherein the seed is true breeding for an increased resistance to a herbicide as compared to a wild type variety of the seed.

In another embodiment, the invention refers to a method of producing a transgenic plant cell with an increased resistance to a herbicide as compared to a wild type variety of the plant cell comprising, transforming the plant cell with an expression cassette comprising a polynucleotide operably linked to a promoter operable in plant cells, the promoter capable of expressing a wildtype or mutated TriA polypeptide encoded by the polynucleotide. In another embodiment, the invention refers to a method of producing a transgenic plant comprising, (a) transforming a plant cell with an expression cassette comprising a polynucleotide operably linked to a promoter operable in plant cells, the promoter capable of expressing a wildtype or mutated TriA polypeptide encoded by the polynucleotide, and (b) generating a plant with an increased resistance to herbicide from the plant cell.

Preferably, the expression cassette further comprises a transcription initiation regulatory region and a translation initiation regulatory region that are functional in the plant.

DETAILED DESCRIPTION

Figure 1:
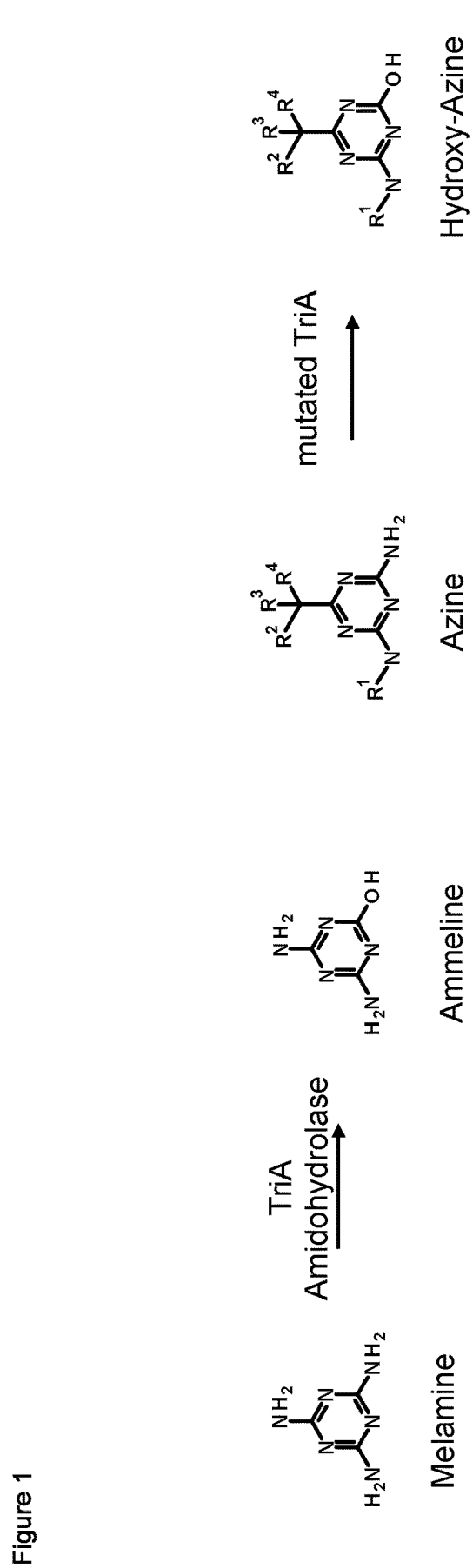
FIG. 1 shows the chemical reaction catalyzed by wildtype and mutated TriA amidohydrolase
Figure 2A:
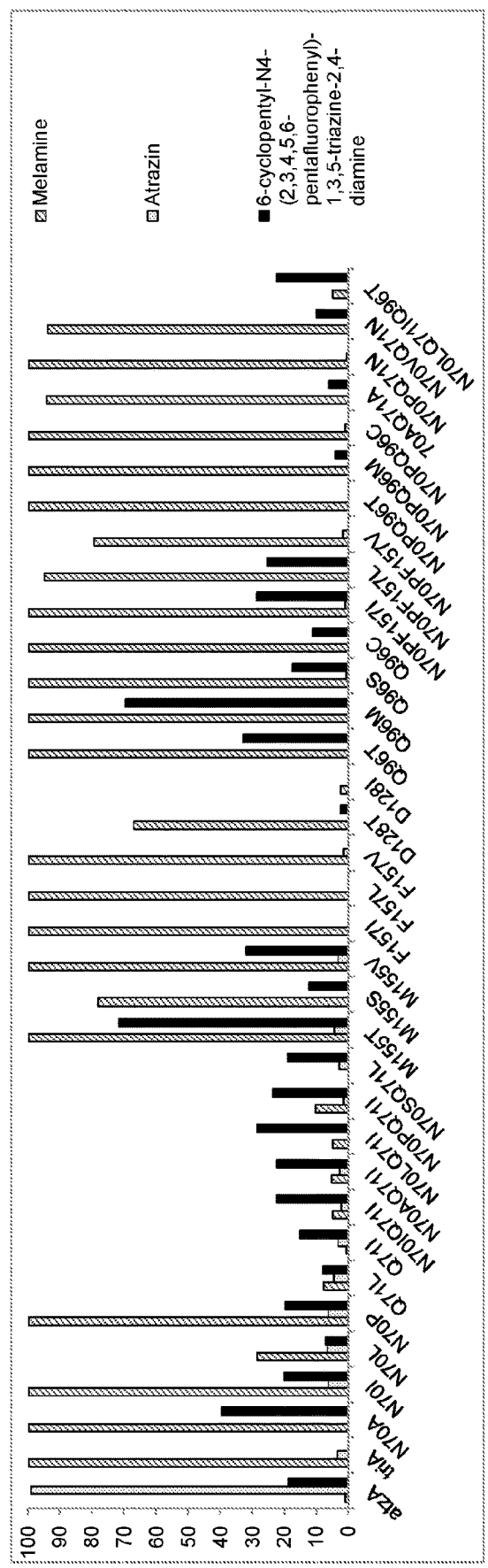
FIG. 2 shows degradation of selected azine, melamin & atrazine by triA-mutants
Figure 2B:
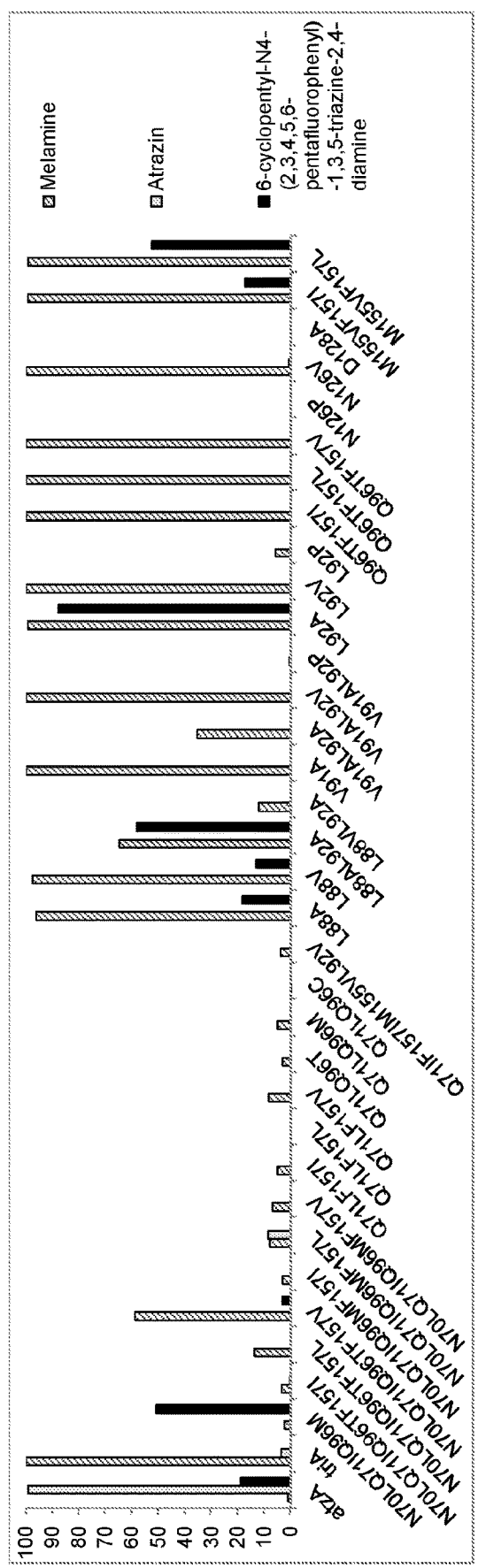

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The term "control of undesired vegetation or weeds" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, the herbicide treatments can be applied PPI (Pre Plant Incorporated), PPSA (Post plant surface applied), PRE- or POST-emergent. Postemergent treatment typically occurs to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wildtype plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide-tolerant and herbicide-tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. On the other hand, when used specifically in regard to a TriA enzyme, it refers specifically to the ability to metabolize, and thereby inactivate herbicides which inhibit cellulose biosynthesis, so-called cellulose biosynthesis inhibitors (CBI) By "herbicide-tolerant wildtype or mutated TriA protein" or "herbicide-resistant wildtype or mutated TriA protein", it is intended that such a TriA protein displays higher metabolizing activity, relative to the metabolizing activity of a wild-type TriA protein, when in the presence of at least one herbicide that is known to interfere with cellulose biosynthesis and at a concentration or level of the herbicide that is known to inhibit cellulose biosynthesis. Furthermore, the TriA activity of such a herbicide-tolerant or herbicide-resistant wildtype or mutated TriA protein may be referred to herein as "herbicide-tolerant" or "herbicide-resistant" TriA activity.

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

The term "transgenic plant" refers to a plant that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. In some embodiments, a "recombinant" organism is a "transgenic" organism. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Examples of human action that can be used to produce a mutagenized organism or DNA include, but are not limited to, treatment with a chemical mutagen such as EMS and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique.

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant). As used herein in regard to plants and other organisms, "recombinant," "transgenic," and "GMO" are considered synonyms and indicate the presence of genetic material from a different source; in contrast, "mutagenized" is used to refer to a plant or other organism, or the DNA thereof, in which no such transgenic material is present, but in which the native genetic material has become mutated so as to differ from a corresponding wild-type organism or DNA.

As used herein, "wild-type" or "corresponding wild-type plant" means the typical form of an organism or its genetic material, as it normally occurs, as distinguished from, e.g., mutagenized and/or recombinant forms. Similarly, by "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

As used herein, "descendant" refers to any generation plant. In some embodiments, a descendant is a first, second, third, fourth, fifth, sixth, seventh, eight, ninth, or tenth generation plant.

As used herein, "progeny" refers to a first generation plant.

The term "seed" comprises seeds of all types, such as, for example, true seeds, caryopses, achenes, fruits, tubers, seedlings and similar forms. In the context of *Brassica* and *Sinapis* species, "seed" refers to true seed(s) unless otherwise specified. For example, the seed can be seed of transgenic plants or plants obtained by traditional breeding methods. Examples of traditional breeding methods can include cross-breeding, selfing, back-crossing, embryo rescue, in-crossing, out-crossing, inbreeding, selection, asexual propagation, and other traditional techniques as are known in the art.

Although exemplified with reference to specific plants or plant varieties and their hybrids, in various embodiments, the presently described methods using herbicides can be employed with a variety of commercially valuable plants. Herbicide-tolerant plant lines described as useful herein can be employed in weed control methods either directly or indirectly, i.e. either as crops for herbicide treatment or as herbicide-tolerance trait donor lines for development, to produce other varietal and/or hybrid crops containing such trait or traits. All such resulting variety or hybrids crops, containing the ancestral herbicide-tolerance trait or traits can be referred to herein as progeny or descendant of the ancestral, herbicide-tolerant line(s). Such resulting plants can be said to retain the "herbicide tolerance characteristic(s)" of the ancestral plant, i.e. meaning that they possess and express the ancestral genetic molecular components responsible for the trait.

In one aspect, the present invention provides a plant or plant part comprising a polynucleotide encoding a wildtype or mutated TriA polypeptide, the expression of said polynucleotide confers to the plant or plant part tolerance to herbicides.

In a preferred embodiment, the plant has been previously produced by a process comprising recombinantly preparing a plant by introducing and over-expressing a wild-type or mutated TriA transgene according to the present invention, as described in greater detail hereinafter.

In another embodiment, the polynucleotide encoding the wildtype or mutated TriA polypeptide comprises the nucleic acid sequence set forth in SEQ ID NO: 1, or a variant or derivative thereof.

In other embodiments, the wildtype or mutated TriA polypeptide according to the present invention is a functional variant having, over the full-length of the variant, at least about 80%, illustratively, at least about 80%, 90%, 95%, 98%, 99% or more amino acid sequence identity to SEQ ID NO: 2.

In another embodiment, the wildtype or mutated TriA polypeptide for use according to the present invention is a functional fragment of a polypeptide having the amino acid sequence set forth in SEQ ID NO: 2.

It is recognized that the TriA polynucleotide molecules and TriA polypeptides of the invention encompass polynucleotide molecules and polypeptides comprising a nucleotide or an amino acid sequence that is sufficiently identical to nucleotide sequence set forth in SEQ ID Nos: 1, or to the amino acid sequence set forth in SEQ ID Nos: 2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated TriA nucleic acid" refers to a TriA nucleic acid having a sequence that is mutated from a wild-type TriA nucleic acid and that confers increased herbicide tolerance to a plant in which it is expressed. Furthermore, the term "mutated melamine deaminase (mutated TriA)" refers to the replacement of an amino acid of the wild-type primary sequence of SEQ ID NO: 2, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the TriA nucleotide sequence encoding a mutated TriA comprises the sequence of SEQ ID NO: 1, or a variant or derivative thereof Furthermore, it will be understood by the person skilled in the art that the TriA nucleotide sequences encompass homologues, paralogues and orthologues of SEQ ID NO: 1, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein comprising the sequence of SEQ ID NO: 2, as well as those that encode a polypeptide having amino acid substitutions relative to the native protein, e.g. the mutated TriA according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: 1. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the TriA polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 2.

By "variant" polypeptide is intended a polypeptide derived from the protein of SEQ ID NO: 2, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. Thus, functional variants and fragments of the TriA polypeptides, and nucleic acid molecules encoding them, also are within the scope of the present invention, and unless specifically described otherwise, irrespective of the origin of said polypeptide and irrespective of whether it occurs naturally. Various assays for functionality of a TriA polypeptide can be employed. For example, a functional variant or fragment of the TriA polypeptide can be assayed to determine its ability to confer herbicides detoxification.

By way of illustration, a herbicides detoxification rate can be defined as a catalytic rate sufficient to provide a determinable increase in tolerance to herbicides in a plant or plant part comprising a recombinant polynucleotide encoding the variant or fragment of the TriA polypeptide, wherein the plant or plant part expresses the variant or fragment at up to about 0.5%, illustratively, about 0.05 to about 0.5%, about 0.1 to about 0.4%, and about 0.2 to about 0.3%, of the total cellular protein relative to a similarly treated control plant that does not express the variant or fragment.

In a preferred embodiment, the wildtype or mutated TriA polypeptide is a functional variant or fragment of a melamine deaminase having the amino acid sequence set forth in SEQ ID NO: 2, wherein the functional variant or fragment has at least about 80% amino acid sequence identity to SEQ ID NO: 2.

In other embodiments, the functional variant or fragment further has a herbicides detoxification rate defined as a catalytic rate sufficient to provide a determinable increase in tolerance to herbicides in a plant or plant part comprising a recombinant polynucleotide encoding the variant or fragment, wherein the plant or plant part expresses the variant or fragment at up to about 0.5% of the total cellular protein to a similarly treated control plant that does not express the variant or fragment.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

In addition, one of ordinary skill in the art will further appreciate that changes can be introduced by mutation into the nucleotide sequences of the invention thereby leading to changes in the amino acid sequence of the encoded proteins without altering the biological activity of the proteins. Thus, for example, an isolated polynucleotide molecule encoding a mutated TriA polypeptide having an amino acid sequence that differs from that of SEQ ID NO: 2 can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention. For example, preferably, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid residue is required for biological activity.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W.H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Variants, orthologues and paralogues of SEQ ID NO:2 encompassed by the present invention are shown, but not limited to polypeptides comprising SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, or 31.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage (See FIG. 1). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The proteins of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. See, for example, Kunkel (1985) PNAS, 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D. C), herein incorporated by reference. Conservative substitutions, such as exchanging one amino acid with another having similar properties, may be preferable.

Alternatively, variant nucleotide sequences can be made by introducing mutations randomly along all or part of a coding sequence, such as by saturation mutagenesis, and the resultant mutants can be screened to identify mutants that encode proteins that retain activity. For example, following mutagenesis, the encoded protein can be expressed recombinantly, and the activity of the protein can be determined using standard assay techniques.

The inventors of the present invention have found that by substituting one or more of the key amino acid residues of the TriA enzyme of SEQ ID NO: 2, e.g. by employing one of the above described methods to mutate the TriA encoding nucleic acids, the tolerance or resistance to particular herbicides could be remarkably increased. Preferred substitutions of mutated TriA are those that increase the herbicide tolerance of the plant, but leave the biological activity of the deaminase activity substantially unaffected.

Accordingly, in another object of the present invention refers to a TriA polypeptide, comprising the sequence of SEQ ID NO: 2, a variant, derivative, orthologue, paralogue or homologue thereof, the key amino acid residues of which is substituted by any other amino acid.

It will be understood by the person skilled in the art that amino acids located in a close proximity to the positions of amino acids mentioned below may also be substituted. Thus, in another embodiment the variant of SEQ ID NO: 2, a variant, derivative, orthologue, paralogue or homologue thereof comprises a mutated TriA, wherein an amino acid±3, ±2 or ±1 amino acid positions from a key amino acid is substituted by any other amino acid.

Based on techniques well-known in the art, a highly characteristic sequence pattern can be developed, by means of which further of mutated TriA candidates with the desired activity may be searched.

Searching for further mutated TriA candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, e.g. saturation mutagenes (see e.g. Schenk et al., Biospektrum March 2006, pages 277-279), the inventors of the present invention have identified and generated specific amino acid substitutions and combinations thereof, which—when introduced into a plant by transforming and expressing the respective mutated TriA encoding nucleic acid—confer increased herbicide resistance or tolerance to a herbicide to said plant.

Thus, in a particularly preferred embodiment, the variant or derivative of the mutated TriA refers to a TriA polypeptide comprising SEQ ID NO:2, a orthologue, paralogue, or homologue thereof, wherein the amino acid sequence differs from the wildtype amino acid sequence of a TriA polypeptide at one or more positions corresponding to the following positions of SEQ ID NO:2:

70, 71, 88, 91, 92, 96, 126, 128, 155, 157, 167, 220.

Examples of differences at these amino acid positions include, but are not limited to, one or more of the following:

the amino acid corresponding to position 70 is other than Asparagine;

the amino acid corresponding to position 71 is other than Glutamine;

the amino acid corresponding to position 88 is other than Leucine;

the amino acid corresponding to position 91 is other than Valine, the amino acid corresponding to position 92 is other than Leucine, the amino acid corresponding to position 96 is other than Glutamine, the amino acid corresponding to position 126 is other than Asparagine;

the amino acid corresponding to position 128 is other than Aspartic Acid;

the amino acid corresponding to position 155 is other than Methionine;

the amino acid corresponding to position 157 is other than Phenylalanine, the amino acid corresponding to position 167 is other than Tyrosine, the amino acid corresponding to position 220 is other than Alanine, In some embodiments, the mutated TriA enzyme comprising SEQ ID NO: 2, a orthologue, paralogue, or homologue thereof, comprises one or more of the following:

In another preferred embodiment, the mutated TriA comprises a sequence of SEQ ID NO: 2 a variant, derivative, orthologue, paralogue of homologue thereof, in which:

the amino acid corresponding to position 70 is Ala, Ile, Leu, Pro.

In another preferred embodiment, the mutated TriA comprises a sequence of SEQ ID NO: 2 a variant, derivative, orthologue, paralogue of homologue thereof, in which:

the amino acid corresponding to position 71 is Leu, Ile.

In another preferred embodiment, the mutated TriA comprises a sequence of SEQ ID NO: 2 a variant, derivative, orthologue, paralogue of homologue thereof, in which:

the amino acid corresponding to position 70 is Ile, Ala, Leu, Pro, Ser, and the amino acid corresponding to position 71 is Leu, Ile.

In another preferred embodiment, the mutated TriA comprises a sequence of SEQ ID NO: 2 a variant, derivative, orthologue, paralogue of homologue thereof, in which:

the amino acid corresponding to position 70 is Ile, and the amino acid corresponding to position 71 is Leu.

In another preferred embodiment, the mutated TriA comprises a sequence of SEQ ID NO: 2 a variant, derivative, orthologue, paralogue of homologue thereof, in which:

the amino acid corresponding to position 70 is Ile, and the amino acid corresponding to position 71 is Ile.

In another preferred embodiment, the mutated TriA comprises a sequence of SEQ ID NO: 2 a variant, derivative, orthologue, paralogue of homologue thereof, in which:

the amino acid corresponding to position 70 is Ala, and the amino acid corresponding to position 71 is Leu.

In another preferred embodiment, the mutated TriA comprises a sequence of SEQ ID NO: 2 a variant, derivative, orthologue, paralogue of homologue thereof, in which:

the amino acid corresponding to position 70 is Ala, and the amino acid corresponding to position 71 is Ile.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Leu.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile.

In another preferred embodiment, the mutated TriA comprises a sequence of SEQ ID NO: 2 a variant, derivative, orthologue, paralogue of homologue thereof, in which:

the amino acid corresponding to position 70 is Pro, and the amino acid corresponding to position 71 is Leu.

In another preferred embodiment, the mutated TriA comprises a sequence of SEQ ID NO: 2 a variant, derivative, orthologue, paralogue of homologue thereof, in which:

the amino acid corresponding to position 70 is Pro, and the amino acid corresponding to position 71 is Ile.

In another preferred embodiment, the mutated TriA comprises a sequence of SEQ ID NO: 2 a variant, derivative, orthologue, paralogue of homologue thereof, in which:

the amino acid corresponding to position 70 is Ser, and the amino acid corresponding to position 71 is Leu.

In another preferred embodiment, the mutated TriA comprises a sequence of SEQ ID NO: 2 a variant, derivative, orthologue, paralogue of homologue thereof, in which:

the amino acid corresponding to position 70 is Ser, and the amino acid corresponding to position 71 is Ile.

In another preferred embodiment, the mutated TriA comprises a sequence of SEQ ID NO: 2 a variant, derivative, orthologue, paralogue of homologue thereof, in which:

the amino acid corresponding to position 155 is Thr, Ser, Val.

In another preferred embodiment, the mutated TriA comprises a sequence of SEQ ID NO: 2 a variant, derivative, orthologue, paralogue of homologue thereof, in which:

the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which:
the amino acid corresponding to position 128 is Thr, Ile.

In another preferred embodiment, the mutated TriA comprises a sequence of SEQ ID NO: 2 a variant, derivative, orthologue, paralogue of homologue thereof, in which:
the amino acid corresponding to position 96 is Thr, Met, Ser, Cys.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 157 is Ile.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 157 is Leu.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 157 is Val.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 96 is Thr, Met, Cys.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 96 is Thr.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 96 is Met.

In another preferred embodiment, the mutated TriA comprises a sequence of SEQ ID NO: 2 a variant, derivative, orthologue, paralogue of homologue thereof, in which:
the amino acid corresponding to position 70 is Pro, and the amino acid corresponding to position 96 is Cys.

In another preferred embodiment, the mutated TriA comprises a sequence of SEQ ID NO: 2 a variant, derivative, orthologue, paralogue of homologue thereof, in which:
the amino acid corresponding to position 70 is Ala, Pro, Val, and the amino acid corresponding to position 71 is Ala, Asn.

In another preferred embodiment, the mutated TriA comprises a sequence of SEQ ID NO: 2 a variant, derivative, orthologue, paralogue of homologue thereof, in which:

the amino acid corresponding to position 70 is Ala, and the amino acid corresponding to position 71 is Ala.

In another preferred embodiment, the mutated TriA comprises a sequence of SEQ ID NO: 2 a variant, derivative, orthologue, paralogue of homologue thereof, in which:

the amino acid corresponding to position 70 is Ala, and the amino acid corresponding to position 71 is Asn.

In another preferred embodiment, the mutated TriA comprises a sequence of SEQ ID NO: 2 a variant, derivative, orthologue, paralogue of homologue thereof, in which:

the amino acid corresponding to position 70 is Pro, and the amino acid corresponding to position 71 is Ala.

In another preferred embodiment, the mutated TriA comprises a sequence of SEQ ID NO: 2 a variant, derivative, orthologue, paralogue of homologue thereof, in which:

the amino acid corresponding to position 70 is Pro, and the amino acid corresponding to position 71 is Asn.

In another preferred embodiment, the mutated TriA comprises a sequence of SEQ ID NO: 2 a variant, derivative, orthologue, paralogue of homologue thereof, in which:

the amino acid corresponding to position 70 is Val, and the amino acid corresponding to position 71 is Ala.

In another preferred embodiment, the mutated TriA comprises a sequence of SEQ ID NO: 2 a variant, derivative, orthologue, paralogue of homologue thereof, in which:

the amino acid corresponding to position 70 is Val, and the amino acid corresponding to position 71 is Asn.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr, Met.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Met.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr, Met, and the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr, and the amino acid corresponding to position 157 is Ile.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr, and the amino acid corresponding to position 157 is Leu.

In another preferred embodiment, the mutated TriA comprises a sequence of SEQ ID NO: 2 a variant, derivative, orthologue, paralogue of homologue thereof, in which:

the amino acid corresponding to position 70 is Leu, and the amino acid corresponding to position 71 is Ile, and the amino acid corresponding to position 96 is Thr, and the amino acid corresponding to position 157 is Val.

In another preferred embodiment, the mutated TriA comprises a sequence of SEQ ID NO: 2 a variant, derivative, orthologue, paralogue of homologue thereof, in which: the amino acid corresponding to position 70 is Leu, and the amino acid corresponding to position 71 is Ile, and the amino acid corresponding to position 96 is Met, and the amino acid corresponding to position 157 is Ile.

In another preferred embodiment, the mutated TriA comprises a sequence of SEQ ID NO: 2 a variant, derivative, orthologue, paralogue of homologue thereof, in which: the amino acid corresponding to position 70 is Leu, and the amino acid corresponding to position 71 is Ile, and the amino acid corresponding to position 96 is Met, and the amino acid corresponding to position 157 is Leu.

In another preferred embodiment, the mutated TriA comprises a sequence of SEQ ID NO: 2 a variant, derivative, orthologue, paralogue of homologue thereof, in which: the amino acid corresponding to position 70 is Leu, and the amino acid corresponding to position 71 is Ile, and the amino acid corresponding to position 96 is Met, and the amino acid corresponding to position 157 is Val.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 157 is Ile.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 157 is Leu.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 157 is Val.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 96 is Thr, Met, Cys.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 96 is Thr.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 96 is Met.

In another preferred embodiment, the mutated TriA comprises a sequence of SEQ ID NO: 2 a variant, derivative, orthologue, paralogue of homologue thereof, in which: the amino acid corresponding to position 71 is Leu, and the amino acid corresponding to position 96 is Cys.

In another preferred embodiment, the mutated TriA comprises a sequence of SEQ ID NO: 2 a variant, derivative, orthologue, paralogue of homologue thereof, in which: the amino acid corresponding to position 71 is Ile, and the amino acid corresponding to position 157 is Ile, and the amino acid corresponding to position 155 is Val, and the amino acid corresponding to position 92 is Val.

In another preferred embodiment, the mutated TriA comprises a sequence of SEQ ID NO: 2 a variant, derivative, orthologue, paralogue of homologue thereof, in which: the amino acid corresponding to position 71 is Ile, and the amino acid corresponding to position 157 is Ile, and the amino acid corresponding to position 155 is Val, and the amino acid corresponding to position 92 is Val.

In another preferred embodiment, the mutated TriA comprises a sequence of SEQ ID NO: 2 a variant, derivative, orthologue, paralogue of homologue thereof, in which: the amino acid corresponding to position 88 is Ala, Val.

In another preferred embodiment, the mutated TriA comprises a sequence of SEQ ID NO: 2 a variant, derivative, orthologue, paralogue of homologue thereof, in which: the amino acid corresponding to position 88 is Ala, Val, and the amino acid corresponding to position 92 is Ala.

In another preferred embodiment, the mutated TriA comprises a sequence of SEQ ID NO: 2 a variant, derivative, orthologue, paralogue of homologue thereof, in which: the amino acid corresponding to position 88 is Ala, and the amino acid corresponding to position 92 is Ala.

In another preferred embodiment, the mutated TriA comprises a sequence of SEQ ID NO: 2 a variant, derivative, orthologue, paralogue of homologue thereof, in which: the amino acid corresponding to position 88 is Val, and the amino acid corresponding to position 92 is Ala.

In another preferred embodiment, the mutated TriA comprises a sequence of SEQ ID NO: 2 a variant, derivative, orthologue, paralogue of homologue thereof, in which: the amino acid corresponding to position 91 is Ala.

In another preferred embodiment, the mutated TriA comprises a sequence of SEQ ID NO: 2 a variant, derivative, orthologue, paralogue of homologue thereof, in which: the amino acid corresponding to position 91 is Ala, and the amino acid corresponding to position 92 is Ala, Val, Pro.

In another preferred embodiment, the mutated TriA comprises a sequence of SEQ ID NO: 2 a variant, derivative, orthologue, paralogue of homologue thereof, in which: the amino acid corresponding to position 91 is Ala, and the amino acid corresponding to position 92 is Ala.

In another preferred embodiment, the mutated TriA comprises a sequence of SEQ ID NO: 2 a variant, derivative, orthologue, paralogue of homologue thereof, in which: the amino acid corresponding to position 91 is Ala, and the amino acid corresponding to position 92 is Val.

In another preferred embodiment, the mutated TriA comprises a sequence of SEQ ID NO: 2 a variant, derivative, orthologue, paralogue of homologue thereof, in which: the amino acid corresponding to position 91 is Ala, and the amino acid corresponding to position 92 is Pro.

In another preferred embodiment, the mutated TriA comprises a sequence of SEQ ID NO: 2 a variant, derivative, orthologue, paralogue of homologue thereof, in which: the amino acid corresponding to position 92 is Ala, Val, Pro.

In another preferred embodiment, the mutated TriA comprises a sequence of SEQ ID NO: 2 a variant, derivative, orthologue, paralogue of homologue thereof, in which: the amino acid corresponding to position 96 is Thr, and the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which:

the amino acid corresponding to position 96 is Thr, and the amino acid corresponding to position 157 is Ile.

In another preferred embodiment, the mutated TriA comprises a sequence of SEQ ID NO: 2 a variant, derivative, orthologue, paralogue of homologue thereof, in which: the amino acid corresponding to position 96 is Thr, and the amino acid corresponding to position 157 is Leu.

In another preferred embodiment, the mutated TriA comprises a sequence of SEQ ID NO: 2 a variant, derivative, orthologue, paralogue of homologue thereof, in which: the amino acid corresponding to position 96 is Thr, and the amino acid corresponding to position 157 is Val.

In another preferred embodiment, the mutated TriA comprises a sequence of SEQ ID NO: 2 a variant, derivative, orthologue, paralogue of homologue thereof, in which: the amino acid corresponding to position 126 is Pro, Val.

In another preferred embodiment, the mutated TriA comprises a sequence of SEQ ID NO: 2 a variant, derivative, orthologue, paralogue of homologue thereof, in which: the amino acid corresponding to position 128 is Ala.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 157 is Ile, Leu, Val.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 157 is Ile.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 157 is Leu.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 157 is Val.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 70 is Pro.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 71 is Leu.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 96 is Thr, Met, Cys.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 96 is Thr.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 96 is Met.

In another preferred embodiment, the mutated TriA comprises a sequence of SEQ ID NO: 2 a variant, derivative, orthologue, paralogue of homologue thereof, in which: the amino acid corresponding to position 155 is Val, and the amino acid corresponding to position 96 is Cys.

In another preferred embodiment, the mutated TriA comprises a sequence of SEQ ID NO: 2 a variant, derivative, orthologue, paralogue of homologue thereof, in which: the amino acid corresponding to position 167 is Ser.

In another preferred embodiment, the mutated TriA comprises a sequence of SEQ ID NO: 2 a variant, derivative, orthologue, paralogue of homologue thereof, in which: the amino acid corresponding to position 220 is Gly.

It will be within the knowledge of the skilled artisan to identify conserved regions and motifs shared between the homologues, orthologues and paralogues encoded by SEQ ID NO: 1. Having identified such conserved regions that may represent suitable binding motifs, amino acids can be chosen to be substituted by any other amino acid, for example by conserved amino acids, preferably by the amino acid substitutions described SUPRA using SEQ ID NO:2 as reference.

Another object refers to a method of identifying a nucleotide sequence encoding a mutated TriA which is resistant or tolerant to a herbicide, the method comprising:
a) generating a library of mutated TriA-encoding nucleic acids,
b) screening a population of the resulting mutated TriA-encoding nucleic acids by expressing each of said nucleic acids in a cell or plant and treating said cell or plant with a herbicide,
c) comparing the herbicide-tolerance levels provided by said population of mutated TriA encoding nucleic acids with the herbicide-tolerance level provided by a control TriA-encoding nucleic acid,
d) selecting at least one mutated TriA-encoding nucleic acid that provides a significantly increased level of tolerance to a herbicide as compared to that provided by the control TriA-encoding nucleic acid.

Herbicide-tolerance levels may also be determined by measuring the detoxification rate in a cell, tissue, or plant.

Detoxification rate is the rate of herbicide degradation within a certain timeframe in a respective tissue. The degradation and product formation can be determined analytically for instance by liquid chromatographie (LC) coupled to a high resolution (HR) mass spectrometer (MS). Product can be determined by comparison to authentic standards and/or by structure elucidation.

In a preferred embodiment, the mutated TriA-encoding nucleic acid selected in step d) provides at least 2-fold as much resistance or tolerance of a cell or plant to a herbicide as compared to that provided by the control TriA-encoding nucleic acid.

In a further preferred embodiment, the mutated TriA-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a herbicide as compared to that provided by the control TriA-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Many methods well known to the skilled artisan are available for obtaining suitable candidate nucleic acids for identifying a nucleotide sequence encoding a mutated TriA from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mutated TriA-encoding sequences.

Nucleic acids comprising candidate and control TriA encoding sequences can be expressed in yeast, in a bacterial host strain, in an alga or in a higher plant such as tobacco or *Arabidopsis* and the relative levels of inherent tolerance of the TriA encoding sequences screened according to a visible indicator phenotype of the transformed strain or plant in the presence of different concentrations of the selected herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed TriA. For example, in a relatively rapid assay system based upon transformation of a bacterium such as *E. coli*, each mutated TriA encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different TriA sequences. Such strains expressing nucleic acids comprising alternative candidate TriA sequences may be plated out on different concentrations of the selected herbicide in, optionally, a tyrosine supplemented medium and the relative levels of inherent tolerance of the expressed TriA enzymes estimated on the basis of the extent and MIC for inhibition of the formation of the brown, ochronotic pigment, or by measuring the herbicide degradation via LC-HRMS (liquid chromatography high resolution mass spectrometry).

In another embodiment, candidate nucleic acids are transformed into plant material to generate a transgenic plant, regenerated into morphologically normal fertile plants which are then measured for differential tolerance to selected herbicides as described in the Example section hereinafter. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control TriA. The average, and distribution, of herbicide tolerance levels of a range of primary plant transformation events or their progeny to herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed TriA. Herbicides can suitably be applied pre-emergence or post-emergence.

Another object of the present invention refers to an isolated, recombinant and/or chemically synthesized nucleic acid encoding a mutated TriA as disclosed SUPRA, wherein the nucleic acid comprises the nucleotide sequence of SEQ ID NO: 1, or a variant or derivative thereof.

In a preferred embodiment, the encoded mutated TriA is a variant of SEQ ID NO:2, which includes one or more of the following:
the amino acid corresponding to position 70 is other than Asparagine;
the amino acid corresponding to position 71 is other than Glutamine;
the amino acid corresponding to position 88 is other than Leucine;
the amino acid corresponding to position 91 is other than Valine,
the amino acid corresponding to position 92 is other than Leucine,
the amino acid corresponding to position 96 is other than Glutamine,
the amino acid corresponding to position 126 is other than Asparagine;
the amino acid corresponding to position 128 is other than Aspartic Acid;
the amino acid corresponding to position 155 is other than Methionine;
the amino acid corresponding to position 157 is other than Phenylalanine,
the amino acid corresponding to position 167 is other than Tyrosine,
the amino acid corresponding to position 220 is other than Alanine, In other aspects, the present invention encompasses a progeny or a descendant of a herbicide-tolerant plant of the present invention as well as seeds derived from the herbicide-tolerant plants of the invention and cells derived from the herbicide-tolerant plants of the invention.

In some embodiments, the present invention provides a progeny or descendant plant derived from a plant comprising in at least some of its cells a polynucleotide operably linked to a promoter operable in plant cells, the promoter capable of expressing a wildtype or mutated TriA polypeptide encoded by the polynucleotide, wherein the progeny or descendant plant comprises in at least some of its cells the recombinant polynucleotide operably linked to the promoter, the expression of the wildtype or mutated TriA polypeptide conferring to the progeny or descendant plant tolerance to the herbicides.

In one embodiment, seeds of the present invention preferably comprise the herbicide-tolerance characteristics of the herbicide-tolerant plant. In other embodiments, a seed is capable of germination into a plant comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the progeny or descendant plant tolerance to the herbicides.

In some embodiments, plant cells of the present invention are capable of regenerating a plant or plant part. In other embodiments, plant cells are not capable of regenerating a plant or plant part. Examples of cells not capable of regenerating a plant include, but are not limited to, endosperm, seed coat (testa & pericarp), and root cap.

In another embodiment, the present invention provides a plant cell of or capable of regenerating a plant comprising in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to the herbicides, wherein the plant cell comprises the recombinant polynucleotide operably linked to a promoter.

In other embodiments, the present invention provides a plant cell comprising a polynucleotide operably linked to a promoter operable in plant cells, the promoter capable of expressing a wildtype or mutated TriA polypeptide encoded by the polynucleotide, the expression of the wildtype or mutated TriA polypeptide conferring to the cell tolerance to the herbicides.

In another embodiment, the invention refers to a plant cell transformed by a nucleic acid encoding a mutated TriA polypeptide according to the present invention, wherein expression of the nucleic acid in the plant cell results in increased resistance or tolerance to a herbicide as compared to a wild type variety of the plant cell. Preferably, the mutated TriA polypeptide encoding nucleic acid comprises a polynucleotide sequence selected from the group consisting of: a) a polynucleotide as shown in SEQ ID NO: 1, or a variant or derivative thereof; b) a polynucleotide encoding a polypeptide as shown in SEQ ID NO: 2, or a variant or derivative thereof; c) a polynucleotide comprising at least 60 consecutive nucleotides of any of a) or b); and d) a polynucleotide complementary to the polynucleotide of any of a) through c).

In some aspects, the present invention provides a plant product prepared from the herbicide-tolerant plants hereof. In some embodiments, examples of plant products include, without limitation, grain, oil, and meal. In one embodiment, a plant product is plant grain (e.g., grain suitable for use as feed or for processing), plant oil (e.g., oil suitable for use as food or biodiesel), or plant meal (e.g., meal suitable for use as feed).

In one embodiment, a plant product prepared from a plant or plant part is provided, wherein the plant or plant part comprises in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the a plant or plant part tolerance to the herbicides.

In another embodiment, the invention refers to a method of producing a transgenic plant cell with an increased resistance to a herbicide as compared to a wild type variety of the plant cell comprising, transforming the plant cell with an expression cassette comprising a polynucleotide operably linked to a promoter operable in plant cells, the promoter capable of expressing a wildtype or mutated TriA polypeptide encoded by the polynucleotide.

In another embodiment, the invention refers to a method of producing a transgenic plant comprising, (a) transforming a plant cell with an expression cassette comprising a polynucleotide operably linked to a promoter operable in plant cells, the promoter capable of expressing a wildtype or mutated TriA polypeptide encoded by the polynucleotide, and (b) generating a plant with an increased resistance to herbicide from the plant cell.

In some aspects, the present invention provides a method for producing a herbicide-tolerant plant. In one embodiment, the method comprises: regenerating a plant from a plant cell transformed with a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to the herbicides.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the herbicide derivative herbicide of the present invention, it will be understood that the at least one nucleic acid is "over-expressed" by methods and means known to the person skilled in the art.

The term "increased expression" or "overexpression" as used herein means any form of expression that is additional to the wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene. An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Where appropriate, nucleic acid sequences may be optimized for increased expression in a transformed plant. For example, coding sequences that comprise plant-preferred codons for improved expression in a plant can be provided. See, for example, Campbell and Gowri (1990) Plant Physiol., 92: 1-11 for a discussion of host-preferred codon usage. Methods also are known in the art for preparing plant-preferred genes. See, for example, U.S. Pat. Nos. 5,380,831, and 5,436,391, and Murray et al. (1989) Nucleic Acids Res. 17:477-498, herein incorporated by reference.

Consequently, wildtype/mutated TriA nucleic acids of the invention are provided in expression cassettes for expression in the plant of interest. The cassette will include regulatory sequences operably linked to a mutated TriA nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the wildtype/mutated TriA nucleic acid sequence to be under the transcriptional regulation of the regulatory regions. The expression cassette may additionally contain selectable marker genes. The expression cassette of the present invention will include in the 5'-3' direction of transcription, a transcriptional and translational initiation region (i.e., a promoter), a wildtype/mutated TriA encoding nucleic acid sequence of the invention, and a transcriptional and translational termination region (i.e., termination region) functional in plants. The promoter may be native or analogous, or foreign or heterologous, to the plant host and/or to the wildtype/mutated TriA nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the wildtype/mutated TriA nucleic acid sequence of the invention, it is intended that the promoter is not the native or naturally occurring promoter for the operably linked wildtype/mutated TriA nucleic acid sequence of the invention. As used herein, a chimeric gene comprises a coding sequence operably linked to a transcription initiation region that is heterologous to the coding sequence. While it may be preferable to express the wildtype/mutated TriA nucleic acids of the invention using heterologous promoters, the native promoter sequences may be used. Such constructs would change expression levels of the wildtype/mutated TriA protein in the plant or plant cell. Thus, the phenotype of the plant or plant cell is altered.

The termination region may be native with the transcriptional initiation region, may be native with the operably linked wildtype/mutated TriA sequence of interest, may be native with the plant host, or may be derived from another source (i.e., foreign or heterologous to the promoter, the wildtype/mutated TriA nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Thus, the present invention provides an expression cassette comprising a wildtype/mutated TriA nucleic acid nucleic acid molecule according to the present invention and a promoter operable in plant cells.

In a preferred embodiment, the promoter is a root specific promoter.

In a particularly preferred embodiment, the promoter is a root specific promoter from *Glycine max*. (e.g. p-Glyma04g34080, see Examples 8 and 9)

Even more preferably, the promoter comprises the nucleic acid sequence of SEQ ID NO: 32.

While the polynucleotides of the invention may find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

Further, additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. Also, if desired, sequences can be readily modified to avoid predicted hairpin secondary mRNA structures. Nucleotide sequences for enhancing gene expression can also be used in the plant expression vectors. These include, for example, introns of the maize Adh gene Adh1-S intron 1, 2, and 6 (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize gene expression, the plant expression vectors of the invention also may contain DNA sequences containing matrix attachment regions (MARs). Plant cells transformed with such modified expression systems, then, may exhibit overexpression or constitutive expression of a nucleotide sequence of the invention.

The invention further provides an isolated recombinant expression vector comprising the expression cassette containing a wildtype/mutated TriA nucleic acid nucleic acid as described above, wherein expression of the vector in a host cell results in increased tolerance to a herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated TriA polypeptides, fusion polypeptides, etc.)

Expression vectors may additionally contain 5' leader sequences in the expression construct. Such leader sequences can act to enhance translation. Translation leaders are known in the art and include: picornavirus leaders, for example, EMCV leader (Encephalomyo carditis 5' noncoding region) (Elroy-Stein et al. (1989) PNAS, 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

Other methods known to enhance translation also can be utilized, for example, introns, and the like. In preparing an expression vector, the various nucleic acid fragments may be manipulated, so as to provide for the nucleic acid sequences in the proper orientation and, as appropriate, in the proper reading frame. Toward this end, adapters or linkers may be employed to join the nucleic acid fragments or other manipulations may be involved to provide for convenient restriction sites, removal of superfluous nucleic acid, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular plant tissue. Such tissue-preferred promoters include, but are not limited to, leaf-preferred promoters, root-preferred promoters, seed-preferred promoters, and stem-preferred promoters. Some examples of tissue-preferred promoters are described by, e.g., Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al.

(1997) Transgenic Res. 6(2): 157-168; Rinehart et al. (1996) Plant Physiol. 1 12(3): 1331-1341; Van Camp et al. (1996) Plant Physiol. 112(2):525-535; Canevascini et al. (1996) Plant Physiol. 1 12(2):513-524; Yamamoto et al. (1994) Plant Cell Physiol. 35(5):773-778; Lam (1994) Results Probl. Cell Differ. 20:181-196; Orozco of al. (1993) Plant Mol Biol. 23(6): 1 129-1138; Matsuoka et al. (1993) Voc Natl. Acad. ScL USA 90(20):9586-9590; and Guevara-Garcia et al. (1993) Plant J 4(3):495-505. Promoters can be modified, if necessary, for weak expression.

In a preferred embodiment, the promoter is a root-specific promoter.

In a particularly preferred embodiment, the promoter comprises the nucleic acid sequence of SEQ ID NO: 32.

In some embodiments, the nucleic acids of interest can be targeted to the chloroplast for expression. In this manner, where the nucleic acid of interest is not directly inserted into the chloroplast, the expression vector will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the desired coding sequence of the invention such that the two sequences are contiguous and in the same reading frame. See, for example, Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481. For example, a chloroplast transit peptide known in the art can be fused to the amino acid sequence of a TriA polypeptide of the invention by operably linking a choloroplast-targeting sequence to the 5'-end of a nucleotide sequence encoding the TriA polypeptide.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J Biol. Chem. 266(5):3335-3342); EPSPS (Archer et al. (1990) J Bioenerg. Biomemb. 22(6):789-810); tryptophan synthase (Zhao et al. (1995) J Biol. Chem. 270(11):6081-6087); plastocyanin (Lawrence et al. (1997) J Biol. Chem. 272(33):20357-20363); chorismate synthase (Schmidt et al. (1993) J Biol. Chem. 268(36):27447-27457); and the light harvesting chlorophyll a/b binding protein (LHBP) (Lamppa et al. (1988) J Biol. Chem. 263: 14996-14999). See also Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Numerous plant transformation vectors and methods for transforming plants are available. See, for example, An, G. et al. (1986) Plant PysioL, 81:301-305; Fry, J., et al. (1987) Plant Cell Rep. 6:321-325; Block, M. (1988) Theor. Appl. Genet 0.16: 161-1 1 A; Hinchee, et al. (1990) Stadler. Genet. Symp. 2032\2.203-2\2; Cousins, et al. (1991) Aust. J. Plant Physiol. 18:481-494; Chee, P. P. and Slightom, J. L. (1992) Gene. II 8:255-260; Christou, et al. (1992) Trends. Biotechnol. 10:239-246; Halluin, et al. (1992) Bio/Technol. 10:309-314; Dhir, et al. (1992) Plant Physiol. 99:81-88; Casas et al. (1993) Proc. Nat. Acad Sd. USA 90: 1 1212-1 1216; Christou, P. (1993) In Vitro Cell. Dev. Biol.-Plant; 29P. 119-124; Davies, et al. (1993) Plant Cell Rep. 12: 180-183; Dong, J. A. and Mchughen, A. (1993) Plant ScL 91: 139-148; Franklin, C. I. and Trieu, T. N. (1993) Plant. Physiol. 102: 167; Golovkin, et al. (1993) Plant ScL 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

In some embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The term "introduction" or "transformation" as referred to herein further means the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

By "stable transformation" is intended that the polynucleotide construct introduced into a plant integrates into the genome of the plant and is capable of being inherited by descendent thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, the encoding nucleotide sequence is operably linked to a plant promoter, e.g. a promoter known in the art for high-level expression in a plant cell, and this construct is then introduced into a plant cell that is susceptible to herbicides; and a transformed plant is regenerated. In some embodiments, the transformed plant is tolerant to exposure to a level of herbicides that would kill or significantly injure a plant regenerated from an untransformed cell. This method can be applied to any plant species or crops.

Methodologies for constructing plant expression vectors and introducing foreign nucleic acids into plants are generally known in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang eta (1991) Gene 100: 247-250; Scheid et al. al, (1991) MoL Gen. Genet., 228: 104-1 12; Guerche et al., (1987) Plant Science 52: 111-116; Neuhause et al., (1987) Theor. Appl Genet. 75: 30-36; Klein et al., (1987) Nature 327: 70-73; Howell et al., (1980) Science 208: 1265; Horsch et al., (1985) Science 227: 1229-1231; DeBlock et al., (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, eds.) Academic Press, Inc. (1989).

Other suitable methods of introducing nucleotide sequences into plant cells include microinjection as described by, e.g., Crossway et al. (1986) Biotechniques 4:320-334, electroporation as described by e.g., Riggs et al. (1986) Proc. Natl. Acad. ScL USA 83:5602-5606, *Agrobacterium*-mediated transformation as described by e.g., Townsend et al., U.S. Pat. No. 5,563,055, Zhao et al., U.S. Pat. No. 5,981,840, direct gene transfer as described by, e.g., Paszkowski et al. (1984) EMBO J. 3:2717-2722, and ballistic particle acceleration as described by, e.g., U.S. Pat. Nos. 4,945,050; 5,879,918; 5,886,244; and 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6:923-926); and Led transformation (WO 00/28058). Also see, Weissinger et al., (1988) Ann. Rev. Genet. 22:421-477; Sanford et al, (1987) Particulate Science and Technology 5:27-37 (onion); Christou et al, (1988) Plant Physiol. 87:671-674 (soybean); McCabe et al., (1988) Bio/Technology 6:923-926 (soybean); Finer and McMullen (1991) In Vitro Cell Dev. Biol. 27P: 175-182 (soybean); Singh et al, (1998) Theor. Appl. Genet. 96:319-324 (soybean); Datta et al., (1990) Biotechnology 8:736-740 (rice); Klein et al., (1988) PNAS, 85:4305-4309 (maize); Klein et al., (1988) Biotechnology 6:559-563 (maize); U.S. Pat. Nos. 5,240,855; 5,322,783; and 5,324,646; Tomes et al., (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al., (1988) Plant Physiol. 91:440-444 (maize); Fromm et al., (1990) Biotechnology 8:833-839 (maize); Hooykaas-Van Slogteren et al., (1984) Nature (London) 31 1:763-764; Bowen et al, U.S. Pat. No. 5,736,369 (cereals); Bytebier et al, (1987) PNAS 84:5345-5349 (Liliaceae); De Wet et al., (1985) in The Experimental Manipulation of Ovule Tissues, ed. Chapman et al, (Longman, New York), pp. 197-209 (pollen); Kaeppler et al., (1990) Plant Cell Reports 9:415-418 and Kaeppler et al., (1992) Theor. Apph Genet. 84:560-566 (whisker-mediated transformation); D'Halluin et al., (1992) Plant Cell 4: 1495-1505 (electroporation); Li et al., (1993) Plant Cell Reports 12:250-255 and Christou and Ford (1995) Annals of Botany 75:407-413 (rice); Osjoda et al, (1996) Nature Biotechnology 14:745-750 (maize via *Agrobacterium tumefaciens*); each of which is herein incorporated by reference.

Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

One transformation method known to those of skill in the art is the dipping of a flowering plant into an Agrobacteria solution, wherein the Agrobacteria contains the TriA nucleic acid, followed by breeding of the transformed gametes. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

In some embodiments, polynucleotides of the present invention may be introduced into plants by contacting plants with a virus or viral nucleic acids. Generally, such methods involve incorporating a polynucleotide construct of the invention within a viral DNA or RNA molecule. It is recognized that the polypeptides of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference. The cells that have been transformed may be grown into plants in accordance with conventional ways. See, for example, McCormick et a (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. raps, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet e.g., pearl millet (*Pennisetum glaucum*), proso millet (*Panicum miliaceum*), foxtail millet (*Setaria italica*), finger millet (*Eleusine coracana*)), sunflower (*Helianthus annu*), safflower (*Carthamus tinctorius*), wheat (*Triticum aestivum, T. Turgidum* ssp. *durum*), soybean (*Glycine max*), tobacco (*Nicotiana tabacum*), potato (*Solarium tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the expression of the nucleic acid in the plant results in the plant's increased resistance to herbicide as compared to a wild type variety of the plant.

In another embodiment, the invention refers to a plant, comprising a plant cell according to the present invention, wherein expression of the nucleic acid in the plant results in the plant's increased resistance to herbicide as compared to a wild type variety of the plant.

The plants described herein can be either transgenic crop plants or non-transgenic plants.

In addition to the general definition, give SUPRA, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated TriA of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a TriA gene of the plant or seed.

The herbicide-resistant plants of the invention that comprise polynucleotides encoding mutated TriA polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated TriA polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant.

The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In another embodiment, the invention refers to a seed produced by a transgenic plant comprising a plant cell of the present invention, wherein the seed is true breeding for an increased resistance to a herbicide as compared to a wild type variety of the seed.

In other aspects, herbicide-tolerant plants of the present invention can be employed as herbicide-tolerance trait donor lines for development, as by traditional plant breeding, to produce other varietal and/or hybrid crops containing such trait or traits. All such resulting variety or hybrids crops, containing the ancestral herbicide-tolerance trait or traits can be referred to herein as progeny or descendant of the ancestral, herbicide-tolerant line(s).

In other embodiments, the present invention provides a method for producing a herbicide-tolerant plant. The method comprises: crossing a first herbicide-tolerant plant with a second plant to produce a herbicide-tolerant progeny plant, wherein the first plant and the progeny plant comprise in at least some of their cells a polynucleotide operably linked to a promoter operable in plant cells, the recombinant polynucleotide being effective in the cells of the first plant to express a wildtype or mutated TriA polypeptide encoded by the polynucleotide, the expression of the wildtype or mutated TriA polypeptide conferring to the plant tolerance to herbicides.

Traditional plant breeding might be employed whereby the herbicide-tolerant trait is introduced in the progeny plant resulting therefrom. In one embodiment, the present invention provides a method for producing a herbicide-tolerant progeny plant, the method comprising: crossing a parent plant with a herbicide-tolerant plant to introduce the herbicide-tolerance characteristics of the herbicide-tolerant plant into the germplasm of the progeny plant, wherein the progeny plant has increased tolerance to the herbicides relative to the parent plant. In other embodiments, the method further comprises the step of introgressing the herbicide-tolerance characteristics through traditional plant breeding techniques to obtain a descendent plant having the herbicide-tolerance characteristics.

In other aspects, plants of the invention include those plants which, in addition to being tolerant to herbicides inhibiting cellulose biosynthesis, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, herbicide-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, herbicide-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other cellulose biosynthesis inhibitors; and to GS inhibitors, such as glufosinate.

In addition to these classes of inhibitors, herbicide-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity. Herbicide-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, herbicide-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB (b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the herbicide-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes* bicolor); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis; the rape winter stem weevil Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil

*Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha; the American spider beetle Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *psylla Cacopsylla pyricola*; the currant aphid *Cryptomyzus ribis*; the grape *phylloxera Daktulosphaira vitifoliae*; the citrus *psylla Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco *thrips Frankliniella fusca*, the flower *thrips Frankliniella intonsa*, the western flower *thrips Frankliniella occidentalism* the cotton bud *thrips Frankliniella schultzei*, the banded greenhouse *thrips Hercinothrips femoralis*, the soybean *thrips Neohydatothrips variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the herbicide-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the herbicide-tolerant plants is effective for controlling cabbage seedpod weevil, the Bertha armyworm, *Lygus* bugs, or the diamondback moth.

Furthermore, in one embodiment, herbicide-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, herbicide-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, herbicide-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, herbicide-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, herbicide-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate(glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, herbicide-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, herbicide-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epi-taxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

In other aspects, a method for treating a plant of the present invention is provided.

In some embodiments, the method comprises contacting the plant with an agronomically acceptable composition. In one embodiment, the agronomically acceptable composition comprises an auxinic herbicide A. I.

In another embodiment, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a herbicides herbicidal composition to the descendent plant.

In another embodiment, the invention refers to harvestable parts of the transgenic plant according to the present invention. Preferably, the harvestable parts comprise the TriA nucleic acid or TriA protein of the present invention. The harvestable parts may be seeds, roots, leaves and/or flowers comprising the TriA nucleic acid or TriA protein or parts thereof. Preferred parts of soy plants are soy beans comprising the TriA nucleic acid or TriA protein.

In another embodiment, the invention refers to products derived from a transgenic plant according to the present invention, parts thereof or harvestable parts thereof. A preferred plant product is fodder, seed meal, oil, or seed-treatment-coated seeds. Preferably, the meal and/or oil comprise the TriA nucleic acids or TriA proteins.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Herbicides

As described above, the present invention provides nucleic acids, polypeptides, conferring tolerance of plants to compounds/herbicides interfering or inhibiting cell wall (cellulose) biosynthesis.

Examples of herbicides which can be used according to the present invention, i.e. to which the plants according to the present invention are tolerant/resistant to, are compounds known to the skilled artisan as azines. Examples of Azines are described in detail in the following patent applications depicted in the following Table 1, which are incorporated by reference in its entirety

TABLE 1

| Structural Formula | Application number/Internal reference; publication number |
|---|---|
| 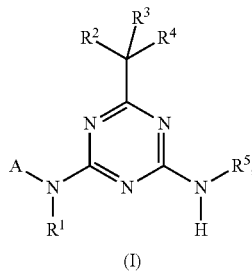 (I) | PCT/EP2014/065092 PF75365; WO2015/007711 |
| 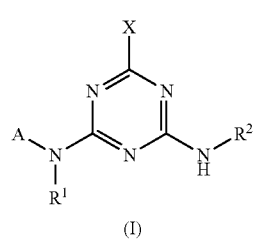 (I) | EP 14162309.0 PF76068; WO2015/144881 |

TABLE 1-continued

| Structural Formula | Application number/Internal reference; publication number |
|---|---|
| (Structure with X, triazine, A-N(R¹)-, -NH-R²) (I) | EP 14163356.0 PF76069; WO2015/150541 |
| (Structure with X, triazine, A-N(R¹)-, -NH-R²) (I) | EP 14163742.1 PF76635; WO2015/155129 |
| (Structure with X, triazine, A-N(R¹)-, -NH-R²) (I) | EP 14163743.9 PF76636; EP2930174 |
| (Structure with (Ar—Q)$_p$, phenyl with R$^a$, (R$^b$)$_q$, triazine with X, N(R¹), NHR²) | EP 14165565.4 PF76857; WO2015/162166 |
| (Structure with (R$^b$)$_q$, A ring, triazine with X, N(R¹), NHR²) | EP 14165624.9 PF76888; WO2015/162169 |
| (Structure with R$^a$, R$^b$, R$^c$, R$^d$, F-phenyl, R$^5$-C(R³)-R⁴, triazine, N(R¹), NHR²) | EP 14164431.0 PF76890; WO2015/155271 |
| (Structure with R$^a$, (R$^b$)$_q$, F-phenyl, R$^5$-C(R³)-R⁴, triazine, N(R¹), NHR²) | EP 14164434.4 PF76930; WO2015/155272 |
| (Structure with R³—O—C(R⁴)(R⁵)-, triazine, A-N(R¹)-, -NH-R²) (I) | EP 14164433.6 PF77027; WO2015/155273 |

Examples of preferred herbicides which can be used according to the present invention are azines having the Formula (I).

$$I$$

(Structure: R²-C(R³)(R⁴)- attached to triazine, with A-N(R¹)- and -N(H)-R⁵)

wherein
A is phenyl, which is substituted by two to five substituents selected from the group consisting of halogen, CN, NO$_2$, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;

R¹ H, CN, C$_1$-C$_6$-alkyl, C$_1$-C$_6$-haloalkyl, C$_1$-C$_6$-alkoxy-C$_1$-C$_6$-alkyl, C$_1$-C$_6$-alkoxy, (C$_1$-C$_6$-alkyl)carbonyl, (C$_1$-C$_6$-alkoxy)carbonyl, (C$_1$-C$_6$-alkyl)sulfonyl or phenylsulfonyl,
wherein the phenyl is unsubstituted or substituted by one to five substituents selected from the group consisting of halogen, CN, NO$_2$, C$_1$-C$_6$-alkyl, C$_1$-C$_6$-haloalkyl and C$_1$-C$_6$-alkoxy;

R² H, halogen, CN, C$_1$-C$_6$-alkyl, C$_1$-C$_6$-haloalkyl, C$_2$-C$_6$-alkenyl, C$_3$-C$_6$-alkynyl, C$_3$-C$_6$-cycloalkyl, C$_3$-C$_6$-cycloalkenyl, OH, C$_1$-C$_6$-alkoxy or C$_1$-C$_6$-alkoxy-C$_1$-C$_6$-alkyl;

R³ H, halogen, CN, C$_1$-C$_6$-alkyl, C$_1$-C$_6$-haloalkyl or C$_1$-C$_6$-alkoxy;

R⁴ H, halogen, CN, C$_1$-C$_6$-alkyl or C$_1$-C$_6$-haloalkyl; or

R³ and R⁴ together with the carbon atom to which they are attached form a moiety selected from the group consisting of carbonyl, C$_2$-C$_6$-alkenyl, C$_3$-C$_6$-cycloalkyl, C$_3$-C$_6$-cycloalkenyl and three- to six-membered heterocyclyl,
wherein the C$_3$-C$_6$-cycloalkyl, C$_3$-C$_6$-cycloalkenyl, or three- to six-membered heterocyclyl is unsubstituted or substituted by one to three substituents selected from halogen, CN, C$_1$-C$_6$-alkyl and C$_1$-C$_6$-alkoxy; and R⁵ H, CN, C$_1$-C$_6$-alkyl, C$_1$-C$_6$-haloalkyl, C$_1$-C$_6$-alkoxy-C$_1$-C$_6$-alkyl, C$_1$-C$_6$-alkoxy, (C$_1$-C$_6$-alkyl)carbonyl, (C$_1$-C$_6$-alkoxy)carbonyl, (C$_1$-C$_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Preferably the present invention provides azines of formula (I), wherein

A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)-carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or and three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Useful for the present invention are also agrochemical compositions comprising at least one azines of formula (I) and auxiliaries customary for formulating crop protection agents.

The present invention also provides the use of azines of formula (I) as herbicides, i.e. for controlling harmful plants.

If the azines of formula (I) as described herein are capable of forming geometrical isomers, for example E/Z isomers, it is possible to use both, the pure isomers and mixtures thereof, in the compositions according to the invention.

If the azines of formula (I) as described herein have one or more centres of chirality and, as a consequence, are present as enantiomers or diastereomers, it is possible to use both, the pure enantiomers and diastereomers and their mixtures, in the compositions according to the invention.

If the azines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The organic moieties mentioned in the definition of the variables, e.g. $R^1$ to $R^5$, are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfinyl, alkylsulfonyl, (alkyl)amino, di(alkyl)amino chains can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$, n-butyl, $CH(CH_3)$—$C_2H_5$, $CH_2$—CH$(CH_3)_2$ and $C(CH_3)_3$;

$C_1$-$C_6$-alkyl and also the $C_1$-$C_6$-alkyl moieties of ($C_1$-$C_6$-alkyl)carbonyl, $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, $C_1$-$C_6$-alkoxy-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methyl-propoxy and 1-ethyl-2-methylpropoxy.

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentylsulfinyl, 1-methylbutylsulfinyl, 2-methyl butylsulfinyl, 3-methylbutylsulfinyl, 2,2-dimethylpropylsulfinyl, 1-ethylpropylsulfinyl, 1,1-dimethyl-propylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutyl-sulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methyl butylsulfonyl, 3-methyl butylsulfonyl, 1,1-dimethylpropylsulfonyl, 1,2-di-methylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentyl-sulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3- dimethylbutylsulfonyl, 1-ethylbutylsulfonyl, 2-ethylbutylsulfonyl, 1,1,2-trimethyl-propylsulfonyl, 1,2,2-tri methyl propylsulfonyl, 1-ethyl-1-methylpropylsulfonyl and 1-ethyl-2-methylpropylsulfonyl;

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl) amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl) amino, N-methyl-N-(1-ethylpropyl)amino, N-methyl-N-hexylamino, N-methyl-N-(1,1-dimethylpropyl) amino, N-methyl-N-(1,2-dimethylpropyl)amino, N-methyl-N-(1-methylpentyl)amino, N-methyl-N-(2-methylpentyl)amino, N-methyl-N-(3-methylpentyl) amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethyl-butyl)amino, N-methyl-N-(2,3-dimethylbutyl)amino, N-methyl-N-(3,3-dimethylbutyl)amino, N-methyl-N-(1-ethylbutyl) amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl) amino, N-ethyl-N-(3-methylbutyl)amino, N-ethyl-N-(2,2-dimethylpropyl)amino, N-ethyl-N-(1-ethylpropyl) amino, N-ethyl-N-hexylamino, N-ethyl-N-(1,1-dimethylpropyl)amino, N-ethyl-N-(1,2-dimethylpropyl)-amino, N-ethyl-N-(1-methylpentyl) amino, N-ethyl-N-(2-methylpentyl)amino, N-ethyl-N-(3-methylpentyl)amino, N-ethyl-N-(4-methylpentyl) amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl) amino, N-ethyl-N-(2,3-dimethylbutyl)amino, N-ethyl-N-(3,3-dimethylbutyl)amino, N-ethyl-N-(1-ethylbutyl) amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

three- to six-membered heterocyclyl: monocyclic saturated or partially unsaturated hydrocarbon having three to six ring members as mentioned above which, in addition to carbon atoms, contains one or two heteroatoms selected from O, S and N;

for example 2-oxiranyl, 2-oxetanyl, 3-oxetanyl, 2-aziridinyl, 3-thietanyl, 1-azetidinyl, 2-azetidinyl, for example 2-tetrahydrofuranyl, 3-tetrahydrofuranyl, 2-tetrahydrothienyl, 3-tetra-hydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl;

for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-di-hydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4- dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

The preferred embodiments of the invention mentioned herein below have to be understood as being preferred either independently from each other or in combination with one another.

According to a preferred embodiment of the invention preference is also given to those azines of formula (I), wherein the variables, either independently of one another or in combination with one another, have the following meanings:

Preferred are the azines of formula (I), wherein

A is phenyl, which is substituted by two to five substituents
selected from the group consisting of halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred phenyl, which is substituted by two to five substituents
selected from the group consisting of halogen, CN, $C_1$-$C_6$-alkyl and $C_1$-$C_6$-alkoxy;
particularly preferred selected from halogen and CN;
also particularly preferred selected from the group consisting of F, Cl, CN and CH$_3$;
especially preferred selected from the group consisting of F, Cl and CN;
especially preferred phenyl, which is substituted by two to four substituents
selected from the group consisting of halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and CH$_3$;
more preferred selected from the group consisting of F, Cl and CN;
more preferred phenyl, which is substituted by two substituents
selected from the group consisting of halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and CH$_3$;
more preferred selected from the group consisting of F, Cl and CN;
also more preferred phenyl, which is substituted by three substituents
selected from the group consisting of halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and CH$_3$;
more preferred selected from the group consisting of F, Cl and CN;
also more preferred phenyl, which is substituted by four substituents
selected from the group consisting of halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and CH$_3$;
more preferred selected from the group consisting of F, Cl and CN.

Also preferred are the azines of formula (I), wherein

A is

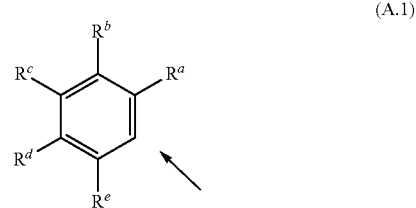

(A.1)

wherein $R^a$ and $R^e$ independently of one another are halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl; and $R^b$, $R^c$ and $R^d$ independently of one another are hydrogen, halogen, CN, NO$_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another are halogen or CN; and $R^b$, $R^c$ and $R^d$ independently of one another are hydrogen, halogen, CN, $C_1$-$C_6$-alkyl or $C_1$-$C_6$-alkoxy;

more preferred $R^a$ and $R^e$ are halogen; and $R^b$, $R^c$ and $R^d$ independently of one another are hydrogen, halogen or CN;

most preferred $R^a$ and $R^e$ are halogen; and $R^b$, $R^c$ and $R^d$ are hydrogen;

also most preferred $R^a$, $R^b$, $R^d$ and $R^e$ are halogen; and $R^c$ hydrogen;

also most preferred $R^a$, $R^b$, $R^c$, $R^d$ and $R^e$ are halogen.

Also preferred are the azines of formula (I), wherein A is

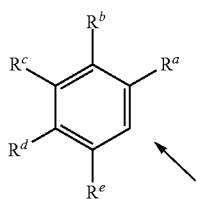

(A.1)

wherein $R^a$ is halogen or CN;

$R^b$ and $R^d$ are H, halogen or CN;

$R^c$ is H or halogen;

$R^e$ is halogen, CN or $C_1$-$C_6$-alkyl;

particularly preferred $R^a$ is halogen;

$R^b$, $R^c$ and $R^d$ are H or halogen; and $R^e$ is halogen or CN;

especially preferred $R^a$, $R^b$, $R^d$ and $R^e$ are halogen; and $R^c$ is H or halogen;

more preferred $R^a$, $R^b$, $R^d$ and $R^e$ are F; and $R^c$ is H or F.

Especially preferred are the azines of formula (I), wherein A is selected from the group consisting of (A.1.1), (A.1.2) and (A.1.3);

more preferred selected from the group consisting of (A.1.2) and (A.1.3);

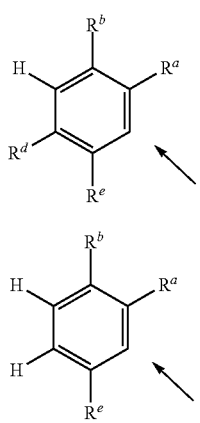

(A.1.1)

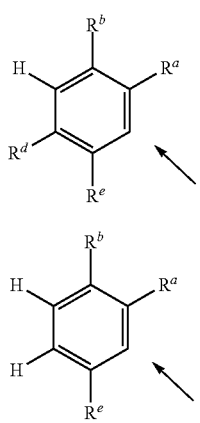

(A.1.2)

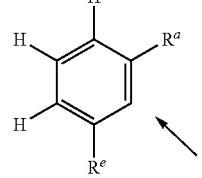

(A.1.3)

wherein $R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl; and $R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$ and $R^d$ independently of one another are halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another halogen or CN; and $R^b$ and $R^d$ independently of one another are halogen, CN, $C_1$-$C_6$-alkyl or $C_1$-$C_6$-alkoxy;

more preferred $R^a$ and $R^e$ are halogen; and $R^b$ and $R^d$ independently of one another are halogen or CN;

most preferred $R^a$, $R^b$, $R^d$ and $R^e$ are halogen.

Also especially preferred are the azines of formula (I), wherein
A is

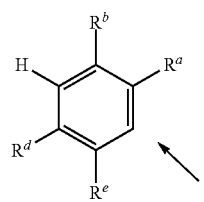

(A.1.1)

wherein $R^a$, $R^b$, $R^d$ and $R^e$ have the meanings, in particular the preferred meanings, as defined above.

Also especially preferred are the azines of formula (I), wherein
A is

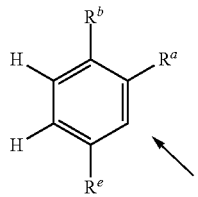

(A.1.2)

wherein $R^a$, $R^b$ and $R^e$ have the meanings, in particular the preferred meanings, as defined above.

Also especially preferred are the azines of formula (I), wherein
A is

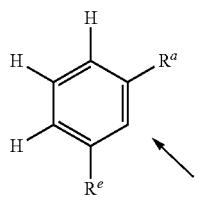

(A.1.3)

wherein $R^a$ and $R^e$ have the meanings, in particular the preferred meanings, as defined above.

Also preferred are the azines of formula (I), wherein
A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;
 particularly preferred 2-fluoro-phenyl, which is substituted by one to four substituents selected from the group consisting of halogen, CN, $C_1$-$C_6$-alkyl and $C_1$-$C_6$-alkoxy;
 particularly preferred selected from halogen and CN;
 also particularly preferred selected from the group consisting of F, Cl, CN and $CH_3$;
 especially preferred selected from the group consisting of F, Cl and CN;
 especially preferred 2-fluoro-phenyl, which is substituted by one to three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
 particularly preferred selected from the group consisting of halogen, CN, $C_1$-$C_6$-alkyl and $C_1$-$C_6$-alkoxy;
 especially preferred selected from halogen and CN;
 also especially preferred selected from the group consisting of F, Cl, CN and $CH_3$;
 more preferred selected from the group consisting of F, Cl and CN;
 more preferred 2-fluoro-phenyl, which is substituted by one substituent selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
 particularly preferred selected from the group consisting of halogen, CN, $C_1$-$C_6$-alkyl and $C_1$-$C_6$-alkoxy;
 especially preferred selected from halogen and CN;
 also especially preferred selected from the group consisting of F, Cl, CN and $CH_3$;
 more preferred selected from the group consisting of F, Cl and CN;
 also more preferred 2-fluoro-phenyl, which is substituted by two substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
 particularly preferred selected from the group consisting of halogen, CN, $C_1$-$C_6$-alkyl and $C_1$-$C_6$-alkoxy;
 especially preferred selected from halogen and CN;
 also especially preferred selected from the group consisting of F, Cl, CN and $CH_3$;
 more preferred selected from the group consisting of F, Cl and CN;
 also more preferred 2-fluoro-phenyl, which is substituted by three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
 particularly preferred selected from the group consisting of halogen, CN, $C_1$-$C_6$-alkyl and $C_1$-$C_6$-alkoxy;
 especially preferred selected from halogen and CN;
 also especially preferred selected from the group consisting of F, Cl, CN and $CH_3$;
 more preferred selected from the group consisting of F, Cl and CN.

Also preferred are the azines of formula (I), wherein
A is

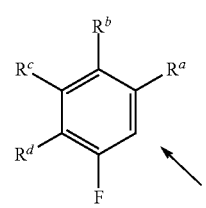

(A.1a)

wherein
$R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$, $R^c$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred $R^a$ is halogen, CN, $C_1$-$C_6$-alkyl or $C_1$-$C_6$-alkoxy; and $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;
especially preferred $R^a$ is halogen or CN; and
$R^b$, $R^c$ and $R^d$ independently of one another are hydrogen, halogen, CN, $C_1$-$C_6$-alkyl or $C_1$-$C_6$-alkoxy;
more preferred $R^a$ is halogen; and
$R^b$, $R^c$ and $R^d$ independently of one another are hydrogen, halogen or CN;
most preferred $R^a$ is halogen; and
$R^b$, $R^c$ and $R^d$ are hydrogen;
also most preferred $R^a$, $R^b$ and $R^d$ are halogen; and
$R^c$ is hydrogen;
also most preferred $R^a$, $R^b$, $R^c$ and $R^d$ are halogen.

Also preferred are the azines of formula (I), wherein A is

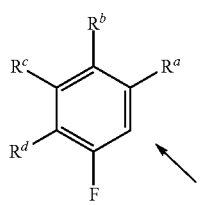

(A.1a)

wherein $R^a$ is halogen, CN or $C_1$-$C_6$-alkyl;
$R^b$ and $R^d$ are H, halogen or CN; and
$R^c$ is H or halogen;
particularly preferred $R^a$ is halogen or CN; and
$R^b$, $R^c$ and $R^d$ are H or halogen;
especially preferred $R^a$, $R^b$ and $R^d$ are halogen; and
$R^c$ is H or halogen;
Also especially preferred $R^a$, $R^b$ and $R^d$ are halogen; and
$R^c$ is H, F, Br or I;
more preferred $R^a$, $R^b$ and $R^d$ are F; and
$R^c$ is F, Br or I;
also more preferred $R^a$, $R^b$ and $R^d$ are F; and
$R^c$ is H or F.

Especially preferred are the azines of formula (I), wherein A is selected from the group consisting of (A.1a.1), (A.1a.2) and (A.1a.3);
more preferred selected from the group consisting of (A.1.2) and (A.1.3);

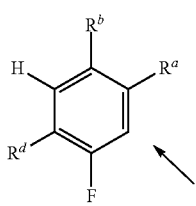

(A.1a.1)

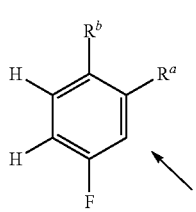

(A.1a.2)

-continued

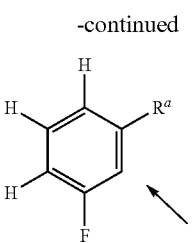

(A.1a.3)

wherein
$R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred $R^a$ is halogen, CN, $C_1$-$C_6$-alkyl or $C_1$-$C_6$-alkoxy; and
$R^b$ and $R^d$ independently of one another are halogen, CN, $NO_2$, $C_1$-$C_6$-alkyl, $C_1$-$C_6$-haloalkyl or $C_1$-$C_6$-alkoxy;
especially preferred $R^a$ is halogen or CN; and
$R^b$ and $R^d$ independently of one another are halogen, CN, $C_1$-$C_6$-alkyl or $C_1$-$C_6$-alkoxy;
more preferred $R^a$ is halogen; and
$R^b$ and $R^d$ independently of one another are halogen or CN;
most preferred $R^a$, $R^b$ and $R^d$ are halogen.

Also especially preferred are the azines of formula (I), wherein A is

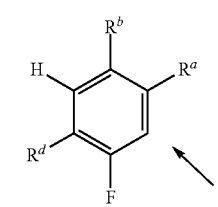

(A.1a.1)

wherein $R^a$, $R^b$ and $R^d$ have the meanings, in particular the preferred meanings, as defined above.

Also especially preferred are the azines of formula (I), wherein A is

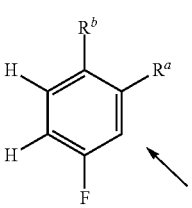

(A.1a.2)

wherein $R^a$ and $R^b$ have the meanings, in particular the preferred meanings, as defined above.

Also especially preferred are the azines of formula (I), wherein
A is

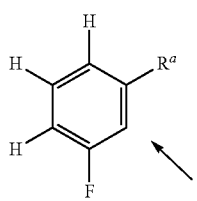

(A.1a.3)

wherein $R^a$ has the meanings, in particular the preferred meanings, as defined above.

Also preferred are the azines of formula (I), wherein
$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$;
more preferred hydrogen.

Also preferred are the azines of formula (I), wherein
$R^2$ is H, halogen, $C_1$-$C_6$-alkyl or $C_1$-$C_6$-haloalkyl;
particularly preferred halogen, $C_1$-$C_6$-alkyl or $C_1$-$C_6$-haloalkyl;
also particularly preferred H, F, Cl, $CH_3$ or $CF_3$.

Also preferred are the azines of formula (I), wherein
$R^3$ and $R^4$ are
independently of one another H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
independently of one another particularly preferred H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl,
wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
independently of one another especially preferred H, halogen, $C_1$-$C_6$-alkyl or $C_1$-$C_6$-haloalkyl;
independently of one another more preferred H, halogen or $C_1$-$C_6$-alkyl.

Also preferred are the azines of formula (I), wherein
$R^2$ is H, halogen, $C_1$-$C_6$-alkyl; and
$R^3$ and $R^4$ are independently of one another H, $C_1$-$C_6$-alkyl, or together with the carbon atom to which they are attached form a $C_3$-$C_6$-cycloalkyl;
particularly preferred $R^2$ is H, halogen or $C_1$-$C_6$-alkyl;
$R^3$ is $C_1$-$C_6$-alkyl;
$R^4$ is H, halogen or $C_1$-$C_6$-alkyl;
$R^3$ and $R^4$ together with the carbon atom to which they are attached form a $C_3$-$C_6$-cycloalkyl;
especially preferred $R^2$ is halogen or $C_1$-$C_6$-alkyl;
$R^3$ is $C_1$-$C_6$-alkyl;
$R^4$ is H or $C_1$-$C_6$-alkyl;
more preferred $R^2$ is halogen; and
$R^3$ and $R^4$ are $C_1$-$C_6$-alkyl.

Also preferred are the azines of formula (I), wherein
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$; more preferred hydrogen.

Also preferred are the azines of formula (I), wherein
A is phenyl, which is substituted by two to five substituents
selected from the group consisting of halogen, CN, $C_1$-$C_6$-alkyl and $C_1$-$C_6$-alkoxy;
particularly preferred selected from halogen and CN;
also particularly preferred selected from the group consisting of F, Cl, CN and $CH_3$;
especially preferred selected from the group consisting of F, Cl and CN;
particularly preferred phenyl, which is substituted by two to four substituents
selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
especially preferred phenyl, which is substituted by two substituents
selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
also especially preferred phenyl, which is substituted by three substituents
selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;

also especially preferred selected from the group consisting of F, Cl, CN and $CH_3$;
more preferred selected from the group consisting of F, Cl and CN;
also specially preferred phenyl, which is substituted by four substituents
selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
particularly preferred selected from the group consisting of halogen, CN, $C_1$-$C_6$-alkyl and $C_1$-$C_6$-alkoxy;
especially preferred selected from halogen and CN;
also especially preferred selected from the group consisting of F, Cl, CN and $CH_3$;
more preferred selected from the group consisting of F, Cl and CN;
$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$; more preferred hydrogen.
$R^2$ is H, halogen, $C_1$-$C_6$-alkyl or $C_1$-$C_6$-haloalkyl;
particularly preferred halogen, $C_1$-$C_6$-alkyl or $C_1$-$C_6$-haloalkyl;
also particularly preferred H, F, $CH_3$ or $CF_3$;
$R^3$ and $R^4$ are independently of one another H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
independently of one another particularly preferred H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl,
wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
independently of one another especially preferred H, halogen, $C_1$-$C_6$-alkyl or $C_1$-$C_6$-haloalkyl;
independently of one another more preferred H, halogen or $C_1$-$C_6$-alkyl; and
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$; more preferred hydrogen.
Particular preference is given to azines of formula (I.a), which correspond to azines of formula (I) wherein A is (A.1) and $R^1$ and $R^5$ are H:

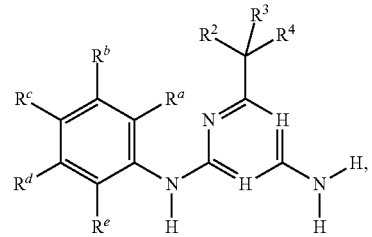

wherein the variables $R^a$, $R^b$, $R^c$, $R^d$, $R^e$, $R^2$, $R^3$ and $R^4$ have the meanings, in particular the preferred meanings, as defined above;

special preference is given to the azines of the formulae (I.a.1) to (I.a.1406) of Table A, where the definitions of the variables $R^a$, $R^b$, $R^c$, $R^d$, $R^e$, $R^2$, $R^3$ and $R^4$ are of particular importance for the compounds according to the invention not only in combination with one another but in each case also on their own:

TABLE A

| No. | $R^a$ | $R^b$ | $R^c$ | $R^d$ | $R^e$ | $R^2$ | $R^3$ | $R^4$ |
|---|---|---|---|---|---|---|---|---|
| I.a.1 | F | H | H | H | F | $CH_3$ | H | H |
| I.a.2 | Cl | H | H | H | F | $CH_3$ | H | H |
| I.a.3 | Br | H | H | H | F | $CH_3$ | H | H |
| I.a.4 | CN | H | H | H | F | $CH_3$ | H | H |
| I.a.5 | $CH_3$ | H | H | H | F | $CH_3$ | H | H |
| I.a.6 | F | H | H | F | F | $CH_3$ | H | H |
| I.a.7 | Cl | H | H | F | F | $CH_3$ | H | H |
| I.a.8 | F | H | H | Cl | F | $CH_3$ | H | H |
| I.a.9 | Cl | H | H | F | F | $CH_3$ | H | H |
| I.a.10 | CN | H | H | F | F | $CH_3$ | H | H |
| I.a.11 | F | H | H | CN | F | $CH_3$ | H | H |
| I.a.12 | CN | H | H | F | F | $CH_3$ | H | H |
| I.a.13 | F | H | F | H | F | $CH_3$ | H | H |
| I.a.14 | Cl | H | F | H | F | $CH_3$ | H | H |
| I.a.15 | CN | H | F | H | F | $CH_3$ | H | H |
| I.a.16 | F | F | F | H | F | $CH_3$ | H | H |
| I.a.17 | Cl | F | F | H | F | $CH_3$ | H | H |
| I.a.18 | F | Cl | F | H | F | $CH_3$ | H | H |
| I.a.19 | Cl | F | F | H | F | $CH_3$ | H | H |
| I.a.20 | CN | F | F | H | F | $CH_3$ | H | H |
| I.a.21 | F | CN | F | H | F | $CH_3$ | H | H |
| I.a.22 | CN | F | F | H | F | $CH_3$ | H | H |
| I.a.23 | F | F | H | F | F | $CH_3$ | H | H |
| I.a.24 | Cl | F | H | F | F | $CH_3$ | H | H |
| I.a.25 | F | Cl | H | F | F | $CH_3$ | H | H |
| I.a.26 | CN | F | H | F | F | $CH_3$ | H | H |
| I.a.27 | F | CN | H | F | F | $CH_3$ | H | H |
| I.a.28 | F | F | F | F | F | $CH_3$ | H | H |
| I.a.29 | Cl | F | F | F | F | $CH_3$ | H | H |
| I.a.30 | F | Cl | F | F | F | $CH_3$ | H | H |
| I.a.31 | CN | F | F | F | F | $CH_3$ | H | H |
| I.a.32 | F | CN | F | F | F | $CH_3$ | H | H |
| I.a.33 | H | F | F | F | F | $CH_3$ | H | H |
| I.a.34 | F | F | Br | F | F | $CH_3$ | H | H |
| I.a.35 | F | F | C≡CH | F | F | $CH_3$ | H | H |
| I.a.36 | $CF_3$ | Cl | H | H | F | $CH_3$ | H | H |
| I.a.37 | F | F | I | F | F | $CH_3$ | H | H |
| I.a.38 | F | H | H | H | F | $CH_3$ | $CH_3$ | H |
| I.a.39 | Cl | H | H | H | F | $CH_3$ | $CH_3$ | H |
| I.a.40 | Br | H | H | H | F | $CH_3$ | $CH_3$ | H |
| I.a.41 | CN | H | H | H | F | $CH_3$ | $CH_3$ | H |
| I.a.42 | $CH_3$ | H | H | H | F | $CH_3$ | $CH_3$ | H |
| I.a.43 | F | H | H | F | F | $CH_3$ | $CH_3$ | H |
| I.a.44 | Cl | H | H | F | F | $CH_3$ | $CH_3$ | H |
| I.a.45 | F | H | H | Cl | F | $CH_3$ | $CH_3$ | H |
| I.a.46 | Cl | H | H | F | F | $CH_3$ | $CH_3$ | H |
| I.a.47 | CN | H | H | F | F | $CH_3$ | $CH_3$ | H |
| I.a.48 | F | H | H | CN | F | $CH_3$ | $CH_3$ | H |
| I.a.49 | CN | H | H | F | F | $CH_3$ | $CH_3$ | H |
| I.a.50 | F | H | F | H | F | $CH_3$ | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.51 | Cl | H | F | H | F | $CH_3$ | $CH_3$ | H |
| I.a.52 | CN | H | F | H | F | $CH_3$ | $CH_3$ | H |
| I.a.53 | F | F | F | H | F | $CH_3$ | $CH_3$ | H |
| I.a.54 | Cl | F | F | H | F | $CH_3$ | $CH_3$ | H |
| I.a.55 | F | Cl | F | H | F | $CH_3$ | $CH_3$ | H |
| I.a.56 | Cl | F | F | H | F | $CH_3$ | $CH_3$ | H |
| I.a.57 | CN | F | F | H | F | $CH_3$ | $CH_3$ | H |
| I.a.58 | F | CN | F | H | F | $CH_3$ | $CH_3$ | H |
| I.a.59 | CN | F | F | H | F | $CH_3$ | $CH_3$ | H |
| I.a.60 | F | F | H | F | F | $CH_3$ | $CH_3$ | H |
| I.a.61 | Cl | F | H | F | F | $CH_3$ | $CH_3$ | H |
| I.a.62 | F | Cl | H | F | F | $CH_3$ | $CH_3$ | H |
| I.a.63 | CN | F | H | F | F | $CH_3$ | $CH_3$ | H |
| I.a.64 | F | CN | H | F | F | $CH_3$ | $CH_3$ | H |
| I.a.65 | F | F | F | F | F | $CH_3$ | $CH_3$ | H |
| I.a.66 | Cl | F | F | F | F | $CH_3$ | $CH_3$ | H |
| I.a.67 | F | Cl | F | F | F | $CH_3$ | $CH_3$ | H |
| I.a.68 | CN | F | F | F | F | $CH_3$ | $CH_3$ | H |
| I.a.69 | F | CN | F | F | F | $CH_3$ | $CH_3$ | H |
| I.a.70 | H | F | F | F | F | $CH_3$ | $CH_3$ | H |
| I.a.71 | F | F | Br | F | F | $CH_3$ | $CH_3$ | H |
| I.a.72 | F | F | C≡CH | F | F | $CH_3$ | $CH_3$ | H |
| I.a.73 | $CF_3$ | Cl | H | H | F | $CH_3$ | $CH_3$ | H |
| I.a.74 | F | F | I | F | F | $CH_3$ | $CH_3$ | H |
| I.a.75 | F | H | H | H | F | $CH_3$ | $CH_3$ | $CH_3$ |
| I.a.76 | Cl | H | H | H | F | $CH_3$ | $CH_3$ | $CH_3$ |
| I.a.77 | Br | H | H | H | F | $CH_3$ | $CH_3$ | $CH_3$ |
| I.a.78 | CN | H | H | H | F | $CH_3$ | $CH_3$ | $CH_3$ |
| I.a.79 | $CH_3$ | H | H | H | F | $CH_3$ | $CH_3$ | $CH_3$ |
| I.a.80 | F | H | H | F | F | $CH_3$ | $CH_3$ | $CH_3$ |
| I.a.81 | Cl | H | H | F | F | $CH_3$ | $CH_3$ | $CH_3$ |
| I.a.82 | F | H | H | Cl | F | $CH_3$ | $CH_3$ | $CH_3$ |
| I.a.83 | Cl | H | H | F | F | $CH_3$ | $CH_3$ | $CH_3$ |
| I.a.84 | CN | H | H | F | F | $CH_3$ | $CH_3$ | $CH_3$ |
| I.a.85 | F | H | H | CN | F | $CH_3$ | $CH_3$ | $CH_3$ |
| I.a.86 | CN | H | F | H | F | $CH_3$ | $CH_3$ | $CH_3$ |
| I.a.87 | F | H | F | H | F | $CH_3$ | $CH_3$ | $CH_3$ |
| I.a.88 | Cl | H | F | H | F | $CH_3$ | $CH_3$ | $CH_3$ |
| I.a.89 | CN | H | F | H | F | $CH_3$ | $CH_3$ | $CH_3$ |
| I.a.90 | F | F | F | H | F | $CH_3$ | $CH_3$ | $CH_3$ |
| I.a.91 | Cl | F | F | H | F | $CH_3$ | $CH_3$ | $CH_3$ |
| I.a.92 | F | Cl | F | H | F | $CH_3$ | $CH_3$ | $CH_3$ |
| I.a.93 | Cl | F | F | H | F | $CH_3$ | $CH_3$ | $CH_3$ |
| I.a.94 | CN | F | F | H | F | $CH_3$ | $CH_3$ | $CH_3$ |
| I.a.95 | F | CN | F | H | F | $CH_3$ | $CH_3$ | $CH_3$ |
| I.a.96 | CN | F | F | H | F | $CH_3$ | $CH_3$ | $CH_3$ |
| I.a.97 | F | F | H | F | F | $CH_3$ | $CH_3$ | $CH_3$ |
| I.a.98 | Cl | F | H | F | F | $CH_3$ | $CH_3$ | $CH_3$ |
| I.a.99 | F | Cl | H | F | F | $CH_3$ | $CH_3$ | $CH_3$ |
| I.a.100 | CN | F | H | F | F | $CH_3$ | $CH_3$ | $CH_3$ |
| I.a.101 | F | CN | H | F | F | $CH_3$ | $CH_3$ | $CH_3$ |
| I.a.102 | F | F | F | F | F | $CH_3$ | $CH_3$ | $CH_3$ |
| I.a.103 | Cl | F | F | F | F | $CH_3$ | $CH_3$ | $CH_3$ |
| I.a.104 | F | Cl | F | F | F | $CH_3$ | $CH_3$ | $CH_3$ |
| I.a.105 | CN | F | F | F | F | $CH_3$ | $CH_3$ | $CH_3$ |
| I.a.106 | F | CN | F | F | F | $CH_3$ | $CH_3$ | $CH_3$ |
| I.a.107 | H | F | F | F | F | $CH_3$ | $CH_3$ | $CH_3$ |
| I.a.108 | F | F | Br | F | F | $CH_3$ | $CH_3$ | $CH_3$ |
| I.a.109 | F | F | C≡CH | F | F | $CH_3$ | $CH_3$ | $CH_3$ |
| I.a.110 | $CF_3$ | Cl | H | H | F | $CH_3$ | $CH_3$ | $CH_3$ |
| I.a.111 | F | F | I | F | F | $CH_3$ | $CH_3$ | $CH_3$ |
| I.a.112 | F | H | H | H | F | F | F | F |
| I.a.113 | Cl | H | H | H | F | F | F | F |
| I.a.114 | Br | H | H | H | F | F | F | F |
| I.a.115 | CN | H | H | H | F | F | F | F |
| I.a.116 | $CH_3$ | H | H | H | F | F | F | F |
| I.a.117 | F | H | H | F | F | F | F | F |
| I.a.118 | Cl | H | H | F | F | F | F | F |
| I.a.119 | F | H | H | Cl | F | F | F | F |
| I.a.120 | Cl | H | H | F | F | F | F | F |
| I.a.121 | CN | H | H | F | F | F | F | F |
| I.a.122 | F | H | H | CN | F | F | F | F |
| I.a.123 | CN | H | F | H | F | F | F | F |
| I.a.124 | F | H | F | H | F | F | F | F |
| I.a.125 | Cl | H | F | H | F | F | F | F |
| I.a.126 | CN | H | F | H | F | F | F | F |
| I.a.127 | F | F | F | H | F | F | F | F |
| I.a.128 | Cl | F | F | H | F | F | F | F |
| I.a.129 | F | Cl | F | H | F | F | F | F |
| I.a.130 | Cl | F | F | H | F | F | F | F |
| I.a.131 | CN | F | F | H | F | F | F | F |
| I.a.132 | F | CN | F | H | F | F | F | F |
| I.a.133 | CN | F | F | H | F | F | F | F |
| I.a.134 | F | F | H | F | F | F | F | F |
| I.a.135 | Cl | F | H | F | F | F | F | F |
| I.a.136 | F | Cl | H | F | F | F | F | F |
| I.a.137 | CN | F | H | F | F | F | F | F |
| I.a.138 | F | CN | H | F | F | F | F | F |
| I.a.139 | F | F | F | F | F | F | F | F |
| I.a.140 | Cl | F | F | F | F | F | F | F |
| I.a.141 | F | Cl | F | F | F | F | F | F |
| I.a.142 | CN | F | F | F | F | F | F | F |
| I.a.143 | F | CN | F | F | F | F | F | F |
| I.a.144 | H | F | F | F | F | F | F | F |
| I.a.145 | F | F | Br | F | F | F | F | F |
| I.a.146 | F | F | C≡CH | F | F | F | F | F |
| I.a.147 | $CF_3$ | Cl | H | H | F | F | F | F |
| I.a.148 | F | F | I | F | F | F | F | F |
| I.a.149 | F | H | H | H | F | F | $CF_3$ | F |
| I.a.150 | Cl | H | H | H | F | F | $CF_3$ | F |
| I.a.151 | Br | H | H | H | F | F | $CF_3$ | F |
| I.a.152 | CN | H | H | H | F | F | $CF_3$ | F |
| I.a.153 | $CH_3$ | H | H | H | F | F | $CF_3$ | F |
| I.a.154 | F | H | H | F | F | F | $CF_3$ | F |
| I.a.155 | Cl | H | H | F | F | F | $CF_3$ | F |
| I.a.156 | F | H | H | Cl | F | F | $CF_3$ | F |
| I.a.157 | Cl | H | H | F | F | F | $CF_3$ | F |
| I.a.158 | CN | H | H | F | F | F | $CF_3$ | F |
| I.a.159 | F | H | H | CN | F | F | $CF_3$ | F |
| I.a.160 | CN | H | H | F | F | F | $CF_3$ | F |
| I.a.161 | F | H | F | H | F | F | $CF_3$ | F |
| I.a.162 | Cl | H | F | H | F | F | $CF_3$ | F |
| I.a.163 | CN | H | F | H | F | F | $CF_3$ | F |
| I.a.164 | F | F | F | H | F | F | $CF_3$ | F |
| I.a.165 | Cl | F | F | H | F | F | $CF_3$ | F |
| I.a.166 | F | Cl | F | H | F | F | $CF_3$ | F |
| I.a.167 | Cl | F | F | H | F | F | $CF_3$ | F |
| I.a.168 | CN | F | F | H | F | F | $CF_3$ | F |
| I.a.169 | F | CN | F | H | F | F | $CF_3$ | F |
| I.a.170 | CN | F | F | H | F | F | $CF_3$ | F |
| I.a.171 | F | F | H | F | F | F | $CF_3$ | F |
| I.a.172 | Cl | F | H | F | F | F | $CF_3$ | F |
| I.a.173 | F | Cl | H | F | F | F | $CF_3$ | F |
| I.a.174 | CN | F | H | F | F | F | $CF_3$ | F |
| I.a.175 | F | CN | H | F | F | F | $CF_3$ | F |
| I.a.176 | F | F | F | F | F | F | $CF_3$ | F |
| I.a.177 | Cl | F | F | F | F | F | $CF_3$ | F |
| I.a.178 | F | Cl | F | F | F | F | $CF_3$ | F |
| I.a.179 | CN | F | F | F | F | F | $CF_3$ | F |
| I.a.180 | F | CN | F | F | F | F | $CF_3$ | F |
| I.a.181 | H | F | F | F | F | F | $CF_3$ | F |
| I.a.182 | F | F | Br | F | F | F | $CF_3$ | F |
| I.a.183 | F | F | C≡CH | F | F | F | $CF_3$ | F |
| I.a.184 | $CF_3$ | Cl | H | H | F | F | $CF_3$ | F |
| I.a.185 | F | F | I | F | F | F | $CF_3$ | F |
| I.a.186 | F | H | H | H | F | F | $CH_3$ | F |
| I.a.187 | Cl | H | H | H | F | F | $CH_3$ | F |
| I.a.188 | Br | H | H | H | F | F | $CH_3$ | F |
| I.a.189 | CN | H | H | H | F | F | $CH_3$ | F |
| I.a.190 | $CH_3$ | H | H | H | F | F | $CH_3$ | F |
| I.a.191 | F | H | H | F | F | F | $CH_3$ | F |
| I.a.192 | Cl | H | H | F | F | F | $CH_3$ | F |
| I.a.193 | F | H | H | Cl | F | F | $CH_3$ | F |
| I.a.194 | Cl | H | H | F | F | F | $CH_3$ | F |
| I.a.195 | CN | H | H | F | F | F | $CH_3$ | F |
| I.a.196 | F | H | H | CN | F | F | $CH_3$ | F |
| I.a.197 | CN | H | H | F | F | F | $CH_3$ | F |
| I.a.198 | F | H | F | H | F | F | $CH_3$ | F |
| I.a.199 | Cl | H | F | H | F | F | $CH_3$ | F |
| I.a.200 | CN | H | F | H | F | F | $CH_3$ | F |
| I.a.201 | F | F | F | H | F | F | $CH_3$ | F |
| I.a.202 | Cl | F | F | H | F | F | $CH_3$ | F |
| I.a.203 | F | Cl | F | H | F | F | $CH_3$ | F |
| I.a.204 | Cl | F | F | H | F | F | $CH_3$ | F |
| I.a.205 | CN | F | F | H | F | F | $CH_3$ | F |
| I.a.206 | F | CN | F | H | F | F | $CH_3$ | F |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.207 | CN | F | F | H | F | F | CH₃ | F |
| I.a.208 | F | F | H | F | F | F | CH₃ | F |
| I.a.209 | Cl | F | H | F | F | F | CH₃ | F |
| I.a.210 | F | Cl | H | F | F | F | CH₃ | F |
| I.a.211 | CN | F | H | F | F | F | CH₃ | F |
| I.a.212 | F | CN | H | F | F | F | CH₃ | F |
| I.a.213 | F | F | F | F | F | F | CH₃ | F |
| I.a.214 | Cl | F | F | F | F | F | CH₃ | F |
| I.a.215 | F | Cl | F | F | F | F | CH₃ | F |
| I.a.216 | CN | F | F | F | F | F | CH₃ | F |
| I.a.217 | F | CN | F | F | F | F | CH₃ | F |
| I.a.218 | H | F | F | F | F | F | CH₃ | F |
| I.a.219 | F | F | Br | F | F | F | CH₃ | F |
| I.a.220 | F | F | C≡CH | F | F | F | CH₃ | F |
| I.a.221 | CF₃ | Cl | H | H | F | F | CH₃ | F |
| I.a.222 | F | F | I | F | F | F | CH₃ | F |
| I.a.223 | F | H | H | H | F | F | CH₃ | H |
| I.a.224 | Cl | H | H | H | F | F | CH₃ | H |
| I.a.225 | Br | H | H | H | F | F | CH₃ | H |
| I.a.226 | CN | H | H | H | F | F | CH₃ | H |
| I.a.227 | CH₃ | H | H | H | F | F | CH₃ | H |
| I.a.228 | F | H | H | F | F | F | CH₃ | H |
| I.a.229 | Cl | H | H | F | F | F | CH₃ | H |
| I.a.230 | F | H | H | Cl | F | F | CH₃ | H |
| I.a.231 | Cl | H | H | F | F | F | CH₃ | H |
| I.a.232 | CN | H | H | F | F | F | CH₃ | H |
| I.a.233 | F | H | H | CN | F | F | CH₃ | H |
| I.a.234 | CN | H | H | F | F | F | CH₃ | H |
| I.a.235 | F | H | F | H | F | F | CH₃ | H |
| I.a.236 | Cl | H | F | H | F | F | CH₃ | H |
| I.a.237 | CN | H | F | H | F | F | CH₃ | H |
| I.a.238 | F | F | F | H | F | F | CH₃ | H |
| I.a.239 | Cl | F | F | H | F | F | CH₃ | H |
| I.a.240 | F | Cl | F | H | F | F | CH₃ | H |
| I.a.241 | Cl | F | F | H | F | F | CH₃ | H |
| I.a.242 | CN | F | F | H | F | F | CH₃ | H |
| I.a.243 | F | CN | F | H | F | F | CH₃ | H |
| I.a.244 | CN | F | F | H | F | F | CH₃ | H |
| I.a.245 | F | F | H | F | F | F | CH₃ | H |
| I.a.246 | Cl | F | H | F | F | F | CH₃ | H |
| I.a.247 | F | Cl | H | F | F | F | CH₃ | H |
| I.a.248 | CN | F | H | F | F | F | CH₃ | H |
| I.a.249 | F | CN | H | F | F | F | CH₃ | H |
| I.a.250 | F | F | F | F | F | F | CH₃ | H |
| I.a.251 | Cl | F | F | F | F | F | CH₃ | H |
| I.a.252 | F | Cl | F | F | F | F | CH₃ | H |
| I.a.253 | CN | F | F | F | F | F | CH₃ | H |
| I.a.254 | F | CN | F | F | F | F | CH₃ | H |
| I.a.255 | H | F | F | F | F | F | CH₃ | H |
| I.a.256 | F | F | Br | F | F | F | CH₃ | H |
| I.a.257 | F | F | C≡CH | F | F | F | CH₃ | H |
| I.a.258 | CF₃ | Cl | H | H | F | F | CH₃ | H |
| I.a.259 | F | F | I | F | F | F | CH₃ | H |
| I.a.260 | F | H | H | H | F | F | CH₃ | CH₃ |
| I.a.261 | Cl | H | H | H | F | F | CH₃ | CH₃ |
| I.a.262 | Br | H | H | H | F | F | CH₃ | CH₃ |
| I.a.263 | CN | H | H | H | F | F | CH₃ | CH₃ |
| I.a.264 | CH₃ | H | H | H | F | F | CH₃ | CH₃ |
| I.a.265 | F | H | H | F | F | F | CH₃ | CH₃ |
| I.a.266 | Cl | H | H | F | F | F | CH₃ | CH₃ |
| I.a.267 | F | H | H | Cl | F | F | CH₃ | CH₃ |
| I.a.268 | Cl | H | H | F | F | F | CH₃ | CH₃ |
| I.a.269 | CN | H | H | F | F | F | CH₃ | CH₃ |
| I.a.270 | F | H | H | CN | F | F | CH₃ | CH₃ |
| I.a.271 | CN | H | H | F | F | F | CH₃ | CH₃ |
| I.a.272 | F | H | F | H | F | F | CH₃ | CH₃ |
| I.a.273 | Cl | H | F | H | F | F | CH₃ | CH₃ |
| I.a.274 | CN | H | F | H | F | F | CH₃ | CH₃ |
| I.a.275 | F | F | F | H | F | F | CH₃ | CH₃ |
| I.a.276 | Cl | F | F | H | F | F | CH₃ | CH₃ |
| I.a.277 | F | Cl | F | H | F | F | CH₃ | CH₃ |
| I.a.278 | Cl | F | F | H | F | F | CH₃ | CH₃ |
| I.a.279 | CN | F | F | H | F | F | CH₃ | CH₃ |
| I.a.280 | F | CN | F | H | F | F | CH₃ | CH₃ |
| I.a.281 | CN | F | F | H | F | F | CH₃ | CH₃ |
| I.a.282 | F | F | H | F | F | F | CH₃ | CH₃ |
| I.a.283 | Cl | F | H | F | F | F | CH₃ | CH₃ |
| I.a.284 | F | Cl | H | F | F | F | CH₃ | CH₃ |
| I.a.285 | CN | F | H | F | F | F | CH₃ | CH₃ |
| I.a.286 | F | CN | H | F | F | F | CH₃ | CH₃ |
| I.a.287 | F | F | F | F | F | F | CH₃ | CH₃ |
| I.a.288 | Cl | F | F | F | F | F | CH₃ | CH₃ |
| I.a.289 | F | Cl | F | F | F | F | CH₃ | CH₃ |
| I.a.290 | CN | F | F | F | F | F | CH₃ | CH₃ |
| I.a.291 | F | CN | F | F | F | F | CH₃ | CH₃ |
| I.a.292 | H | F | F | F | F | F | CH₃ | CH₃ |
| I.a.293 | F | F | Br | F | F | F | CH₃ | CH₃ |
| I.a.294 | F | F | C≡CH | F | F | F | CH₃ | CH₃ |
| I.a.295 | CF₃ | Cl | H | H | F | F | CH₃ | CH₃ |
| I.a.296 | F | F | I | F | F | F | CH₃ | CH₃ |
| I.a.297 | F | H | H | H | F | Cl | CH₃ | CH₃ |
| I.a.298 | Cl | H | H | H | F | Cl | CH₃ | CH₃ |
| I.a.299 | Br | H | H | H | F | Cl | CH₃ | CH₃ |
| I.a.300 | CN | H | H | H | F | Cl | CH₃ | CH₃ |
| I.a.301 | CH₃ | H | H | H | F | Cl | CH₃ | CH₃ |
| I.a.302 | F | H | H | F | F | Cl | CH₃ | CH₃ |
| I.a.303 | Cl | H | H | F | F | Cl | CH₃ | CH₃ |
| I.a.304 | F | H | H | Cl | F | Cl | CH₃ | CH₃ |
| I.a.305 | Cl | H | H | F | F | Cl | CH₃ | CH₃ |
| I.a.306 | CN | H | H | F | F | Cl | CH₃ | CH₃ |
| I.a.307 | F | H | H | CN | F | Cl | CH₃ | CH₃ |
| I.a.308 | CN | H | H | F | F | Cl | CH₃ | CH₃ |
| I.a.309 | F | H | F | H | F | Cl | CH₃ | CH₃ |
| I.a.310 | Cl | H | F | H | F | Cl | CH₃ | CH₃ |
| I.a.311 | CN | H | F | H | F | Cl | CH₃ | CH₃ |
| I.a.312 | F | F | F | H | F | Cl | CH₃ | CH₃ |
| I.a.313 | Cl | F | F | H | F | Cl | CH₃ | CH₃ |
| I.a.314 | F | Cl | F | H | F | Cl | CH₃ | CH₃ |
| I.a.315 | Cl | F | F | H | F | Cl | CH₃ | CH₃ |
| I.a.316 | CN | F | F | H | F | Cl | CH₃ | CH₃ |
| I.a.317 | F | CN | F | H | F | Cl | CH₃ | CH₃ |
| I.a.318 | CN | F | F | H | F | Cl | CH₃ | CH₃ |
| I.a.319 | F | F | H | F | F | Cl | CH₃ | CH₃ |
| I.a.320 | Cl | F | H | F | F | Cl | CH₃ | CH₃ |
| I.a.321 | F | Cl | H | F | F | Cl | CH₃ | CH₃ |
| I.a.322 | CN | F | H | F | F | Cl | CH₃ | CH₃ |
| I.a.323 | F | CN | H | F | F | Cl | CH₃ | CH₃ |
| I.a.324 | F | F | F | F | F | Cl | CH₃ | CH₃ |
| I.a.325 | Cl | F | F | F | F | Cl | CH₃ | CH₃ |
| I.a.326 | F | Cl | F | F | F | Cl | CH₃ | CH₃ |
| I.a.327 | CN | F | F | F | F | Cl | CH₃ | CH₃ |
| I.a.328 | F | CN | F | F | F | Cl | CH₃ | CH₃ |
| I.a.329 | H | F | F | F | F | Cl | CH₃ | CH₃ |
| I.a.330 | F | F | Br | F | F | Cl | CH₃ | CH₃ |
| I.a.331 | F | F | C≡CH | F | F | Cl | CH₃ | CH₃ |
| I.a.332 | CF₃ | Cl | H | H | F | Cl | CH₃ | CH₃ |
| I.a.333 | F | F | I | F | F | Cl | CH₃ | CH₃ |
| I.a.334 | F | H | H | H | F | F | C₂H₅ | CH₃ |
| I.a.335 | Cl | H | H | H | F | F | C₂H₅ | CH₃ |
| I.a.336 | Br | H | H | H | F | F | C₂H₅ | CH₃ |
| I.a.337 | CN | H | H | H | F | F | C₂H₅ | CH₃ |
| I.a.338 | CH₃ | H | H | H | F | F | C₂H₅ | CH₃ |
| I.a.339 | F | H | H | F | F | F | C₂H₅ | CH₃ |
| I.a.340 | Cl | H | H | F | F | F | C₂H₅ | CH₃ |
| I.a.341 | F | H | H | Cl | F | F | C₂H₅ | CH₃ |
| I.a.342 | Cl | H | H | F | F | F | C₂H₅ | CH₃ |
| I.a.343 | CN | H | H | F | F | F | C₂H₅ | CH₃ |
| I.a.344 | F | H | H | CN | F | F | C₂H₅ | CH₃ |
| I.a.345 | CN | H | H | F | F | F | C₂H₅ | CH₃ |
| I.a.346 | F | H | F | H | F | F | C₂H₅ | CH₃ |
| I.a.347 | Cl | H | F | H | F | F | C₂H₅ | CH₃ |
| I.a.348 | CN | H | F | H | F | F | C₂H₅ | CH₃ |
| I.a.349 | F | F | F | H | F | F | C₂H₅ | CH₃ |
| I.a.350 | Cl | F | F | H | F | F | C₂H₅ | CH₃ |
| I.a.351 | F | Cl | F | H | F | F | C₂H₅ | CH₃ |
| I.a.352 | Cl | F | F | H | F | F | C₂H₅ | CH₃ |
| I.a.353 | CN | F | F | H | F | F | C₂H₅ | CH₃ |
| I.a.354 | F | CN | F | H | F | F | C₂H₅ | CH₃ |
| I.a.355 | CN | F | F | H | F | F | C₂H₅ | CH₃ |
| I.a.356 | F | F | H | F | F | F | C₂H₅ | CH₃ |
| I.a.357 | Cl | F | H | F | F | F | C₂H₅ | CH₃ |
| I.a.358 | F | Cl | H | F | F | F | C₂H₅ | CH₃ |
| I.a.359 | CN | F | H | F | F | F | C₂H₅ | CH₃ |
| I.a.360 | F | CN | H | F | F | F | C₂H₅ | CH₃ |
| I.a.361 | F | F | F | F | F | F | C₂H₅ | CH₃ |
| I.a.362 | Cl | F | F | F | F | F | C₂H₅ | CH₃ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.363 | F | Cl | F | F | F | F | $C_2H_5$ | $CH_3$ |
| I.a.364 | CN | F | F | F | F | F | $C_2H_5$ | $CH_3$ |
| I.a.365 | F | CN | F | F | F | F | $C_2H_5$ | $CH_3$ |
| I.a.366 | H | F | F | F | F | F | $C_2H_5$ | $CH_3$ |
| I.a.367 | F | F | Br | F | F | F | $C_2H_5$ | $CH_3$ |
| I.a.368 | F | F | C≡CH | F | F | F | $C_2H_5$ | $CH_3$ |
| I.a.369 | $CF_3$ | Cl | H | H | F | F | $C_2H_5$ | $CH_3$ |
| I.a.370 | F | F | I | F | F | F | $C_2H_5$ | $CH_3$ |
| I.a.371 | F | H | H | H | F | F | $C_2H_5$ | $C_2H_5$ |
| I.a.372 | Cl | H | H | H | F | F | $C_2H_5$ | $C_2H_5$ |
| I.a.373 | Br | H | H | H | F | F | $C_2H_5$ | $C_2H_5$ |
| I.a.374 | CN | H | H | H | F | F | $C_2H_5$ | $C_2H_5$ |
| I.a.375 | $CH_3$ | H | H | H | F | F | $C_2H_5$ | $C_2H_5$ |
| I.a.376 | F | H | H | F | F | F | $C_2H_5$ | $C_2H_5$ |
| I.a.377 | Cl | H | H | F | F | F | $C_2H_5$ | $C_2H_5$ |
| I.a.378 | F | H | H | Cl | F | F | $C_2H_5$ | $C_2H_5$ |
| I.a.379 | Cl | H | H | F | F | F | $C_2H_5$ | $C_2H_5$ |
| I.a.380 | CN | H | H | F | F | F | $C_2H_5$ | $C_2H_5$ |
| I.a.381 | F | H | H | CN | F | F | $C_2H_5$ | $C_2H_5$ |
| I.a.382 | CN | H | H | F | F | F | $C_2H_5$ | $C_2H_5$ |
| I.a.383 | F | H | F | H | F | F | $C_2H_5$ | $C_2H_5$ |
| I.a.384 | Cl | H | F | H | F | F | $C_2H_5$ | $C_2H_5$ |
| I.a.385 | CN | H | F | H | F | F | $C_2H_5$ | $C_2H_5$ |
| I.a.386 | F | F | F | H | F | F | $C_2H_5$ | $C_2H_5$ |
| I.a.387 | Cl | F | F | H | F | F | $C_2H_5$ | $C_2H_5$ |
| I.a.388 | F | Cl | F | H | F | F | $C_2H_5$ | $C_2H_5$ |
| I.a.389 | Cl | F | F | H | F | F | $C_2H_5$ | $C_2H_5$ |
| I.a.390 | CN | F | F | H | F | F | $C_2H_5$ | $C_2H_5$ |
| I.a.391 | F | CN | F | H | F | F | $C_2H_5$ | $C_2H_5$ |
| I.a.392 | CN | F | F | H | F | F | $C_2H_5$ | $C_2H_5$ |
| I.a.393 | F | F | H | F | F | F | $C_2H_5$ | $C_2H_5$ |
| I.a.394 | Cl | F | H | F | F | F | $C_2H_5$ | $C_2H_5$ |
| I.a.395 | F | Cl | H | F | F | F | $C_2H_5$ | $C_2H_5$ |
| I.a.396 | CN | F | H | F | F | F | $C_2H_5$ | $C_2H_5$ |
| I.a.397 | F | CN | H | F | F | F | $C_2H_5$ | $C_2H_5$ |
| I.a.398 | F | F | F | F | F | F | $C_2H_5$ | $C_2H_5$ |
| I.a.399 | Cl | F | F | F | F | F | $C_2H_5$ | $C_2H_5$ |
| I.a.400 | F | Cl | F | F | F | F | $C_2H_5$ | $C_2H_5$ |
| I.a.401 | CN | F | F | F | F | F | $C_2H_5$ | $C_2H_5$ |
| I.a.402 | F | CN | F | F | F | F | $C_2H_5$ | $C_2H_5$ |
| I.a.403 | H | F | F | F | F | F | $C_2H_5$ | $C_2H_5$ |
| I.a.404 | F | F | Br | F | F | F | $C_2H_5$ | $C_2H_5$ |
| I.a.405 | F | F | C≡CH | F | F | F | $C_2H_5$ | $C_2H_5$ |
| I.a.406 | $CF_3$ | Cl | H | H | F | F | $C_2H_5$ | $C_2H_5$ |
| I.a.407 | F | F | I | F | F | F | $C_2H_5$ | $C_2H_5$ |
| I.a.408 | F | H | H | H | F | H | —$(CH_2)_2$— | |
| I.a.409 | Cl | H | H | H | F | H | —$(CH_2)_2$— | |
| I.a.410 | Br | H | H | H | F | H | —$(CH_2)_2$— | |
| I.a.411 | CN | H | H | H | F | H | —$(CH_2)_2$— | |
| I.a.412 | $CH_3$ | H | H | H | F | H | —$(CH_2)_2$— | |
| I.a.413 | F | H | H | F | F | H | —$(CH_2)_2$— | |
| I.a.414 | Cl | H | H | F | F | H | —$(CH_2)_2$— | |
| I.a.415 | F | H | H | Cl | F | H | —$(CH_2)_2$— | |
| I.a.416 | Cl | H | H | F | F | H | —$(CH_2)_2$— | |
| I.a.417 | CN | H | H | F | F | H | —$(CH_2)_2$— | |
| I.a.418 | F | H | H | CN | F | H | —$(CH_2)_2$— | |
| I.a.419 | CN | H | H | F | F | H | —$(CH_2)_2$— | |
| I.a.420 | F | H | F | H | F | H | —$(CH_2)_2$— | |
| I.a.421 | Cl | H | F | H | F | H | —$(CH_2)_2$— | |
| I.a.422 | CN | H | F | H | F | H | —$(CH_2)_2$— | |
| I.a.423 | F | F | F | H | F | H | —$(CH_2)_2$— | |
| I.a.424 | Cl | F | F | H | F | H | —$(CH_2)_2$— | |
| I.a.425 | F | Cl | F | H | F | H | —$(CH_2)_2$— | |
| I.a.426 | Cl | F | F | H | F | H | —$(CH_2)_2$— | |
| I.a.427 | CN | F | F | H | F | H | —$(CH_2)_2$— | |
| I.a.428 | F | CN | F | H | F | H | —$(CH_2)_2$— | |
| I.a.429 | CN | F | F | H | F | H | —$(CH_2)_2$— | |
| I.a.430 | F | F | F | F | F | H | —$(CH_2)_2$— | |
| I.a.431 | Cl | F | F | F | F | H | —$(CH_2)_2$— | |
| I.a.432 | F | Cl | F | F | F | H | —$(CH_2)_2$— | |
| I.a.433 | CN | F | F | F | F | H | —$(CH_2)_2$— | |
| I.a.434 | F | CN | F | F | F | H | —$(CH_2)_2$— | |
| I.a.435 | F | F | H | F | F | H | —$(CH_2)_2$— | |
| I.a.436 | Cl | F | H | F | F | H | —$(CH_2)_2$— | |
| I.a.437 | F | Cl | H | F | F | H | —$(CH_2)_2$— | |
| I.a.438 | CN | F | H | F | F | H | —$(CH_2)_2$— | |
| I.a.439 | F | CN | H | F | F | H | —$(CH_2)_2$— | |
| I.a.440 | H | F | F | F | F | H | —$(CH_2)_2$— | |
| I.a.441 | F | F | Br | F | F | H | —$(CH_2)_2$— | |
| I.a.442 | F | F | C≡CH | F | F | H | —$(CH_2)_2$— | |
| I.a.443 | $CF_3$ | Cl | H | H | F | H | —$(CH_2)_2$— | |
| I.a.444 | F | F | I | F | F | H | —$(CH_2)_2$— | |
| I.a.445 | F | H | H | H | F | H | —$(CH_2)_3$— | |
| I.a.446 | Cl | H | H | H | F | H | —$(CH_2)_3$— | |
| I.a.447 | Br | H | H | H | F | H | —$(CH_2)_3$— | |
| I.a.448 | CN | H | H | H | F | H | —$(CH_2)_3$— | |
| I.a.449 | $CH_3$ | H | H | H | F | H | —$(CH_2)_3$— | |
| I.a.450 | F | H | H | F | F | H | —$(CH_2)_3$— | |
| I.a.451 | Cl | H | H | F | F | H | —$(CH_2)_3$— | |
| I.a.452 | F | H | H | Cl | F | H | —$(CH_2)_3$— | |
| I.a.453 | Cl | H | H | F | F | H | —$(CH_2)_3$— | |
| I.a.454 | CN | H | H | F | F | H | —$(CH_2)_3$— | |
| I.a.455 | F | H | H | CN | F | H | —$(CH_2)_3$— | |
| I.a.456 | CN | H | H | F | F | H | —$(CH_2)_3$— | |
| I.a.457 | F | H | F | H | F | H | —$(CH_2)_3$— | |
| I.a.458 | Cl | H | F | H | F | H | —$(CH_2)_3$— | |
| I.a.459 | CN | H | F | H | F | H | —$(CH_2)_3$— | |
| I.a.460 | F | F | F | H | F | H | —$(CH_2)_3$— | |
| I.a.461 | Cl | F | F | H | F | H | —$(CH_2)_3$— | |
| I.a.462 | F | Cl | F | H | F | H | —$(CH_2)_3$— | |
| I.a.463 | Cl | F | F | H | F | H | —$(CH_2)_3$— | |
| I.a.464 | CN | F | F | H | F | H | —$(CH_2)_3$— | |
| I.a.465 | F | CN | F | H | F | H | —$(CH_2)_3$— | |
| I.a.466 | CN | F | F | H | F | H | —$(CH_2)_3$— | |
| I.a.467 | F | F | H | F | F | H | —$(CH_2)_3$— | |
| I.a.468 | Cl | F | H | F | F | H | —$(CH_2)_3$— | |
| I.a.469 | F | Cl | H | F | F | H | —$(CH_2)_3$— | |
| I.a.470 | CN | F | H | F | F | H | —$(CH_2)_3$— | |
| I.a.471 | F | CN | H | F | F | H | —$(CH_2)_3$— | |
| I.a.472 | F | F | F | F | F | H | —$(CH_2)_3$— | |
| I.a.473 | Cl | F | F | F | F | H | —$(CH_2)_3$— | |
| I.a.474 | F | Cl | F | F | F | H | —$(CH_2)_3$— | |
| I.a.475 | CN | F | F | F | F | H | —$(CH_2)_3$— | |
| I.a.476 | F | CN | F | F | F | H | —$(CH_2)_3$— | |
| I.a.477 | H | F | F | F | F | H | —$(CH_2)_3$— | |
| I.a.478 | F | F | Br | F | F | H | —$(CH_2)_3$— | |
| I.a.479 | F | F | C≡CH | F | F | H | —$(CH_2)_3$— | |
| I.a.480 | $CF_3$ | Cl | H | H | F | H | —$(CH_2)_3$— | |
| I.a.481 | F | F | I | F | F | H | —$(CH_2)_3$— | |
| I.a.482 | F | H | H | H | F | H | —$(CH_2)_4$— | |
| I.a.483 | Cl | H | H | H | F | H | —$(CH_2)_4$— | |
| I.a.484 | Br | H | H | H | F | H | —$(CH_2)_4$— | |
| I.a.485 | CN | H | H | H | F | H | —$(CH_2)_4$— | |
| I.a.486 | $CH_3$ | H | H | H | F | H | —$(CH_2)_4$— | |
| I.a.487 | F | H | H | F | F | H | —$(CH_2)_4$— | |
| I.a.488 | Cl | H | H | F | F | H | —$(CH_2)_4$— | |
| I.a.489 | F | H | H | Cl | F | H | —$(CH_2)_4$— | |
| I.a.490 | Cl | H | H | F | F | H | —$(CH_2)_4$— | |
| I.a.491 | CN | H | H | F | F | H | —$(CH_2)_4$— | |
| I.a.492 | F | H | H | CN | F | H | —$(CH_2)_4$— | |
| I.a.493 | CN | H | H | F | F | H | —$(CH_2)_4$— | |
| I.a.494 | F | H | F | H | F | H | —$(CH_2)_4$— | |
| I.a.495 | Cl | H | F | H | F | H | —$(CH_2)_4$— | |
| I.a.496 | CN | H | F | H | F | H | —$(CH_2)_4$— | |
| I.a.497 | F | F | F | H | F | H | —$(CH_2)_4$— | |
| I.a.498 | Cl | F | F | H | F | H | —$(CH_2)_4$— | |
| I.a.499 | F | Cl | F | H | F | H | —$(CH_2)_4$— | |
| I.a.500 | Cl | F | F | H | F | H | —$(CH_2)_4$— | |
| I.a.501 | CN | F | F | H | F | H | —$(CH_2)_4$— | |
| I.a.502 | F | CN | F | H | F | H | —$(CH_2)_4$— | |
| I.a.503 | CN | F | F | H | F | H | —$(CH_2)_4$— | |
| I.a.504 | F | F | H | F | F | H | —$(CH_2)_4$— | |
| I.a.505 | Cl | F | H | F | F | H | —$(CH_2)_4$— | |
| I.a.506 | F | Cl | H | F | F | H | —$(CH_2)_4$— | |
| I.a.507 | CN | F | H | F | F | H | —$(CH_2)_4$— | |
| I.a.508 | F | CN | H | F | F | H | —$(CH_2)_4$— | |
| I.a.509 | F | F | F | F | F | H | —$(CH_2)_4$— | |
| I.a.510 | Cl | F | F | F | F | H | —$(CH_2)_4$— | |
| I.a.511 | F | Cl | F | F | F | H | —$(CH_2)_4$— | |
| I.a.512 | CN | F | F | F | F | H | —$(CH_2)_4$— | |
| I.a.513 | F | CN | F | F | F | H | —$(CH_2)_4$— | |
| I.a.514 | H | F | F | F | F | H | —$(CH_2)_4$— | |
| I.a.515 | F | F | Br | F | F | H | —$(CH_2)_4$— | |
| I.a.516 | F | F | C≡CH | F | F | H | —$(CH_2)_4$— | |
| I.a.517 | $CF_3$ | Cl | H | H | F | H | —$(CH_2)_4$— | |
| I.a.518 | F | F | I | F | F | H | —$(CH_2)_4$— | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.519 | F | H | H | H | F | H | | —(CH$_2$)$_5$— |
| I.a.520 | Cl | H | H | H | F | H | | —(CH$_2$)$_5$— |
| I.a.521 | Br | H | H | H | F | H | | —(CH$_2$)$_5$— |
| I.a.522 | CN | H | H | H | F | H | | —(CH$_2$)$_5$— |
| I.a.523 | CH$_3$ | H | H | H | F | H | | —(CH$_2$)$_5$— |
| I.a.524 | F | H | H | F | F | H | | —(CH$_2$)$_5$— |
| I.a.525 | Cl | H | H | F | F | H | | —(CH$_2$)$_5$— |
| I.a.526 | F | H | H | Cl | F | H | | —(CH$_2$)$_5$— |
| I.a.527 | Cl | H | H | F | F | H | | —(CH$_2$)$_5$— |
| I.a.528 | CN | H | H | F | F | H | | —(CH$_2$)$_5$— |
| I.a.529 | F | H | H | CN | F | H | | —(CH$_2$)$_5$— |
| I.a.530 | CN | H | H | F | F | H | | —(CH$_2$)$_5$— |
| I.a.531 | F | H | F | H | F | H | | —(CH$_2$)$_5$— |
| I.a.532 | Cl | H | F | H | F | H | | —(CH$_2$)$_5$— |
| I.a.533 | CN | H | F | H | F | H | | —(CH$_2$)$_5$— |
| I.a.534 | F | F | F | H | F | H | | —(CH$_2$)$_5$— |
| I.a.535 | Cl | F | F | H | F | H | | —(CH$_2$)$_5$— |
| I.a.536 | F | Cl | F | H | F | H | | —(CH$_2$)$_5$— |
| I.a.537 | Cl | F | F | H | F | H | | —(CH$_2$)$_5$— |
| I.a.538 | CN | F | F | H | F | H | | —(CH$_2$)$_5$— |
| I.a.539 | F | CN | F | H | F | H | | —(CH$_2$)$_5$— |
| I.a.540 | CN | F | F | H | F | H | | —(CH$_2$)$_5$— |
| I.a.541 | F | F | H | F | F | H | | —(CH$_2$)$_5$— |
| I.a.542 | Cl | F | H | F | F | H | | —(CH$_2$)$_5$— |
| I.a.543 | F | Cl | H | F | F | H | | —(CH$_2$)$_5$— |
| I.a.544 | CN | F | H | F | F | H | | —(CH$_2$)$_5$— |
| I.a.545 | F | CN | H | F | F | H | | —(CH$_2$)$_5$— |
| I.a.546 | F | F | F | F | F | H | | —(CH$_2$)$_5$— |
| I.a.547 | Cl | F | F | F | F | H | | —(CH$_2$)$_5$— |
| I.a.548 | F | Cl | F | F | F | H | | —(CH$_2$)$_5$— |
| I.a.549 | CN | F | F | F | F | H | | —(CH$_2$)$_5$— |
| I.a.550 | F | CN | F | F | F | H | | —(CH$_2$)$_5$— |
| I.a.551 | H | F | F | F | F | H | | —(CH$_2$)$_5$— |
| I.a.552 | F | F | Br | F | F | H | | —(CH$_2$)$_5$— |
| I.a.553 | F | F | C≡CH | F | F | H | | —(CH$_2$)$_5$— |
| I.a.554 | CF$_3$ | Cl | H | H | F | H | | —(CH$_2$)$_5$— |
| I.a.555 | F | F | I | F | F | H | | —(CH$_2$)$_5$— |
| I.a.556 | F | H | H | H | F | CH$_3$ | | —(CH$_2$)$_2$— |
| I.a.557 | Cl | H | H | H | F | CH$_3$ | | —(CH$_2$)$_2$— |
| I.a.558 | Br | H | H | H | F | CH$_3$ | | —(CH$_2$)$_2$— |
| I.a.559 | CN | H | H | H | F | CH$_3$ | | —(CH$_2$)$_2$— |
| I.a.560 | CH$_3$ | H | H | H | F | CH$_3$ | | —(CH$_2$)$_2$— |
| I.a.561 | F | H | H | F | F | CH$_3$ | | —(CH$_2$)$_2$— |
| I.a.562 | Cl | H | H | F | F | CH$_3$ | | —(CH$_2$)$_2$— |
| I.a.563 | F | H | H | Cl | F | CH$_3$ | | —(CH$_2$)$_2$— |
| I.a.564 | Cl | H | H | F | F | CH$_3$ | | —(CH$_2$)$_2$— |
| I.a.565 | CN | H | H | F | F | CH$_3$ | | —(CH$_2$)$_2$— |
| I.a.566 | F | H | H | CN | F | CH$_3$ | | —(CH$_2$)$_2$— |
| I.a.567 | CN | H | H | F | F | CH$_3$ | | —(CH$_2$)$_2$— |
| I.a.568 | F | H | F | H | F | CH$_3$ | | —(CH$_2$)$_2$— |
| I.a.569 | Cl | H | F | H | F | CH$_3$ | | —(CH$_2$)$_2$— |
| I.a.570 | CN | H | F | H | F | CH$_3$ | | —(CH$_2$)$_2$— |
| I.a.571 | F | F | F | H | F | CH$_3$ | | —(CH$_2$)$_2$— |
| I.a.572 | Cl | F | F | H | F | CH$_3$ | | —(CH$_2$)$_2$— |
| I.a.573 | F | Cl | F | H | F | CH$_3$ | | —(CH$_2$)$_2$— |
| I.a.574 | Cl | F | F | H | F | CH$_3$ | | —(CH$_2$)$_2$— |
| I.a.575 | CN | F | F | H | F | CH$_3$ | | —(CH$_2$)$_2$— |
| I.a.576 | F | CN | F | H | F | CH$_3$ | | —(CH$_2$)$_2$— |
| I.a.577 | CN | F | F | H | F | CH$_3$ | | —(CH$_2$)$_2$— |
| I.a.578 | F | F | H | F | F | CH$_3$ | | —(CH$_2$)$_2$— |
| I.a.579 | Cl | F | H | F | F | CH$_3$ | | —(CH$_2$)$_2$— |
| I.a.580 | F | Cl | H | F | F | CH$_3$ | | —(CH$_2$)$_2$— |
| I.a.581 | CN | F | H | F | F | CH$_3$ | | —(CH$_2$)$_2$— |
| I.a.582 | F | CN | H | F | F | CH$_3$ | | —(CH$_2$)$_2$— |
| I.a.583 | F | F | F | F | F | CH$_3$ | | —(CH$_2$)$_2$— |
| I.a.584 | Cl | F | F | F | F | CH$_3$ | | —(CH$_2$)$_2$— |
| I.a.585 | F | Cl | F | F | F | CH$_3$ | | —(CH$_2$)$_2$— |
| I.a.586 | CN | F | F | F | F | CH$_3$ | | —(CH$_2$)$_2$— |
| I.a.587 | F | CN | F | F | F | CH$_3$ | | —(CH$_2$)$_2$— |
| I.a.588 | H | F | F | F | F | CH$_3$ | | —(CH$_2$)$_2$— |
| I.a.589 | F | F | Br | F | F | CH$_3$ | | —(CH$_2$)$_2$— |
| I.a.590 | F | F | C≡CH | F | F | CH$_3$ | | —(CH$_2$)$_2$— |
| I.a.591 | CF$_3$ | Cl | H | H | F | CH$_3$ | | —(CH$_2$)$_2$— |
| I.a.592 | F | F | I | F | F | CH$_3$ | | —(CH$_2$)$_2$— |
| I.a.593 | F | H | H | H | F | CH$_3$ | | —(CH$_2$)$_3$— |
| I.a.594 | Cl | H | H | H | F | CH$_3$ | | —(CH$_2$)$_3$— |
| I.a.595 | Br | H | H | H | F | CH$_3$ | | —(CH$_2$)$_3$— |
| I.a.596 | CN | H | H | H | F | CH$_3$ | | —(CH$_2$)$_3$— |
| I.a.597 | CH$_3$ | H | H | H | F | CH$_3$ | | —(CH$_2$)$_3$— |
| I.a.598 | F | H | H | F | F | CH$_3$ | | —(CH$_2$)$_3$— |
| I.a.599 | Cl | H | H | F | F | CH$_3$ | | —(CH$_2$)$_3$— |
| I.a.600 | F | H | H | Cl | F | CH$_3$ | | —(CH$_2$)$_3$— |
| I.a.601 | Cl | H | H | F | F | CH$_3$ | | —(CH$_2$)$_3$— |
| I.a.602 | CN | H | H | F | F | CH$_3$ | | —(CH$_2$)$_3$— |
| I.a.603 | F | H | H | CN | F | CH$_3$ | | —(CH$_2$)$_3$— |
| I.a.604 | CN | H | H | F | F | CH$_3$ | | —(CH$_2$)$_3$— |
| I.a.605 | F | H | F | H | F | CH$_3$ | | —(CH$_2$)$_3$— |
| I.a.606 | Cl | H | F | H | F | CH$_3$ | | —(CH$_2$)$_3$— |
| I.a.607 | CN | H | F | H | F | CH$_3$ | | —(CH$_2$)$_3$— |
| I.a.608 | F | F | F | H | F | CH$_3$ | | —(CH$_2$)$_3$— |
| I.a.609 | Cl | F | F | H | F | CH$_3$ | | —(CH$_2$)$_3$— |
| I.a.610 | F | Cl | F | H | F | CH$_3$ | | —(CH$_2$)$_3$— |
| I.a.611 | Cl | F | F | H | F | CH$_3$ | | —(CH$_2$)$_3$— |
| I.a.612 | CN | F | F | H | F | CH$_3$ | | —(CH$_2$)$_3$— |
| I.a.613 | F | CN | F | H | F | CH$_3$ | | —(CH$_2$)$_3$— |
| I.a.614 | CN | F | F | H | F | CH$_3$ | | —(CH$_2$)$_3$— |
| I.a.615 | F | F | H | F | F | CH$_3$ | | —(CH$_2$)$_3$— |
| I.a.616 | Cl | F | H | F | F | CH$_3$ | | —(CH$_2$)$_3$— |
| I.a.617 | F | Cl | H | F | F | CH$_3$ | | —(CH$_2$)$_3$— |
| I.a.618 | CN | F | H | F | F | CH$_3$ | | —(CH$_2$)$_3$— |
| I.a.619 | F | CN | H | F | F | CH$_3$ | | —(CH$_2$)$_3$— |
| I.a.620 | F | F | F | F | F | CH$_3$ | | —(CH$_2$)$_3$— |
| I.a.621 | Cl | F | F | F | F | CH$_3$ | | —(CH$_2$)$_3$— |
| I.a.622 | F | Cl | F | F | F | CH$_3$ | | —(CH$_2$)$_3$— |
| I.a.623 | CN | F | F | F | F | CH$_3$ | | —(CH$_2$)$_3$— |
| I.a.624 | F | CN | F | F | F | CH$_3$ | | —(CH$_2$)$_3$— |
| I.a.625 | H | F | F | F | F | CH$_3$ | | —(CH$_2$)$_3$— |
| I.a.626 | F | F | Br | F | F | CH$_3$ | | —(CH$_2$)$_3$— |
| I.a.627 | F | F | C≡CH | F | F | CH$_3$ | | —(CH$_2$)$_3$— |
| I.a.628 | CF$_3$ | Cl | H | H | F | CH$_3$ | | —(CH$_2$)$_3$— |
| I.a.629 | F | F | I | F | F | CH$_3$ | | —(CH$_2$)$_3$— |
| I.a.630 | F | H | H | H | F | CH$_3$ | | —(CH$_2$)$_4$— |
| I.a.631 | Cl | H | H | H | F | CH$_3$ | | —(CH$_2$)$_4$— |
| I.a.632 | Br | H | H | H | F | CH$_3$ | | —(CH$_2$)$_4$— |
| I.a.633 | CN | H | H | H | F | CH$_3$ | | —(CH$_2$)$_4$— |
| I.a.634 | CH$_3$ | H | H | H | F | CH$_3$ | | —(CH$_2$)$_4$— |
| I.a.635 | F | H | H | F | F | CH$_3$ | | —(CH$_2$)$_4$— |
| I.a.636 | Cl | H | H | F | F | CH$_3$ | | —(CH$_2$)$_4$— |
| I.a.637 | F | H | H | Cl | F | CH$_3$ | | —(CH$_2$)$_4$— |
| I.a.638 | Cl | H | H | F | F | CH$_3$ | | —(CH$_2$)$_4$— |
| I.a.639 | CN | H | H | F | F | CH$_3$ | | —(CH$_2$)$_4$— |
| I.a.640 | F | H | H | CN | F | CH$_3$ | | —(CH$_2$)$_4$— |
| I.a.641 | CN | H | H | F | F | CH$_3$ | | —(CH$_2$)$_4$— |
| I.a.642 | F | H | F | H | F | CH$_3$ | | —(CH$_2$)$_4$— |
| I.a.643 | Cl | H | F | H | F | CH$_3$ | | —(CH$_2$)$_4$— |
| I.a.644 | CN | H | F | H | F | CH$_3$ | | —(CH$_2$)$_4$— |
| I.a.645 | F | F | F | H | F | CH$_3$ | | —(CH$_2$)$_4$— |
| I.a.646 | Cl | F | F | H | F | CH$_3$ | | —(CH$_2$)$_4$— |
| I.a.647 | F | Cl | F | H | F | CH$_3$ | | —(CH$_2$)$_4$— |
| I.a.648 | Cl | F | F | H | F | CH$_3$ | | —(CH$_2$)$_4$— |
| I.a.649 | CN | F | F | H | F | CH$_3$ | | —(CH$_2$)$_4$— |
| I.a.650 | F | CN | F | H | F | CH$_3$ | | —(CH$_2$)$_4$— |
| I.a.651 | CN | F | F | H | F | CH$_3$ | | —(CH$_2$)$_4$— |
| I.a.652 | F | F | H | F | F | CH$_3$ | | —(CH$_2$)$_4$— |
| I.a.653 | Cl | F | H | F | F | CH$_3$ | | —(CH$_2$)$_4$— |
| I.a.654 | F | Cl | H | F | F | CH$_3$ | | —(CH$_2$)$_4$— |
| I.a.655 | CN | F | H | F | F | CH$_3$ | | —(CH$_2$)$_4$— |
| I.a.656 | F | CN | H | F | F | CH$_3$ | | —(CH$_2$)$_4$— |
| I.a.657 | F | F | F | F | F | CH$_3$ | | —(CH$_2$)$_4$— |
| I.a.658 | Cl | F | F | F | F | CH$_3$ | | —(CH$_2$)$_4$— |
| I.a.659 | F | Cl | F | F | F | CH$_3$ | | —(CH$_2$)$_4$— |
| I.a.660 | CN | F | F | F | F | CH$_3$ | | —(CH$_2$)$_4$— |
| I.a.661 | F | CN | F | F | F | CH$_3$ | | —(CH$_2$)$_4$— |
| I.a.662 | H | F | F | F | F | CH$_3$ | | —(CH$_2$)$_4$— |
| I.a.663 | F | F | Br | F | F | CH$_3$ | | —(CH$_2$)$_4$— |
| I.a.664 | F | F | C≡CH | F | F | CH$_3$ | | —(CH$_2$)$_4$— |
| I.a.665 | CF$_3$ | Cl | H | H | F | CH$_3$ | | —(CH$_2$)$_4$— |
| I.a.666 | F | F | I | F | F | CH$_3$ | | —(CH$_2$)$_4$— |
| I.a.667 | F | H | H | H | F | CH$_3$ | | —(CH$_2$)$_5$— |
| I.a.668 | Cl | H | H | H | F | CH$_3$ | | —(CH$_2$)$_5$— |
| I.a.669 | Br | H | H | H | F | CH$_3$ | | —(CH$_2$)$_5$— |
| I.a.670 | CN | H | H | H | F | CH$_3$ | | —(CH$_2$)$_5$— |
| I.a.671 | CH$_3$ | H | H | H | F | CH$_3$ | | —(CH$_2$)$_5$— |
| I.a.672 | F | H | H | F | F | CH$_3$ | | —(CH$_2$)$_5$— |
| I.a.673 | Cl | H | H | F | F | CH$_3$ | | —(CH$_2$)$_5$— |
| I.a.674 | F | H | H | Cl | F | CH$_3$ | | —(CH$_2$)$_5$— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.675 | Cl | H | H | F | F | $CH_3$ | | $-(CH_2)_5-$ |
| I.a.676 | CN | H | H | F | F | $CH_3$ | | $-(CH_2)_5-$ |
| I.a.677 | F | H | H | CN | F | $CH_3$ | | $-(CH_2)_5-$ |
| I.a.678 | CN | H | H | F | F | $CH_3$ | | $-(CH_2)_5-$ |
| I.a.679 | F | H | F | H | F | $CH_3$ | | $-(CH_2)_5-$ |
| I.a.680 | Cl | H | F | H | F | $CH_3$ | | $-(CH_2)_5-$ |
| I.a.681 | CN | H | F | H | F | $CH_3$ | | $-(CH_2)_5-$ |
| I.a.682 | F | F | F | H | F | $CH_3$ | | $-(CH_2)_5-$ |
| I.a.683 | Cl | F | F | H | F | $CH_3$ | | $-(CH_2)_5-$ |
| I.a.684 | F | Cl | F | H | F | $CH_3$ | | $-(CH_2)_5-$ |
| I.a.685 | Cl | F | F | H | F | $CH_3$ | | $-(CH_2)_5-$ |
| I.a.686 | CN | F | F | H | F | $CH_3$ | | $-(CH_2)_5-$ |
| I.a.687 | F | CN | F | H | F | $CH_3$ | | $-(CH_2)_5-$ |
| I.a.688 | CN | F | F | H | F | $CH_3$ | | $-(CH_2)_5-$ |
| I.a.689 | F | F | F | H | F | $CH_3$ | | $-(CH_2)_5-$ |
| I.a.690 | Cl | F | H | F | F | $CH_3$ | | $-(CH_2)_5-$ |
| I.a.691 | F | Cl | H | F | F | $CH_3$ | | $-(CH_2)_5-$ |
| I.a.692 | CN | F | H | F | F | $CH_3$ | | $-(CH_2)_5-$ |
| I.a.693 | F | CN | H | F | F | $CH_3$ | | $-(CH_2)_5-$ |
| I.a.694 | F | F | F | F | F | $CH_3$ | | $-(CH_2)_5-$ |
| I.a.695 | Cl | F | F | F | F | $CH_3$ | | $-(CH_2)_5-$ |
| I.a.696 | F | Cl | F | F | F | $CH_3$ | | $-(CH_2)_5-$ |
| I.a.697 | CN | F | F | F | F | $CH_3$ | | $-(CH_2)_5-$ |
| I.a.698 | F | CN | F | F | F | $CH_3$ | | $-(CH_2)_5-$ |
| I.a.699 | H | F | F | F | F | $CH_3$ | | $-(CH_2)_5-$ |
| I.a.700 | F | F | Br | F | F | $CH_3$ | | $-(CH_2)_5-$ |
| I.a.701 | F | F | C≡CH | F | F | $CH_3$ | | $-(CH_2)_5-$ |
| I.a.702 | $CF_3$ | Cl | H | H | F | $CH_3$ | | $-(CH_2)_5-$ |
| I.a.703 | F | F | I | F | F | $CH_3$ | | $-(CH_2)_5-$ |
| I.a.704 | F | H | H | H | F | F | | $-(CH_2)_2-$ |
| I.a.705 | Cl | H | H | H | F | F | | $-(CH_2)_2-$ |
| I.a.706 | Br | H | H | H | F | F | | $-(CH_2)_2-$ |
| I.a.707 | CN | H | H | H | F | F | | $-(CH_2)_2-$ |
| I.a.708 | $CH_3$ | H | H | H | F | F | | $-(CH_2)_2-$ |
| I.a.709 | F | H | H | F | F | F | | $-(CH_2)_2-$ |
| I.a.710 | Cl | H | H | F | F | F | | $-(CH_2)_2-$ |
| I.a.711 | F | H | H | Cl | F | F | | $-(CH_2)_2-$ |
| I.a.712 | Cl | H | H | F | F | F | | $-(CH_2)_2-$ |
| I.a.713 | CN | H | H | F | F | F | | $-(CH_2)_2-$ |
| I.a.714 | F | H | H | CN | F | F | | $-(CH_2)_2-$ |
| I.a.715 | CN | H | H | F | F | F | | $-(CH_2)_2-$ |
| I.a.716 | F | H | F | H | F | F | | $-(CH_2)_2-$ |
| I.a.717 | Cl | H | F | H | F | F | | $-(CH_2)_2-$ |
| I.a.718 | CN | H | F | H | F | F | | $-(CH_2)_2-$ |
| I.a.719 | F | F | F | H | F | F | | $-(CH_2)_2-$ |
| I.a.720 | Cl | F | F | H | F | F | | $-(CH_2)_2-$ |
| I.a.721 | F | Cl | F | H | F | F | | $-(CH_2)_2-$ |
| I.a.722 | Cl | F | F | H | F | F | | $-(CH_2)_2-$ |
| I.a.723 | CN | F | F | H | F | F | | $-(CH_2)_2-$ |
| I.a.724 | F | CN | F | H | F | F | | $-(CH_2)_2-$ |
| I.a.725 | CN | F | F | H | F | F | | $-(CH_2)_2-$ |
| I.a.726 | F | F | F | H | F | F | | $-(CH_2)_2-$ |
| I.a.727 | Cl | F | H | F | F | F | | $-(CH_2)_2-$ |
| I.a.728 | F | Cl | H | F | F | F | | $-(CH_2)_2-$ |
| I.a.729 | CN | F | H | F | F | F | | $-(CH_2)_2-$ |
| I.a.730 | F | CN | H | F | F | F | | $-(CH_2)_2-$ |
| I.a.731 | F | F | F | F | F | F | | $-(CH_2)_2-$ |
| I.a.732 | Cl | F | F | F | F | F | | $-(CH_2)_2-$ |
| I.a.733 | F | Cl | F | F | F | F | | $-(CH_2)_2-$ |
| I.a.734 | CN | F | F | F | F | F | | $-(CH_2)_2-$ |
| I.a.735 | F | CN | F | F | F | F | | $-(CH_2)_2-$ |
| I.a.736 | H | F | F | F | F | F | | $-(CH_2)_2-$ |
| I.a.737 | F | F | Br | F | F | F | | $-(CH_2)_2-$ |
| I.a.738 | F | F | C≡CH | F | F | F | | $-(CH_2)_2-$ |
| I.a.739 | $CF_3$ | Cl | H | H | F | F | | $-(CH_2)_2-$ |
| I.a.740 | F | F | I | F | F | F | | $-(CH_2)_2-$ |
| I.a.741 | F | H | H | H | F | F | | $-(CH_2)_3-$ |
| I.a.742 | Cl | H | H | H | F | F | | $-(CH_2)_3-$ |
| I.a.743 | Br | H | H | H | F | F | | $-(CH_2)_3-$ |
| I.a.744 | CN | H | H | H | F | F | | $-(CH_2)_3-$ |
| I.a.745 | $CH_3$ | H | H | H | F | F | | $-(CH_2)_3-$ |
| I.a.746 | F | H | H | F | F | F | | $-(CH_2)_3-$ |
| I.a.747 | Cl | H | H | F | F | F | | $-(CH_2)_3-$ |
| I.a.748 | F | H | H | Cl | F | F | | $-(CH_2)_3-$ |
| I.a.749 | Cl | H | H | F | F | F | | $-(CH_2)_3-$ |
| I.a.750 | CN | H | H | F | F | F | | $-(CH_2)_3-$ |
| I.a.751 | F | H | H | CN | F | F | | $-(CH_2)_3-$ |
| I.a.752 | CN | H | H | F | F | F | | $-(CH_2)_3-$ |
| I.a.753 | F | H | F | H | F | F | | $-(CH_2)_3-$ |
| I.a.754 | Cl | H | F | H | F | F | | $-(CH_2)_3-$ |
| I.a.755 | CN | H | F | H | F | F | | $-(CH_2)_3-$ |
| I.a.756 | F | F | F | H | F | F | | $-(CH_2)_3-$ |
| I.a.757 | Cl | F | F | H | F | F | | $-(CH_2)_3-$ |
| I.a.758 | F | Cl | F | H | F | F | | $-(CH_2)_3-$ |
| I.a.759 | Cl | F | F | H | F | F | | $-(CH_2)_3-$ |
| I.a.760 | CN | F | F | H | F | F | | $-(CH_2)_3-$ |
| I.a.761 | F | CN | F | H | F | F | | $-(CH_2)_3-$ |
| I.a.762 | CN | F | F | H | F | F | | $-(CH_2)_3-$ |
| I.a.763 | F | F | F | H | F | F | | $-(CH_2)_3-$ |
| I.a.764 | Cl | F | H | F | F | F | | $-(CH_2)_3-$ |
| I.a.765 | F | Cl | H | F | F | F | | $-(CH_2)_3-$ |
| I.a.766 | CN | F | H | F | F | F | | $-(CH_2)_3-$ |
| I.a.767 | F | CN | H | F | F | F | | $-(CH_2)_3-$ |
| I.a.768 | F | F | F | F | F | F | | $-(CH_2)_3-$ |
| I.a.769 | Cl | F | F | F | F | F | | $-(CH_2)_3-$ |
| I.a.770 | F | Cl | F | F | F | F | | $-(CH_2)_3-$ |
| I.a.771 | F | CN | F | F | F | F | | $-(CH_2)_3-$ |
| I.a.772 | F | CN | F | F | F | F | | $-(CH_2)_3-$ |
| I.a.773 | H | F | F | F | F | F | | $-(CH_2)_3-$ |
| I.a.774 | F | F | Br | F | F | F | | $-(CH_2)_3-$ |
| I.a.775 | F | F | C≡CH | F | F | F | | $-(CH_2)_3-$ |
| I.a.776 | $CF_3$ | Cl | H | H | F | F | | $-(CH_2)_3-$ |
| I.a.777 | F | F | I | F | F | F | | $-(CH_2)_3-$ |
| I.a.778 | F | H | H | H | F | F | | $-(CH_2)_4-$ |
| I.a.779 | F | H | H | H | F | F | | $-(CH_2)_4-$ |
| I.a.780 | Br | H | H | H | F | F | | $-(CH_2)_4-$ |
| I.a.781 | CN | H | H | H | F | F | | $-(CH_2)_4-$ |
| I.a.782 | $CH_3$ | H | H | H | F | F | | $-(CH_2)_4-$ |
| I.a.783 | F | H | H | F | F | F | | $-(CH_2)_4-$ |
| I.a.784 | Cl | H | H | F | F | F | | $-(CH_2)_4-$ |
| I.a.785 | F | H | H | Cl | F | F | | $-(CH_2)_4-$ |
| I.a.786 | Cl | H | H | F | F | F | | $-(CH_2)_4-$ |
| I.a.787 | CN | H | H | F | F | F | | $-(CH_2)_4-$ |
| I.a.788 | F | H | H | CN | F | F | | $-(CH_2)_4-$ |
| I.a.789 | CN | H | H | F | F | F | | $-(CH_2)_4-$ |
| I.a.790 | F | H | F | H | F | F | | $-(CH_2)_4-$ |
| I.a.791 | Cl | H | F | H | F | F | | $-(CH_2)_4-$ |
| I.a.792 | CN | H | F | H | F | F | | $-(CH_2)_4-$ |
| I.a.793 | F | F | F | H | F | F | | $-(CH_2)_4-$ |
| I.a.794 | Cl | F | F | H | F | F | | $-(CH_2)_4-$ |
| I.a.795 | F | Cl | F | H | F | F | | $-(CH_2)_4-$ |
| I.a.796 | Cl | F | F | H | F | F | | $-(CH_2)_4-$ |
| I.a.797 | CN | F | F | H | F | F | | $-(CH_2)_4-$ |
| I.a.798 | F | CN | F | H | F | F | | $-(CH_2)_4-$ |
| I.a.799 | CN | F | F | H | F | F | | $-(CH_2)_4-$ |
| I.a.800 | F | F | F | H | F | F | | $-(CH_2)_4-$ |
| I.a.801 | Cl | F | H | F | F | F | | $-(CH_2)_4-$ |
| I.a.802 | F | Cl | H | F | F | F | | $-(CH_2)_4-$ |
| I.a.803 | CN | F | H | F | F | F | | $-(CH_2)_4-$ |
| I.a.804 | F | CN | H | F | F | F | | $-(CH_2)_4-$ |
| I.a.805 | F | H | H | F | F | F | | $-(CH_2)_4-$ |
| I.a.806 | Cl | F | F | F | F | F | | $-(CH_2)_4-$ |
| I.a.807 | F | Cl | F | F | F | F | | $-(CH_2)_4-$ |
| I.a.808 | CN | F | F | F | F | F | | $-(CH_2)_4-$ |
| I.a.809 | F | CN | F | F | F | F | | $-(CH_2)_4-$ |
| I.a.810 | H | F | F | F | F | F | | $-(CH_2)_4-$ |
| I.a.811 | F | F | Br | F | F | F | | $-(CH_2)_4-$ |
| I.a.812 | F | F | C≡CH | F | F | F | | $-(CH_2)_4-$ |
| I.a.813 | $CF_3$ | Cl | H | H | F | F | | $-(CH_2)_4-$ |
| I.a.814 | F | F | I | F | F | F | | $-(CH_2)_4-$ |
| I.a.815 | F | H | H | H | F | F | | $-(CH_2)_5-$ |
| I.a.816 | Cl | H | H | H | F | F | | $-(CH_2)_5-$ |
| I.a.817 | Br | H | H | H | F | F | | $-(CH_2)_5-$ |
| I.a.818 | CN | H | H | H | F | F | | $-(CH_2)_5-$ |
| I.a.819 | $CH_3$ | H | H | H | F | F | | $-(CH_2)_5-$ |
| I.a.820 | F | H | H | F | F | F | | $-(CH_2)_5-$ |
| I.a.821 | Cl | H | H | Br | F | F | | $-(CH_2)_5-$ |
| I.a.822 | F | H | H | Cl | F | F | | $-(CH_2)_5-$ |
| I.a.823 | Cl | H | H | F | F | F | | $-(CH_2)_5-$ |
| I.a.824 | CN | H | H | F | F | F | | $-(CH_2)_5-$ |
| I.a.825 | F | H | H | CN | F | F | | $-(CH_2)_5-$ |
| I.a.826 | CN | H | H | F | F | F | | $-(CH_2)_5-$ |
| I.a.827 | F | H | F | H | F | F | | $-(CH_2)_5-$ |
| I.a.828 | Cl | H | F | H | F | F | | $-(CH_2)_5-$ |
| I.a.829 | CN | H | F | H | F | F | | $-(CH_2)_5-$ |
| I.a.830 | F | F | F | H | F | F | | $-(CH_2)_5-$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.831 | Cl | F | F | H | F | F | | —(CH$_2$)$_5$— |
| I.a.832 | F | Cl | F | H | F | F | | —(CH$_2$)$_5$— |
| I.a.833 | Cl | F | F | H | F | F | | —(CH$_2$)$_5$— |
| I.a.834 | CN | F | F | H | F | F | | —(CH$_2$)$_5$— |
| I.a.835 | F | CN | F | H | F | F | | —(CH$_2$)$_5$— |
| I.a.836 | CN | F | F | H | F | F | | —(CH$_2$)$_5$— |
| I.a.837 | F | F | H | F | F | F | | —(CH$_2$)$_5$— |
| I.a.838 | Cl | F | H | F | F | F | | —(CH$_2$)$_5$— |
| I.a.839 | F | Cl | H | F | F | F | | —(CH$_2$)$_5$— |
| I.a.840 | CN | F | H | F | F | F | | —(CH$_2$)$_5$— |
| I.a.841 | F | CN | H | F | F | F | | —(CH$_2$)$_5$— |
| I.a.842 | F | F | F | F | F | F | | —(CH$_2$)$_5$— |
| I.a.843 | Cl | F | F | F | F | F | | —(CH$_2$)$_5$— |
| I.a.844 | F | Cl | F | F | F | F | | —(CH$_2$)$_5$— |
| I.a.845 | CN | F | F | F | F | F | | —(CH$_2$)$_5$— |
| I.a.846 | F | CN | F | F | F | F | | —(CH$_2$)$_5$— |
| I.a.847 | H | F | F | F | F | F | | —(CH$_2$)$_5$— |
| I.a.848 | F | F | Br | F | F | F | | —(CH$_2$)$_5$— |
| I.a.849 | F | F | C≡CH | F | F | F | | —(CH$_2$)$_5$— |
| I.a.850 | CF$_3$ | Cl | H | H | F | F | | —(CH$_2$)$_5$— |
| I.a.851 | F | F | I | F | F | F | | —(CH$_2$)$_5$— |
| I.a.852 | F | H | H | H | F | Cl | | —(CH$_2$)$_2$— |
| I.a.853 | Cl | H | H | H | F | Cl | | —(CH$_2$)$_2$— |
| I.a.854 | Br | H | H | H | F | Cl | | —(CH$_2$)$_2$— |
| I.a.855 | CN | H | H | H | F | Cl | | —(CH$_2$)$_2$— |
| I.a.856 | CH$_3$ | H | H | H | F | Cl | | —(CH$_2$)$_2$— |
| I.a.857 | F | H | H | F | F | Cl | | —(CH$_2$)$_2$— |
| I.a.858 | Cl | H | H | F | F | Cl | | —(CH$_2$)$_2$— |
| I.a.859 | F | H | H | Cl | F | Cl | | —(CH$_2$)$_2$— |
| I.a.860 | Cl | H | H | F | F | Cl | | —(CH$_2$)$_2$— |
| I.a.861 | CN | H | H | F | F | Cl | | —(CH$_2$)$_2$— |
| I.a.862 | F | H | H | CN | F | Cl | | —(CH$_2$)$_2$— |
| I.a.863 | CN | H | H | F | F | Cl | | —(CH$_2$)$_2$— |
| I.a.864 | F | H | F | H | F | Cl | | —(CH$_2$)$_2$— |
| I.a.865 | Cl | H | F | H | F | Cl | | —(CH$_2$)$_2$— |
| I.a.866 | CN | H | F | H | F | Cl | | —(CH$_2$)$_2$— |
| I.a.867 | F | F | F | H | F | Cl | | —(CH$_2$)$_2$— |
| I.a.868 | Cl | F | F | H | F | Cl | | —(CH$_2$)$_2$— |
| I.a.869 | F | Cl | F | H | F | Cl | | —(CH$_2$)$_2$— |
| I.a.870 | Cl | F | F | H | F | Cl | | —(CH$_2$)$_2$— |
| I.a.871 | CN | F | F | H | F | Cl | | —(CH$_2$)$_2$— |
| I.a.872 | F | CN | F | H | F | Cl | | —(CH$_2$)$_2$— |
| I.a.873 | CN | F | F | H | F | Cl | | —(CH$_2$)$_2$— |
| I.a.874 | F | F | H | F | F | Cl | | —(CH$_2$)$_2$— |
| I.a.875 | Cl | F | H | F | F | Cl | | —(CH$_2$)$_2$— |
| I.a.876 | F | Cl | H | F | F | Cl | | —(CH$_2$)$_2$— |
| I.a.877 | CN | F | H | F | F | Cl | | —(CH$_2$)$_2$— |
| I.a.878 | F | CN | H | F | F | Cl | | —(CH$_2$)$_2$— |
| I.a.879 | F | F | F | F | F | Cl | | —(CH$_2$)$_2$— |
| I.a.880 | Cl | F | F | F | F | Cl | | —(CH$_2$)$_2$— |
| I.a.881 | F | Cl | F | F | F | Cl | | —(CH$_2$)$_2$— |
| I.a.882 | CN | F | F | F | F | Cl | | —(CH$_2$)$_2$— |
| I.a.883 | F | CN | F | F | F | Cl | | —(CH$_2$)$_2$— |
| I.a.884 | H | F | F | F | F | Cl | | —(CH$_2$)$_2$— |
| I.a.885 | F | F | Br | F | F | Cl | | —(CH$_2$)$_2$— |
| I.a.886 | F | F | C≡CH | F | F | Cl | | —(CH$_2$)$_2$— |
| I.a.887 | CF$_3$ | Cl | H | H | F | Cl | | —(CH$_2$)$_2$— |
| I.a.888 | F | F | I | F | F | Cl | | —(CH$_2$)$_2$— |
| I.a.889 | F | H | H | H | F | Cl | | —(CH$_2$)$_3$— |
| I.a.890 | Cl | H | H | H | F | Cl | | —(CH$_2$)$_3$— |
| I.a.891 | Br | H | H | H | F | Cl | | —(CH$_2$)$_3$— |
| I.a.892 | CN | H | H | H | F | Cl | | —(CH$_2$)$_3$— |
| I.a.893 | CH$_3$ | H | H | H | F | Cl | | —(CH$_2$)$_3$— |
| I.a.894 | F | H | H | F | F | Cl | | —(CH$_2$)$_3$— |
| I.a.895 | Cl | H | H | F | F | Cl | | —(CH$_2$)$_3$— |
| I.a.896 | F | H | H | Cl | F | Cl | | —(CH$_2$)$_3$— |
| I.a.897 | Cl | H | H | F | F | Cl | | —(CH$_2$)$_3$— |
| I.a.898 | CN | H | H | F | F | Cl | | —(CH$_2$)$_3$— |
| I.a.899 | F | H | H | CN | F | Cl | | —(CH$_2$)$_3$— |
| I.a.900 | CN | H | H | F | F | Cl | | —(CH$_2$)$_3$— |
| I.a.901 | F | H | F | H | F | Cl | | —(CH$_2$)$_3$— |
| I.a.902 | Cl | H | F | H | F | Cl | | —(CH$_2$)$_3$— |
| I.a.903 | CN | H | F | H | F | Cl | | —(CH$_2$)$_3$— |
| I.a.904 | F | F | F | H | F | Cl | | —(CH$_2$)$_3$— |
| I.a.905 | Cl | F | F | H | F | Cl | | —(CH$_2$)$_3$— |
| I.a.906 | F | Cl | F | H | F | Cl | | —(CH$_2$)$_3$— |
| I.a.907 | Cl | F | F | H | F | Cl | | —(CH$_2$)$_3$— |
| I.a.908 | CN | F | F | H | F | Cl | | —(CH$_2$)$_3$— |
| I.a.909 | F | CN | F | H | F | Cl | | —(CH$_2$)$_3$— |
| I.a.910 | CN | F | F | H | F | Cl | | —(CH$_2$)$_3$— |
| I.a.911 | F | F | H | F | F | Cl | | —(CH$_2$)$_3$— |
| I.a.912 | Cl | F | H | F | F | Cl | | —(CH$_2$)$_3$— |
| I.a.913 | F | Cl | H | F | F | Cl | | —(CH$_2$)$_3$— |
| I.a.914 | CN | F | H | F | F | Cl | | —(CH$_2$)$_3$— |
| I.a.915 | F | CN | H | F | F | Cl | | —(CH$_2$)$_3$— |
| I.a.916 | F | F | F | F | F | Cl | | —(CH$_2$)$_3$— |
| I.a.917 | Cl | F | F | F | F | Cl | | —(CH$_2$)$_3$— |
| I.a.918 | F | Cl | F | F | F | Cl | | —(CH$_2$)$_3$— |
| I.a.919 | CN | F | F | F | F | Cl | | —(CH$_2$)$_3$— |
| I.a.920 | F | CN | F | F | F | Cl | | —(CH$_2$)$_3$— |
| I.a.921 | H | F | F | F | F | Cl | | —(CH$_2$)$_3$— |
| I.a.922 | F | F | Br | F | F | Cl | | —(CH$_2$)$_3$— |
| I.a.923 | F | F | C≡CH | F | F | Cl | | —(CH$_2$)$_3$— |
| I.a.924 | CF$_3$ | Cl | H | H | F | Cl | | —(CH$_2$)$_3$— |
| I.a.925 | F | F | I | F | F | Cl | | —(CH$_2$)$_3$— |
| I.a.926 | F | H | H | H | F | Cl | | —(CH$_2$)$_4$— |
| I.a.927 | Cl | H | H | H | F | Cl | | —(CH$_2$)$_4$— |
| I.a.928 | Br | H | H | H | F | Cl | | —(CH$_2$)$_4$— |
| I.a.929 | CN | H | H | H | F | Cl | | —(CH$_2$)$_4$— |
| I.a.930 | CH$_3$ | H | H | H | F | Cl | | —(CH$_2$)$_4$— |
| I.a.931 | F | H | H | F | F | Cl | | —(CH$_2$)$_4$— |
| I.a.932 | Cl | H | H | F | F | Cl | | —(CH$_2$)$_4$— |
| I.a.933 | F | H | H | Cl | F | Cl | | —(CH$_2$)$_4$— |
| I.a.934 | Cl | H | H | F | F | Cl | | —(CH$_2$)$_4$— |
| I.a.935 | CN | H | H | F | F | Cl | | —(CH$_2$)$_4$— |
| I.a.936 | F | H | H | CN | F | Cl | | —(CH$_2$)$_4$— |
| I.a.937 | CN | H | H | F | F | Cl | | —(CH$_2$)$_4$— |
| I.a.938 | F | H | F | H | F | Cl | | —(CH$_2$)$_4$— |
| I.a.939 | Cl | H | F | H | F | Cl | | —(CH$_2$)$_4$— |
| I.a.940 | CN | H | F | H | F | Cl | | —(CH$_2$)$_4$— |
| I.a.941 | F | F | F | H | F | Cl | | —(CH$_2$)$_4$— |
| I.a.942 | Cl | F | F | H | F | Cl | | —(CH$_2$)$_4$— |
| I.a.943 | F | Cl | F | H | F | Cl | | —(CH$_2$)$_4$— |
| I.a.944 | Cl | F | F | H | F | Cl | | —(CH$_2$)$_4$— |
| I.a.945 | CN | F | F | H | F | Cl | | —(CH$_2$)$_4$— |
| I.a.946 | F | CN | F | H | F | Cl | | —(CH$_2$)$_4$— |
| I.a.947 | CN | F | F | H | F | Cl | | —(CH$_2$)$_4$— |
| I.a.948 | F | F | H | F | F | Cl | | —(CH$_2$)$_4$— |
| I.a.949 | Cl | F | H | F | F | Cl | | —(CH$_2$)$_4$— |
| I.a.950 | F | Cl | H | F | F | Cl | | —(CH$_2$)$_4$— |
| I.a.951 | CN | F | H | F | F | Cl | | —(CH$_2$)$_4$— |
| I.a.952 | F | CN | H | F | F | Cl | | —(CH$_2$)$_4$— |
| I.a.953 | F | F | F | F | F | Cl | | —(CH$_2$)$_4$— |
| I.a.954 | Cl | F | F | F | F | Cl | | —(CH$_2$)$_4$— |
| I.a.955 | F | Cl | F | F | F | Cl | | —(CH$_2$)$_4$— |
| I.a.956 | CN | F | F | F | F | Cl | | —(CH$_2$)$_4$— |
| I.a.957 | F | CN | F | F | F | Cl | | —(CH$_2$)$_4$— |
| I.a.958 | H | F | F | F | F | Cl | | —(CH$_2$)$_4$— |
| I.a.959 | F | F | Br | F | F | Cl | | —(CH$_2$)$_4$— |
| I.a.960 | F | F | C≡CH | F | F | Cl | | —(CH$_2$)$_4$— |
| I.a.961 | CF$_3$ | Cl | H | H | F | Cl | | —(CH$_2$)$_4$— |
| I.a.962 | F | F | I | F | F | Cl | | —(CH$_2$)$_4$— |
| I.a.963 | F | H | H | H | F | Cl | | —(CH$_2$)$_5$— |
| I.a.964 | Cl | H | H | H | F | Cl | | —(CH$_2$)$_5$— |
| I.a.965 | Br | H | H | H | F | Cl | | —(CH$_2$)$_5$— |
| I.a.966 | CN | H | H | H | F | Cl | | —(CH$_2$)$_5$— |
| I.a.967 | CH$_3$ | H | H | H | F | Cl | | —(CH$_2$)$_5$— |
| I.a.968 | F | H | H | F | F | Cl | | —(CH$_2$)$_5$— |
| I.a.969 | Cl | H | H | F | F | Cl | | —(CH$_2$)$_5$— |
| I.a.970 | F | H | H | Cl | F | Cl | | —(CH$_2$)$_5$— |
| I.a.971 | Cl | H | H | F | F | Cl | | —(CH$_2$)$_5$— |
| I.a.972 | CN | H | H | F | F | Cl | | —(CH$_2$)$_5$— |
| I.a.973 | F | H | H | CN | F | Cl | | —(CH$_2$)$_5$— |
| I.a.974 | CN | H | H | F | F | Cl | | —(CH$_2$)$_5$— |
| I.a.975 | F | H | F | H | F | Cl | | —(CH$_2$)$_5$— |
| I.a.976 | Cl | H | F | H | F | Cl | | —(CH$_2$)$_5$— |
| I.a.977 | CN | H | F | H | F | Cl | | —(CH$_2$)$_5$— |
| I.a.978 | F | F | F | H | F | Cl | | —(CH$_2$)$_5$— |
| I.a.979 | Cl | F | F | H | F | Cl | | —(CH$_2$)$_5$— |
| I.a.980 | F | Cl | F | H | F | Cl | | —(CH$_2$)$_5$— |
| I.a.981 | Cl | F | F | H | F | Cl | | —(CH$_2$)$_5$— |
| I.a.982 | CN | F | F | H | F | Cl | | —(CH$_2$)$_5$— |
| I.a.983 | F | CN | F | H | F | Cl | | —(CH$_2$)$_5$— |
| I.a.984 | CN | F | F | H | F | Cl | | —(CH$_2$)$_5$— |
| I.a.985 | F | F | H | F | F | Cl | | —(CH$_2$)$_5$— |
| I.a.986 | Cl | F | H | F | F | Cl | | —(CH$_2$)$_5$— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.987 | F | Cl | H | F | F | Cl | —(CH$_2$)$_5$— | |
| I.a.988 | CN | F | H | F | F | Cl | —(CH$_2$)$_5$— | |
| I.a.989 | F | CN | H | F | F | Cl | —(CH$_2$)$_5$— | |
| I.a.990 | F | F | F | F | F | Cl | —(CH$_2$)$_5$— | |
| I.a.991 | Cl | F | F | F | F | Cl | —(CH$_2$)$_5$— | |
| I.a.992 | F | Cl | F | F | F | Cl | —(CH$_2$)$_5$— | |
| I.a.993 | CN | F | F | F | F | Cl | —(CH$_2$)$_5$— | |
| I.a.994 | F | CN | F | F | F | Cl | —(CH$_2$)$_5$— | |
| I.a.995 | H | F | F | F | F | Cl | —(CH$_2$)$_5$— | |
| I.a.996 | F | F | Br | F | F | Cl | —(CH$_2$)$_5$— | |
| I.a.997 | F | F | C≡CH | F | F | Cl | —(CH$_2$)$_5$— | |
| I.a.998 | CF$_3$ | Cl | H | H | F | Cl | —(CH$_2$)$_5$— | |
| I.a.999 | F | F | I | F | F | Cl | —(CH$_2$)$_5$— | |
| I.a.1000 | F | H | H | H | F | C$_2$H$_5$ | CH$_3$ | H |
| I.a.1001 | Cl | H | H | H | F | C$_2$H$_5$ | CH$_3$ | H |
| I.a.1002 | Br | H | H | H | F | C$_2$H$_5$ | CH$_3$ | H |
| I.a.1003 | CN | H | H | H | F | C$_2$H$_5$ | CH$_3$ | H |
| I.a.1004 | CH$_3$ | H | H | H | F | C$_2$H$_5$ | CH$_3$ | H |
| I.a.1005 | F | H | H | F | F | C$_2$H$_5$ | CH$_3$ | H |
| I.a.1006 | Cl | H | H | F | F | C$_2$H$_5$ | CH$_3$ | H |
| I.a.1007 | F | H | H | Cl | F | C$_2$H$_5$ | CH$_3$ | H |
| I.a.1008 | Cl | H | H | F | F | C$_2$H$_5$ | CH$_3$ | H |
| I.a.1009 | CN | H | H | F | F | C$_2$H$_5$ | CH$_3$ | H |
| I.a.1010 | F | H | H | CN | F | C$_2$H$_5$ | CH$_3$ | H |
| I.a.1011 | CN | H | H | F | F | C$_2$H$_5$ | CH$_3$ | H |
| I.a.1012 | F | H | F | H | F | C$_2$H$_5$ | CH$_3$ | H |
| I.a.1013 | Cl | H | F | H | F | C$_2$H$_5$ | CH$_3$ | H |
| I.a.1014 | CN | H | F | H | F | C$_2$H$_5$ | CH$_3$ | H |
| I.a.1015 | F | F | F | H | F | C$_2$H$_5$ | CH$_3$ | H |
| I.a.1016 | Cl | F | F | H | F | C$_2$H$_5$ | CH$_3$ | H |
| I.a.1017 | F | Cl | F | H | F | C$_2$H$_5$ | CH$_3$ | H |
| I.a.1018 | Cl | F | F | H | F | C$_2$H$_5$ | CH$_3$ | H |
| I.a.1019 | CN | F | F | H | F | C$_2$H$_5$ | CH$_3$ | H |
| I.a.1020 | F | CN | F | H | F | C$_2$H$_5$ | CH$_3$ | H |
| I.a.1021 | CN | F | F | H | F | C$_2$H$_5$ | CH$_3$ | H |
| I.a.1022 | F | F | H | F | F | C$_2$H$_5$ | CH$_3$ | H |
| I.a.1023 | Cl | F | H | F | F | C$_2$H$_5$ | CH$_3$ | H |
| I.a.1024 | F | Cl | H | F | F | C$_2$H$_5$ | CH$_3$ | H |
| I.a.1025 | CN | F | H | F | F | C$_2$H$_5$ | CH$_3$ | H |
| I.a.1026 | F | CN | H | F | F | C$_2$H$_5$ | CH$_3$ | H |
| I.a.1027 | F | F | F | F | F | C$_2$H$_5$ | CH$_3$ | H |
| I.a.1028 | Cl | F | F | F | F | C$_2$H$_5$ | CH$_3$ | H |
| I.a.1029 | F | Cl | F | F | F | C$_2$H$_5$ | CH$_3$ | H |
| I.a.1030 | CN | F | F | F | F | C$_2$H$_5$ | CH$_3$ | H |
| I.a.1031 | F | CN | F | F | F | C$_2$H$_5$ | CH$_3$ | H |
| I.a.1032 | H | F | F | F | F | C$_2$H$_5$ | CH$_3$ | H |
| I.a.1033 | F | F | Br | F | F | C$_2$H$_5$ | CH$_3$ | H |
| I.a.1034 | F | F | C≡CH | F | F | C$_2$H$_5$ | CH$_3$ | H |
| I.a.1035 | CF$_3$ | Cl | H | H | F | C$_2$H$_5$ | CH$_3$ | H |
| I.a.1036 | F | F | I | F | F | C$_2$H$_5$ | CH$_3$ | H |
| I.a.1037 | F | H | H | H | F | C$_2$H$_5$ | C$_2$H$_5$ | H |
| I.a.1038 | Cl | H | H | H | F | C$_2$H$_5$ | C$_2$H$_5$ | H |
| I.a.1039 | Br | H | H | H | F | C$_2$H$_5$ | C$_2$H$_5$ | H |
| I.a.1040 | CN | H | H | H | F | C$_2$H$_5$ | C$_2$H$_5$ | H |
| I.a.1041 | CH$_3$ | H | H | H | F | C$_2$H$_5$ | C$_2$H$_5$ | H |
| I.a.1042 | F | H | H | F | F | C$_2$H$_5$ | C$_2$H$_5$ | H |
| I.a.1043 | Cl | H | H | F | F | C$_2$H$_5$ | C$_2$H$_5$ | H |
| I.a.1044 | F | H | H | Cl | F | C$_2$H$_5$ | C$_2$H$_5$ | H |
| I.a.1045 | Cl | H | H | F | F | C$_2$H$_5$ | C$_2$H$_5$ | H |
| I.a.1046 | CN | H | H | F | F | C$_2$H$_5$ | C$_2$H$_5$ | H |
| I.a.1047 | F | H | H | CN | F | C$_2$H$_5$ | C$_2$H$_5$ | H |
| I.a.1048 | CN | H | H | F | F | C$_2$H$_5$ | C$_2$H$_5$ | H |
| I.a.1049 | F | H | F | H | F | C$_2$H$_5$ | C$_2$H$_5$ | H |
| I.a.1050 | Cl | H | F | H | F | C$_2$H$_5$ | C$_2$H$_5$ | H |
| I.a.1051 | CN | H | F | H | F | C$_2$H$_5$ | C$_2$H$_5$ | H |
| I.a.1052 | F | F | F | H | F | C$_2$H$_5$ | C$_2$H$_5$ | H |
| I.a.1053 | Cl | F | F | H | F | C$_2$H$_5$ | C$_2$H$_5$ | H |
| I.a.1054 | F | Cl | F | H | F | C$_2$H$_5$ | C$_2$H$_5$ | H |
| I.a.1055 | Cl | F | F | H | F | C$_2$H$_5$ | C$_2$H$_5$ | H |
| I.a.1056 | CN | F | F | H | F | C$_2$H$_5$ | C$_2$H$_5$ | H |
| I.a.1057 | F | CN | F | H | F | C$_2$H$_5$ | C$_2$H$_5$ | H |
| I.a.1058 | CN | F | F | H | F | C$_2$H$_5$ | C$_2$H$_5$ | H |
| I.a.1059 | F | F | H | F | F | C$_2$H$_5$ | C$_2$H$_5$ | H |
| I.a.1060 | Cl | F | H | F | F | C$_2$H$_5$ | C$_2$H$_5$ | H |
| I.a.1061 | F | Cl | H | F | F | C$_2$H$_5$ | C$_2$H$_5$ | H |
| I.a.1062 | CN | F | H | F | F | C$_2$H$_5$ | C$_2$H$_5$ | H |
| I.a.1063 | F | CN | H | F | F | C$_2$H$_5$ | C$_2$H$_5$ | H |
| I.a.1064 | F | F | F | F | F | C$_2$H$_5$ | C$_2$H$_5$ | H |
| I.a.1065 | Cl | F | F | F | F | C$_2$H$_5$ | C$_2$H$_5$ | H |
| I.a.1066 | F | Cl | F | F | F | C$_2$H$_5$ | C$_2$H$_5$ | H |
| I.a.1067 | CN | F | F | F | F | C$_2$H$_5$ | C$_2$H$_5$ | H |
| I.a.1068 | F | CN | F | F | F | C$_2$H$_5$ | C$_2$H$_5$ | H |
| I.a.1069 | H | F | F | F | F | C$_2$H$_5$ | C$_2$H$_5$ | H |
| I.a.1070 | F | F | Br | F | F | C$_2$H$_5$ | C$_2$H$_5$ | H |
| I.a.1071 | F | F | C≡CH | F | F | C$_2$H$_5$ | C$_2$H$_5$ | H |
| I.a.1072 | CF$_3$ | Cl | H | H | F | C$_2$H$_5$ | C$_2$H$_5$ | H |
| I.a.1073 | F | F | I | F | F | C$_2$H$_5$ | C$_2$H$_5$ | H |
| I.a.1074 | F | H | H | H | F | C$_2$H$_5$ | C$_2$H$_5$ | CH$_3$ |
| I.a.1075 | Cl | H | H | H | F | C$_2$H$_5$ | C$_2$H$_5$ | CH$_3$ |
| I.a.1076 | Br | H | H | H | F | C$_2$H$_5$ | C$_2$H$_5$ | CH$_3$ |
| I.a.1077 | CN | H | H | H | F | C$_2$H$_5$ | C$_2$H$_5$ | CH$_3$ |
| I.a.1078 | CH$_3$ | H | H | H | F | C$_2$H$_5$ | C$_2$H$_5$ | CH$_3$ |
| I.a.1079 | F | H | H | F | F | C$_2$H$_5$ | C$_2$H$_5$ | CH$_3$ |
| I.a.1080 | Cl | H | H | F | F | C$_2$H$_5$ | C$_2$H$_5$ | CH$_3$ |
| I.a.1081 | F | H | H | Cl | F | C$_2$H$_5$ | C$_2$H$_5$ | CH$_3$ |
| I.a.1082 | Cl | H | H | F | F | C$_2$H$_5$ | C$_2$H$_5$ | CH$_3$ |
| I.a.1083 | CN | H | H | F | F | C$_2$H$_5$ | C$_2$H$_5$ | CH$_3$ |
| I.a.1084 | F | H | H | CN | F | C$_2$H$_5$ | C$_2$H$_5$ | CH$_3$ |
| I.a.1085 | CN | H | H | F | F | C$_2$H$_5$ | C$_2$H$_5$ | CH$_3$ |
| I.a.1086 | F | H | F | H | F | C$_2$H$_5$ | C$_2$H$_5$ | CH$_3$ |
| I.a.1087 | Cl | H | F | H | F | C$_2$H$_5$ | C$_2$H$_5$ | CH$_3$ |
| I.a.1088 | CN | H | F | H | F | C$_2$H$_5$ | C$_2$H$_5$ | CH$_3$ |
| I.a.1089 | F | F | F | H | F | C$_2$H$_5$ | C$_2$H$_5$ | CH$_3$ |
| I.a.1090 | Cl | F | F | H | F | C$_2$H$_5$ | C$_2$H$_5$ | CH$_3$ |
| I.a.1091 | F | Cl | F | H | F | C$_2$H$_5$ | C$_2$H$_5$ | CH$_3$ |
| I.a.1092 | Cl | F | F | H | F | C$_2$H$_5$ | C$_2$H$_5$ | CH$_3$ |
| I.a.1093 | CN | F | F | H | F | C$_2$H$_5$ | C$_2$H$_5$ | CH$_3$ |
| I.a.1094 | F | CN | F | H | F | C$_2$H$_5$ | C$_2$H$_5$ | CH$_3$ |
| I.a.1095 | CN | F | F | H | F | C$_2$H$_5$ | C$_2$H$_5$ | CH$_3$ |
| I.a.1096 | F | F | H | F | F | C$_2$H$_5$ | C$_2$H$_5$ | CH$_3$ |
| I.a.1097 | Cl | F | H | F | F | C$_2$H$_5$ | C$_2$H$_5$ | CH$_3$ |
| I.a.1098 | F | Cl | H | F | F | C$_2$H$_5$ | C$_2$H$_5$ | CH$_3$ |
| I.a.1099 | CN | F | H | F | F | C$_2$H$_5$ | C$_2$H$_5$ | CH$_3$ |
| I.a.1100 | F | CN | H | F | F | C$_2$H$_5$ | C$_2$H$_5$ | CH$_3$ |
| I.a.1101 | F | F | F | F | F | C$_2$H$_5$ | C$_2$H$_5$ | CH$_3$ |
| I.a.1102 | Cl | F | F | F | F | C$_2$H$_5$ | C$_2$H$_5$ | CH$_3$ |
| I.a.1103 | F | Cl | F | F | F | C$_2$H$_5$ | C$_2$H$_5$ | CH$_3$ |
| I.a.1104 | CN | F | F | F | F | C$_2$H$_5$ | C$_2$H$_5$ | CH$_3$ |
| I.a.1105 | F | CN | F | F | F | C$_2$H$_5$ | C$_2$H$_5$ | CH$_3$ |
| I.a.1106 | H | F | F | F | F | C$_2$H$_5$ | C$_2$H$_5$ | CH$_3$ |
| I.a.1107 | F | F | Br | F | F | C$_2$H$_5$ | C$_2$H$_5$ | CH$_3$ |
| I.a.1108 | F | F | C≡CH | F | F | C$_2$H$_5$ | C$_2$H$_5$ | CH$_3$ |
| I.a.1109 | CF$_3$ | Cl | H | H | F | C$_2$H$_5$ | C$_2$H$_5$ | CH$_3$ |
| I.a.1110 | F | F | I | F | F | C$_2$H$_5$ | C$_2$H$_5$ | CH$_3$ |
| I.a.1111 | F | H | H | H | F | C$_2$H$_5$ | CH$_3$ | CH$_3$ |
| I.a.1112 | Cl | H | H | H | F | C$_2$H$_5$ | CH$_3$ | CH$_3$ |
| I.a.1113 | Br | H | H | H | F | C$_2$H$_5$ | CH$_3$ | CH$_3$ |
| I.a.1114 | CN | H | H | H | F | C$_2$H$_5$ | CH$_3$ | CH$_3$ |
| I.a.1115 | CH$_3$ | H | H | H | F | C$_2$H$_5$ | CH$_3$ | CH$_3$ |
| I.a.1116 | F | H | H | F | F | C$_2$H$_5$ | CH$_3$ | CH$_3$ |
| I.a.1117 | Cl | H | H | F | F | C$_2$H$_5$ | CH$_3$ | CH$_3$ |
| I.a.1118 | F | H | H | Cl | F | C$_2$H$_5$ | CH$_3$ | CH$_3$ |
| I.a.1119 | Cl | H | H | F | F | C$_2$H$_5$ | CH$_3$ | CH$_3$ |
| I.a.1120 | CN | H | H | F | F | C$_2$H$_5$ | CH$_3$ | CH$_3$ |
| I.a.1121 | F | H | H | CN | F | C$_2$H$_5$ | CH$_3$ | CH$_3$ |
| I.a.1122 | CN | H | H | F | F | C$_2$H$_5$ | CH$_3$ | CH$_3$ |
| I.a.1123 | F | H | F | H | F | C$_2$H$_5$ | CH$_3$ | CH$_3$ |
| I.a.1124 | Cl | H | F | H | F | C$_2$H$_5$ | CH$_3$ | CH$_3$ |
| I.a.1125 | CN | H | F | H | F | C$_2$H$_5$ | CH$_3$ | CH$_3$ |
| I.a.1126 | F | F | F | H | F | C$_2$H$_5$ | CH$_3$ | CH$_3$ |
| I.a.1127 | Cl | F | F | H | F | C$_2$H$_5$ | CH$_3$ | CH$_3$ |
| I.a.1128 | F | Cl | F | H | F | C$_2$H$_5$ | CH$_3$ | CH$_3$ |
| I.a.1129 | Cl | F | F | H | F | C$_2$H$_5$ | CH$_3$ | CH$_3$ |
| I.a.1130 | CN | F | F | H | F | C$_2$H$_5$ | CH$_3$ | CH$_3$ |
| I.a.1131 | F | CN | F | H | F | C$_2$H$_5$ | CH$_3$ | CH$_3$ |
| I.a.1132 | CN | F | F | H | F | C$_2$H$_5$ | CH$_3$ | CH$_3$ |
| I.a.1133 | F | F | H | F | F | C$_2$H$_5$ | CH$_3$ | CH$_3$ |
| I.a.1134 | Cl | F | H | F | F | C$_2$H$_5$ | CH$_3$ | CH$_3$ |
| I.a.1135 | F | Cl | H | F | F | C$_2$H$_5$ | CH$_3$ | CH$_3$ |
| I.a.1136 | CN | F | H | F | F | C$_2$H$_5$ | CH$_3$ | CH$_3$ |
| I.a.1137 | F | CN | H | F | F | C$_2$H$_5$ | CH$_3$ | CH$_3$ |
| I.a.1138 | F | F | F | F | F | C$_2$H$_5$ | CH$_3$ | CH$_3$ |
| I.a.1139 | Cl | F | F | F | F | C$_2$H$_5$ | CH$_3$ | CH$_3$ |
| I.a.1140 | F | Cl | F | F | F | C$_2$H$_5$ | CH$_3$ | CH$_3$ |
| I.a.1141 | CN | F | F | F | F | C$_2$H$_5$ | CH$_3$ | CH$_3$ |
| I.a.1142 | F | CN | F | F | F | C$_2$H$_5$ | CH$_3$ | CH$_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1143 | H | F | F | F | F | $C_2H_5$ | $CH_3$ | $CH_3$ |
| I.a.1144 | F | F | Br | F | F | $C_2H_5$ | $CH_3$ | $CH_3$ |
| I.a.1145 | F | F | C≡CH | F | F | $C_2H_5$ | $CH_3$ | $CH_3$ |
| I.a.1146 | $CF_3$ | Cl | H | H | F | $C_2H_5$ | $CH_3$ | $CH_3$ |
| I.a.1147 | F | F | I | F | F | $C_2H_5$ | $CH_3$ | $CH_3$ |
| I.a.1148 | F | H | H | H | F | Cl | $CH_3$ | H |
| I.a.1149 | Cl | H | H | H | F | Cl | $CH_3$ | H |
| I.a.1150 | Br | H | H | H | F | Cl | $CH_3$ | H |
| I.a.1151 | CN | H | H | H | F | Cl | $CH_3$ | H |
| I.a.1152 | $CH_3$ | H | H | H | F | Cl | $CH_3$ | H |
| I.a.1153 | F | H | H | F | F | Cl | $CH_3$ | H |
| I.a.1154 | Cl | H | H | F | F | Cl | $CH_3$ | H |
| I.a.1155 | F | H | H | Cl | F | Cl | $CH_3$ | H |
| I.a.1156 | Cl | H | H | F | F | Cl | $CH_3$ | H |
| I.a.1157 | CN | H | H | F | F | Cl | $CH_3$ | H |
| I.a.1158 | F | H | H | CN | F | Cl | $CH_3$ | H |
| I.a.1159 | CN | H | H | F | F | Cl | $CH_3$ | H |
| I.a.1160 | F | H | F | H | F | Cl | $CH_3$ | H |
| I.a.1161 | Cl | H | F | H | F | Cl | $CH_3$ | H |
| I.a.1162 | CN | H | F | H | F | Cl | $CH_3$ | H |
| I.a.1163 | F | F | F | H | F | Cl | $CH_3$ | H |
| I.a.1164 | Cl | F | F | H | F | Cl | $CH_3$ | H |
| I.a.1165 | F | Cl | F | H | F | Cl | $CH_3$ | H |
| I.a.1166 | Cl | F | F | H | F | Cl | $CH_3$ | H |
| I.a.1167 | CN | F | F | H | F | Cl | $CH_3$ | H |
| I.a.1168 | F | CN | F | H | F | Cl | $CH_3$ | H |
| I.a.1169 | CN | F | F | H | F | Cl | $CH_3$ | H |
| I.a.1170 | F | F | H | F | F | Cl | $CH_3$ | H |
| I.a.1171 | Cl | F | H | F | F | Cl | $CH_3$ | H |
| I.a.1172 | F | Cl | H | F | F | Cl | $CH_3$ | H |
| I.a.1173 | CN | F | H | F | F | Cl | $CH_3$ | H |
| I.a.1174 | F | CN | H | F | F | Cl | $CH_3$ | H |
| I.a.1175 | F | F | F | F | F | Cl | $CH_3$ | H |
| I.a.1176 | Cl | F | F | F | F | Cl | $CH_3$ | H |
| I.a.1177 | F | Cl | F | F | F | Cl | $CH_3$ | H |
| I.a.1178 | CN | F | F | F | F | Cl | $CH_3$ | H |
| I.a.1179 | F | CN | F | F | F | Cl | $CH_3$ | H |
| I.a.1180 | H | F | F | F | F | Cl | $CH_3$ | H |
| I.a.1181 | F | F | Br | F | F | Cl | $CH_3$ | H |
| I.a.1182 | F | F | C≡CH | F | F | Cl | $CH_3$ | H |
| I.a.1183 | $CF_3$ | Cl | H | H | F | Cl | $CH_3$ | H |
| I.a.1184 | F | F | I | F | F | Cl | $CH_3$ | H |
| I.a.1185 | F | H | H | H | F | $CH_2Cl$ | Cl | $CH_3$ |
| I.a.1186 | Cl | H | H | H | F | $CH_2Cl$ | Cl | $CH_3$ |
| I.a.1187 | Br | H | H | H | F | $CH_2Cl$ | Cl | $CH_3$ |
| I.a.1188 | CN | H | H | H | F | $CH_2Cl$ | Cl | $CH_3$ |
| I.a.1189 | $CH_3$ | H | H | H | F | $CH_2Cl$ | Cl | $CH_3$ |
| I.a.1190 | F | H | H | F | F | $CH_2Cl$ | Cl | $CH_3$ |
| I.a.1191 | Cl | H | H | F | F | $CH_2Cl$ | Cl | $CH_3$ |
| I.a.1192 | F | H | H | Cl | F | $CH_2Cl$ | Cl | $CH_3$ |
| I.a.1193 | Cl | H | H | F | F | $CH_2Cl$ | Cl | $CH_3$ |
| I.a.1194 | CN | H | H | F | F | $CH_2Cl$ | Cl | $CH_3$ |
| I.a.1195 | F | H | H | CN | F | $CH_2Cl$ | Cl | $CH_3$ |
| I.a.1196 | CN | H | H | F | F | $CH_2Cl$ | Cl | $CH_3$ |
| I.a.1197 | F | H | F | H | F | $CH_2Cl$ | Cl | $CH_3$ |
| I.a.1198 | Cl | H | F | H | F | $CH_2Cl$ | Cl | $CH_3$ |
| I.a.1199 | CN | H | F | H | F | $CH_2Cl$ | Cl | $CH_3$ |
| I.a.1200 | F | F | F | H | F | $CH_2Cl$ | Cl | $CH_3$ |
| I.a.1201 | Cl | F | F | H | F | $CH_2Cl$ | Cl | $CH_3$ |
| I.a.1202 | F | Cl | F | H | F | $CH_2Cl$ | Cl | $CH_3$ |
| I.a.1203 | Cl | F | F | H | F | $CH_2Cl$ | Cl | $CH_3$ |
| I.a.1204 | CN | F | F | H | F | $CH_2Cl$ | Cl | $CH_3$ |
| I.a.1205 | F | CN | F | H | F | $CH_2Cl$ | Cl | $CH_3$ |
| I.a.1206 | CN | F | F | H | F | $CH_2Cl$ | Cl | $CH_3$ |
| I.a.1207 | F | F | H | F | F | $CH_2Cl$ | Cl | $CH_3$ |
| I.a.1208 | Cl | F | H | F | F | $CH_2Cl$ | Cl | $CH_3$ |
| I.a.1209 | F | Cl | H | F | F | $CH_2Cl$ | Cl | $CH_3$ |
| I.a.1210 | CN | F | H | F | F | $CH_2Cl$ | Cl | $CH_3$ |
| I.a.1211 | F | CN | H | F | F | $CH_2Cl$ | Cl | $CH_3$ |
| I.a.1212 | F | F | F | F | F | $CH_2Cl$ | Cl | $CH_3$ |
| I.a.1213 | Cl | F | F | F | F | $CH_2Cl$ | Cl | $CH_3$ |
| I.a.1214 | F | Cl | F | F | F | $CH_2Cl$ | Cl | $CH_3$ |
| I.a.1215 | CN | F | F | F | F | $CH_2Cl$ | Cl | $CH_3$ |
| I.a.1216 | F | CN | F | F | F | $CH_2Cl$ | Cl | $CH_3$ |
| I.a.1217 | H | F | F | F | F | $CH_2Cl$ | Cl | $CH_3$ |
| I.a.1218 | F | F | Br | F | F | $CH_2Cl$ | Cl | $CH_3$ |
| I.a.1219 | F | F | C≡CH | F | F | $CH_2Cl$ | Cl | $CH_3$ |
| I.a.1220 | $CF_3$ | Cl | H | H | F | $CH_2Cl$ | Cl | $CH_3$ |
| I.a.1221 | F | F | I | F | F | $CH_2Cl$ | Cl | $CH_3$ |
| I.a.1222 | F | H | H | H | F | CN | $CH_3$ | $CH_3$ |
| I.a.1223 | Cl | H | H | H | F | CN | $CH_3$ | $CH_3$ |
| I.a.1224 | Br | H | H | H | F | CN | $CH_3$ | $CH_3$ |
| I.a.1225 | CN | H | H | H | F | CN | $CH_3$ | $CH_3$ |
| I.a.1226 | $CH_3$ | H | H | H | F | CN | $CH_3$ | $CH_3$ |
| I.a.1227 | F | H | H | F | F | CN | $CH_3$ | $CH_3$ |
| I.a.1228 | Cl | H | H | F | F | CN | $CH_3$ | $CH_3$ |
| I.a.1229 | F | H | H | Cl | F | CN | $CH_3$ | $CH_3$ |
| I.a.1230 | Cl | H | H | F | F | CN | $CH_3$ | $CH_3$ |
| I.a.1231 | CN | H | H | F | F | CN | $CH_3$ | $CH_3$ |
| I.a.1232 | F | H | H | CN | F | CN | $CH_3$ | $CH_3$ |
| I.a.1233 | CN | H | H | F | F | CN | $CH_3$ | $CH_3$ |
| I.a.1234 | F | H | F | H | F | CN | $CH_3$ | $CH_3$ |
| I.a.1235 | Cl | H | F | H | F | CN | $CH_3$ | $CH_3$ |
| I.a.1236 | CN | H | F | H | F | CN | $CH_3$ | $CH_3$ |
| I.a.1237 | F | F | F | H | F | CN | $CH_3$ | $CH_3$ |
| I.a.1238 | Cl | F | F | H | F | CN | $CH_3$ | $CH_3$ |
| I.a.1239 | F | Cl | F | H | F | CN | $CH_3$ | $CH_3$ |
| I.a.1240 | Cl | F | F | H | F | CN | $CH_3$ | $CH_3$ |
| I.a.1241 | CN | F | F | H | F | CN | $CH_3$ | $CH_3$ |
| I.a.1242 | F | CN | F | H | F | CN | $CH_3$ | $CH_3$ |
| I.a.1243 | CN | F | F | H | F | CN | $CH_3$ | $CH_3$ |
| I.a.1244 | F | F | H | F | F | CN | $CH_3$ | $CH_3$ |
| I.a.1245 | Cl | F | H | F | F | CN | $CH_3$ | $CH_3$ |
| I.a.1246 | F | Cl | H | F | F | CN | $CH_3$ | $CH_3$ |
| I.a.1247 | CN | F | H | F | F | CN | $CH_3$ | $CH_3$ |
| I.a.1248 | F | CN | H | F | F | CN | $CH_3$ | $CH_3$ |
| I.a.1249 | F | F | F | F | F | CN | $CH_3$ | $CH_3$ |
| I.a.1250 | Cl | F | F | F | F | CN | $CH_3$ | $CH_3$ |
| I.a.1251 | F | Cl | F | F | F | CN | $CH_3$ | $CH_3$ |
| I.a.1252 | CN | F | F | F | F | CN | $CH_3$ | $CH_3$ |
| I.a.1253 | F | CN | F | F | F | CN | $CH_3$ | $CH_3$ |
| I.a.1254 | H | F | F | F | F | CN | $CH_3$ | $CH_3$ |
| I.a.1255 | F | F | Br | F | F | CN | $CH_3$ | $CH_3$ |
| I.a.1256 | F | F | C≡CH | F | F | CN | $CH_3$ | $CH_3$ |
| I.a.1257 | $CF_3$ | Cl | H | H | F | CN | $CH_3$ | $CH_3$ |
| I.a.1258 | F | F | I | F | F | CN | $CH_3$ | $CH_3$ |
| I.a.1259 | F | H | H | H | F | $OCH_3$ | H | H |
| I.a.1260 | Cl | H | H | H | F | $OCH_3$ | H | H |
| I.a.1261 | Br | H | H | H | F | $OCH_3$ | H | H |
| I.a.1262 | CN | H | H | H | F | $OCH_3$ | H | H |
| I.a.1263 | $CH_3$ | H | H | H | F | $OCH_3$ | H | H |
| I.a.1264 | F | H | H | F | F | $OCH_3$ | H | H |
| I.a.1265 | Cl | H | H | F | F | $OCH_3$ | H | H |
| I.a.1266 | F | H | H | Cl | F | $OCH_3$ | H | H |
| I.a.1267 | Cl | H | H | F | F | $OCH_3$ | H | H |
| I.a.1268 | CN | H | H | F | F | $OCH_3$ | H | H |
| I.a.1269 | F | H | H | CN | F | $OCH_3$ | H | H |
| I.a.1270 | CN | H | H | F | F | $OCH_3$ | H | H |
| I.a.1271 | F | H | F | H | F | $OCH_3$ | H | H |
| I.a.1272 | Cl | H | F | H | F | $OCH_3$ | H | H |
| I.a.1273 | CN | H | F | H | F | $OCH_3$ | H | H |
| I.a.1274 | F | F | F | H | F | $OCH_3$ | H | H |
| I.a.1275 | Cl | F | F | H | F | $OCH_3$ | H | H |
| I.a.1276 | F | Cl | F | H | F | $OCH_3$ | H | H |
| I.a.1277 | Cl | F | F | H | F | $OCH_3$ | H | H |
| I.a.1278 | CN | F | F | H | F | $OCH_3$ | H | H |
| I.a.1279 | F | CN | F | H | F | $OCH_3$ | H | H |
| I.a.1280 | CN | F | F | H | F | $OCH_3$ | H | H |
| I.a.1281 | F | F | H | F | F | $OCH_3$ | H | H |
| I.a.1282 | Cl | F | H | F | F | $OCH_3$ | H | H |
| I.a.1283 | F | Cl | H | F | F | $OCH_3$ | H | H |
| I.a.1284 | CN | F | H | F | F | $OCH_3$ | H | H |
| I.a.1285 | F | CN | H | F | F | $OCH_3$ | H | H |
| I.a.1286 | F | F | F | F | F | $OCH_3$ | H | H |
| I.a.1287 | Cl | F | F | F | F | $OCH_3$ | H | H |
| I.a.1288 | F | Cl | F | F | F | $OCH_3$ | H | H |
| I.a.1289 | CN | F | F | F | F | $OCH_3$ | H | H |
| I.a.1290 | F | CN | F | F | F | $OCH_3$ | H | H |
| I.a.1291 | H | F | F | F | F | $OCH_3$ | H | H |
| I.a.1292 | F | F | Br | F | F | $OCH_3$ | H | H |
| I.a.1293 | F | F | C≡CH | F | F | $OCH_3$ | H | H |
| I.a.1294 | $CF_3$ | Cl | H | H | F | $OCH_3$ | H | H |
| I.a.1295 | F | F | I | F | F | $OCH_3$ | H | H |
| I.a.1296 | F | H | H | H | F | $OCH_3$ | $CH_3$ | H |
| I.a.1297 | Cl | H | H | H | F | $OCH_3$ | $CH_3$ | H |
| I.a.1298 | Br | H | H | H | F | $OCH_3$ | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1299 | CN | H | H | H | F | $OCH_3$ | $CH_3$ | H |
| I.a.1300 | $CH_3$ | H | H | H | F | $OCH_3$ | $CH_3$ | H |
| I.a.1301 | F | H | H | F | F | $OCH_3$ | $CH_3$ | H |
| I.a.1302 | Cl | H | H | F | F | $OCH_3$ | $CH_3$ | H |
| I.a.1303 | F | H | H | Cl | F | $OCH_3$ | $CH_3$ | H |
| I.a.1304 | Cl | H | H | F | F | $OCH_3$ | $CH_3$ | H |
| I.a.1305 | CN | H | H | F | F | $OCH_3$ | $CH_3$ | H |
| I.a.1306 | F | H | H | CN | F | $OCH_3$ | $CH_3$ | H |
| I.a.1307 | CN | H | H | F | F | $OCH_3$ | $CH_3$ | H |
| I.a.1308 | F | H | F | H | F | $OCH_3$ | $CH_3$ | H |
| I.a.1309 | Cl | H | F | H | F | $OCH_3$ | $CH_3$ | H |
| I.a.1310 | CN | H | F | H | F | $OCH_3$ | $CH_3$ | H |
| I.a.1311 | F | F | F | H | F | $OCH_3$ | $CH_3$ | H |
| I.a.1312 | Cl | F | F | H | F | $OCH_3$ | $CH_3$ | H |
| I.a.1313 | F | Cl | F | H | F | $OCH_3$ | $CH_3$ | H |
| I.a.1314 | Cl | F | F | H | F | $OCH_3$ | $CH_3$ | H |
| I.a.1315 | CN | F | F | H | F | $OCH_3$ | $CH_3$ | H |
| I.a.1316 | F | CN | F | H | F | $OCH_3$ | $CH_3$ | H |
| I.a.1317 | CN | F | F | H | F | $OCH_3$ | $CH_3$ | H |
| I.a.1318 | F | F | H | F | F | $OCH_3$ | $CH_3$ | H |
| I.a.1319 | Cl | F | H | F | F | $OCH_3$ | $CH_3$ | H |
| I.a.1320 | F | Cl | H | F | F | $OCH_3$ | $CH_3$ | H |
| I.a.1321 | CN | F | H | F | F | $OCH_3$ | $CH_3$ | H |
| I.a.1322 | F | CN | H | F | F | $OCH_3$ | $CH_3$ | H |
| I.a.1323 | F | F | F | F | F | $OCH_3$ | $CH_3$ | H |
| I.a.1324 | Cl | F | F | F | F | $OCH_3$ | $CH_3$ | H |
| I.a.1325 | F | Cl | F | F | F | $OCH_3$ | $CH_3$ | H |
| I.a.1326 | CN | F | F | F | F | $OCH_3$ | $CH_3$ | H |
| I.a.1327 | F | CN | F | F | F | $OCH_3$ | $CH_3$ | H |
| I.a.1328 | H | F | F | F | F | $OCH_3$ | $CH_3$ | H |
| I.a.1329 | F | F | Br | F | F | $OCH_3$ | $CH_3$ | H |
| I.a.1330 | F | F | C≡CH | F | F | $OCH_3$ | $CH_3$ | H |
| I.a.1331 | $CF_3$ | Cl | H | H | F | $OCH_3$ | $CH_3$ | H |
| I.a.1332 | F | F | I | F | F | $OCH_3$ | $CH_3$ | H |
| I.a.1333 | F | H | H | H | F | $OCH_3$ | $CH_3$ | $CH_3$ |
| I.a.1334 | Cl | H | H | H | F | $OCH_3$ | $CH_3$ | $CH_3$ |
| I.a.1335 | Br | H | H | H | F | $OCH_3$ | $CH_3$ | $CH_3$ |
| I.a.1336 | CN | H | H | H | F | $OCH_3$ | $CH_3$ | $CH_3$ |
| I.a.1337 | $CH_3$ | H | H | H | F | $OCH_3$ | $CH_3$ | $CH_3$ |
| I.a.1338 | F | H | H | F | F | $OCH_3$ | $CH_3$ | $CH_3$ |
| I.a.1339 | Cl | H | H | F | F | $OCH_3$ | $CH_3$ | $CH_3$ |
| I.a.1340 | F | H | H | Cl | F | $OCH_3$ | $CH_3$ | $CH_3$ |
| I.a.1341 | Cl | H | H | F | F | $OCH_3$ | $CH_3$ | $CH_3$ |
| I.a.1342 | CN | H | H | F | F | $OCH_3$ | $CH_3$ | $CH_3$ |
| I.a.1343 | F | H | H | CN | F | $OCH_3$ | $CH_3$ | $CH_3$ |
| I.a.1344 | CN | H | H | F | F | $OCH_3$ | $CH_3$ | $CH_3$ |
| I.a.1345 | F | H | F | H | F | $OCH_3$ | $CH_3$ | $CH_3$ |
| I.a.1346 | Cl | H | F | H | F | $OCH_3$ | $CH_3$ | $CH_3$ |
| I.a.1347 | CN | H | F | H | F | $OCH_3$ | $CH_3$ | $CH_3$ |
| I.a.1348 | F | F | F | H | F | $OCH_3$ | $CH_3$ | $CH_3$ |
| I.a.1349 | Cl | F | F | H | F | $OCH_3$ | $CH_3$ | $CH_3$ |
| I.a.1350 | F | Cl | F | H | F | $OCH_3$ | $CH_3$ | $CH_3$ |
| I.a.1351 | Cl | F | F | H | F | $OCH_3$ | $CH_3$ | $CH_3$ |
| I.a.1352 | CN | F | F | H | F | $OCH_3$ | $CH_3$ | $CH_3$ |
| I.a.1353 | F | CN | F | H | F | $OCH_3$ | $CH_3$ | $CH_3$ |
| I.a.1354 | CN | F | F | H | F | $OCH_3$ | $CH_3$ | $CH_3$ |
| I.a.1355 | F | F | H | F | F | $OCH_3$ | $CH_3$ | $CH_3$ |
| I.a.1356 | Cl | F | H | F | F | $OCH_3$ | $CH_3$ | $CH_3$ |
| I.a.1357 | F | Cl | H | F | F | $OCH_3$ | $CH_3$ | $CH_3$ |
| I.a.1358 | CN | F | H | F | F | $OCH_3$ | $CH_3$ | $CH_3$ |
| I.a.1359 | F | CN | H | F | F | $OCH_3$ | $CH_3$ | $CH_3$ |
| I.a.1360 | F | F | F | F | F | $OCH_3$ | $CH_3$ | $CH_3$ |
| I.a.1361 | Cl | F | F | F | F | $OCH_3$ | $CH_3$ | $CH_3$ |
| I.a.1362 | F | Cl | F | F | F | $OCH_3$ | $CH_3$ | $CH_3$ |
| I.a.1363 | CN | F | F | F | F | $OCH_3$ | $CH_3$ | $CH_3$ |
| I.a.1364 | F | CN | F | F | F | $OCH_3$ | $CH_3$ | $CH_3$ |
| I.a.1365 | H | F | F | F | F | $OCH_3$ | $CH_3$ | $CH_3$ |
| I.a.1366 | F | F | Br | F | F | $OCH_3$ | $CH_3$ | $CH_3$ |
| I.a.1367 | F | F | C≡CH | F | F | $OCH_3$ | $CH_3$ | $CH_3$ |
| I.a.1368 | $CF_3$ | Cl | H | H | F | $OCH_3$ | $CH_3$ | $CH_3$ |
| I.a.1369 | F | F | I | F | F | $OCH_3$ | $CH_3$ | $CH_3$ |
| I.a.1370 | F | H | H | H | F | H | —O(CH$_2$)$_3$— | |
| I.a.1371 | Cl | H | H | H | F | H | —O(CH$_2$)$_3$— | |
| I.a.1372 | Br | H | H | H | F | H | —O(CH$_2$)$_3$— | |
| I.a.1373 | CN | H | H | H | F | H | —O(CH$_2$)$_3$— | |
| I.a.1374 | $CH_3$ | H | H | H | F | H | —O(CH$_2$)$_3$— | |
| I.a.1375 | F | H | H | F | F | H | —O(CH$_2$)$_3$— | |
| I.a.1376 | Cl | H | H | F | F | H | —O(CH$_2$)$_3$— | |
| I.a.1377 | F | H | H | Cl | F | H | —O(CH$_2$)$_3$— | |
| I.a.1378 | Cl | H | H | F | F | H | —O(CH$_2$)$_3$— | |
| I.a.1379 | CN | H | H | F | F | H | —O(CH$_2$)$_3$— | |
| I.a.1380 | F | H | H | CN | F | H | —O(CH$_2$)$_3$— | |
| I.a.1381 | CN | H | H | F | F | H | —O(CH$_2$)$_3$— | |
| I.a.1382 | F | H | F | H | F | H | —O(CH$_2$)$_3$— | |
| I.a.1383 | Cl | H | F | H | F | H | —O(CH$_2$)$_3$— | |
| I.a.1384 | CN | H | F | H | F | H | —O(CH$_2$)$_3$— | |
| I.a.1385 | F | F | F | H | F | H | —O(CH$_2$)$_3$— | |
| I.a.1386 | Cl | F | F | H | F | H | —O(CH$_2$)$_3$— | |
| I.a.1387 | F | Cl | F | H | F | H | —O(CH$_2$)$_3$— | |
| I.a.1388 | Cl | F | F | H | F | H | —O(CH$_2$)$_3$— | |
| I.a.1389 | CN | F | F | H | F | H | —O(CH$_2$)$_3$— | |
| I.a.1390 | F | CN | F | H | F | H | —O(CH$_2$)$_3$— | |
| I.a.1391 | CN | F | F | H | F | H | —O(CH$_2$)$_3$— | |
| I.a.1392 | F | F | H | F | F | H | —O(CH$_2$)$_3$— | |
| I.a.1393 | Cl | F | H | F | F | H | —O(CH$_2$)$_3$— | |
| I.a.1394 | F | Cl | H | F | F | H | —O(CH$_2$)$_3$— | |
| I.a.1395 | CN | F | H | F | F | H | —O(CH$_2$)$_3$— | |
| I.a.1396 | F | CN | H | F | F | H | —O(CH$_2$)$_3$— | |
| I.a.1397 | F | F | F | F | F | H | —O(CH$_2$)$_3$— | |
| I.a.1398 | Cl | F | F | F | F | H | —O(CH$_2$)$_3$— | |
| I.a.1399 | F | Cl | F | F | F | H | —O(CH$_2$)$_3$— | |
| I.a.1400 | CN | F | F | F | F | H | —O(CH$_2$)$_3$— | |
| I.a.1401 | F | CN | F | F | F | H | —O(CH$_2$)$_3$— | |
| I.a.1402 | H | F | F | F | F | H | —O(CH$_2$)$_3$— | |
| I.a.1403 | F | F | Br | F | F | H | —O(CH$_2$)$_3$— | |
| I.a.1404 | F | F | C≡CH | F | F | H | —O(CH$_2$)$_3$— | |
| I.a.1405 | $CF_3$ | Cl | H | H | F | H | —O(CH$_2$)$_3$— | |
| I.a.1406 | F | F | I | F | F | H | —O(CH$_2$)$_3$— | |

The herbicidal compounds useful for the present invention may further be used in conjunction with additional herbicides to which the crop plant is naturally tolerant or to which has been made tolerant by mutagenesis as described SUPRA, or to which it is resistant via expression of one or more additional transgenes as mentioned supra. The herbicides useful for the present invention are often best applied in conjunction with one or more other herbicides to obtain control of a wider variety of undesirable vegetation. When used in conjunction with other herbicides (hereinafter referred to a compound B), the presently claimed compounds can be formulated with the other herbicide or herbicides, tank mixed with the other herbicide or herbicides, or applied sequentially with the other herbicide or herbicides.

The further herbicidal compound B (component B) is in particular selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyldymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives such as ethers, esters or amides.

Preference is given to those compositions according to the present invention comprising at least one herbicide B selected from herbicides of class b1, b6, b9, b10 and b11.

Examples of herbicides B which can be used in combination with the compounds of formula (I) according to the present invention are:

b1) from the group of the lipid biosynthesis inhibitors: ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-ylcarbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-ylcarbonic acid methyl ester; 4-(4'-Chloro-4-ethyl-2'-fluoro[1,1-biphenyl]-3-yl)-5,6-dihydro-2,2,6,6-tetramethyl-5-oxo-2H-pyran-3-ylcarbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-ylcarbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8),
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluorophenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napropanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

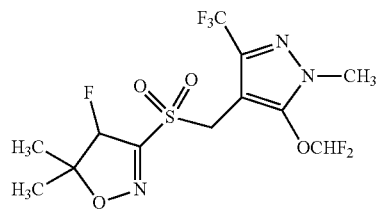

II.1

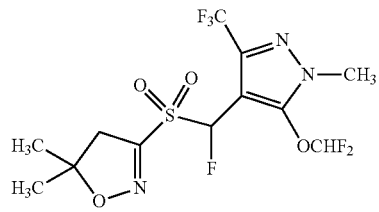

II.2

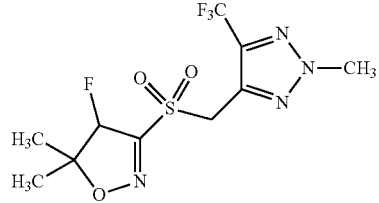

II.3

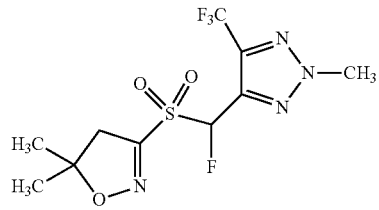

II.4

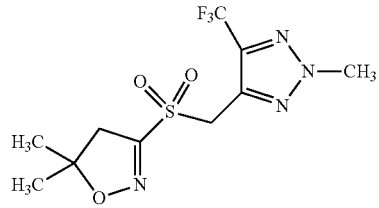

II.5

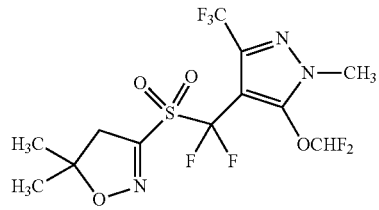

II.6

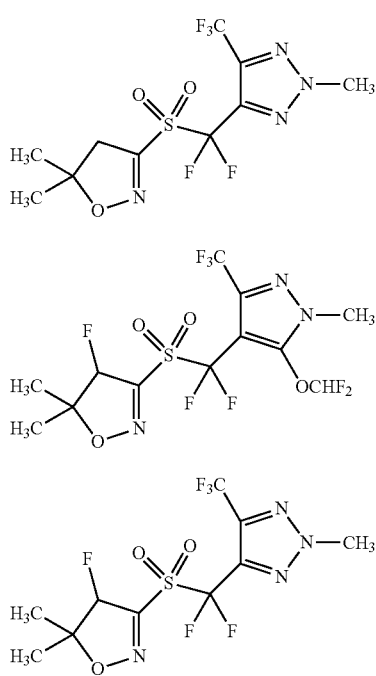

the isoxazoline compounds of the formula (I)I are known in the art, e.g. from WO 2006/024820, WO 2006/037945, WO 2007/071900 and WO 2007/096576;
among the VLCFA inhibitors, preference is given to chloroacetamides and oxyacetamides;

b11) from the group of the cellulose biosynthesis inhibitors:
chlorthiamid, dichlobenil, flupoxam, isoxaben and 1-Cyclohexyl-5-pentafluorphenyloxy-1$^4$-[1,2,4,6]thiatriazin-3-ylamine;

b12) from the group of the decoupler herbicides:
dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agri-culturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dime-thylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammoniurn, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammoniurn, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammoniurn.

A suitable salt of topramezone is for example topramezone-sodium.

Particularly preferred herbicidal compounds B are the herbicides B as defined above; in particular the herbicides B.1-B.189 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | Diuron |
| B.74 | fluometuron |
| B.75 | hexazinone |
| B.76 | isoproturon |
| B.77 | linuron |
| B.78 | metamitron |

TABLE B-continued

| | Herbicide B |
|---|---|
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6) |
| B.95 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazone |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquintrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |
| B.136 | fenoxasulfone |
| B.137 | isoxaben |
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |

TABLE B-continued

| | Herbicide B |
|---|---|
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba-N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quinmerac |
| B.170 | quinmerac-dimethylammonium |
| B.171 | aminocyclopyrachlor |
| B.172 | aminocyclopyrachlor-potassium |
| B.173 | aminocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |

Moreover, it may be useful to apply the compounds of formula (I) in combination with safeners and optionally with one or more further herbicides. Safeners are chemical compounds which prevent or reduce damage on useful plants without having a major impact on the herbicidal action of the compounds of the formula (I) towards unwanted plants. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-

31-4) and N-(2-Methoxybenzoyl)-4-[(methylaminocarbonyl)amino]benzenesulfonamide (CAS 129531-12-0).

Particularly preferred safeners C are the following compounds C.1 to C.17

| C.1 | benoxacor | C.2 | cloquintocet |
|---|---|---|---|
| C.3 | cloquintocet-mexyl | C.4 | cyprosulfamide |
| C.5 | dichlormid | C.6 | fenchlorazole |
| C.7 | fenchlorazole-ethyl | C.8 | fenclorim |
| C.9 | furilazole | C.10 | isoxadifen |
| C.11 | isoxadifen-ethyl | C.12 | mefenpyr |
| C.13 | mefenpyr-diethyl | C.14 | naphtalic acid anhydride |
| C.15 | 4-(dichloroacetyl)-1-oxa-4-azaspiro[4.5]decane | C.16 | 2,2,5-trimethyl-3-(dichloroacetyl)-1,3-oxazolidine |
| C.17 | N-(2-Methoxybenzoyl)-4-[(methylaminocarbonyl)amino]benzenesulfonamide | | |

The active compounds B of groups b1) to b15) and the safener compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

In another embodiment, the present invention refers to a method for identifying a herbicide by using a mutated TriA encoded by a nucleic acid which comprises the nucleotide sequence of SEQ ID NO: 1, or a variant or derivative thereof.

Said method comprises the steps of:
a) generating a transgenic cell or plant comprising a nucleic acid encoding a mutated TriA, wherein the mutated TriA is expressed;
b) applying a herbicide to the transgenic cell or plant of a) and to a control cell or plant of the same variety;
c) determining the growth or the viability of the transgenic cell or plant and the control cell or plant after application of said herbicide, and
d) selecting "herbicides" which confer reduced growth to the control cell or plant as compared to the growth of the transgenic cell or plant.

As described above, the present invention teaches compositions and methods for increasing the tolerance of a crop plant or seed as compared to a wild-type variety of the plant or seed. In a preferred embodiment, the tolerance of a crop plant or seed is increased such that the plant or seed can withstand a herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Post-emergent weed control methods useful in various embodiments hereof utilize about >0.3× application rates of herbicides; in some embodiments, this can be about, for example, >0.3×, >0.4×, >0.5×, >0.6×, >0.7×, >0.8×, >0.9×, or >1× of herbicides. In one embodiment, herbicide-tolerant plants of the present invention have tolerance to a post-emergant application of a herbicides at an amount of about 25 to about 200 g ai/ha. In some embodiments, wherein the herbicide-tolerant plant is a dicot (e.g., soy, cotton), the post-emergant application of the herbicides is at an amount of about 50 g ai/ha. In another embodiment, wherein the herbicide-tolerant plant is a monocot (e.g., maize, rice, sorghum), the post-emergant application of the herbicides is at an amount of about 200 g ai/ha. In other embodiments, wherein the herbicide-tolerant plant is a *Brassica* (e.g., canola), the post-emergant application of the herbicides is at an amount of about 25 g ai/ha. In post-emergent weed control methods hereof, in some embodiments, the method can utilize herbicides application rates at about 7 to 10 days post-emergent. In another embodiment, the application rate can exceed 1× herbicides; in some embodiments, the rate can be up to 4× herbicides, though more typically it will be about 2.5× or less, or about 2× or less, or about 1× or less.

Furthermore, the present invention provides methods that involve the use of at least one herbicide, optionally in combination with one or more herbicidal compounds B, and, optionally, a safener C, as described in detail supra.

In these methods, the herbicide can be applied by any method known in the art including, but not limited to, seed treatment, soil treatment, and foliar treatment. Prior to application, the herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to herbicide, a wide variety of formulations can be employed for protecting plants from weeds, so as to enhance plant growth and reduce competition for nutrients. A herbicide can be used by itself for pre-emergence, post-emergence, pre-planting, and at-planting control of weeds in areas surrounding the crop plants described herein, or a herbicide formulation can be used that contains other additives. The herbicide can also be used as a seed treatment. Additives found in a herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates, and liquid concentrates. The herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

As disclosed herein, the TriA nucleic acids of the invention find use in enhancing the herbicide tolerance of plants that comprise in their genomes a gene encoding a herbicide-tolerant wild-type or mutated TriA protein. Such a gene may be an endogenous gene or a transgene, as described above. Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109), 5-enolpyruvylshikimate-3-phosphate synthase (EPSPS), Glyphosate acetyl transferase (GAT), cytochrome P450 monooxygenase, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD), Protoporphyrinogen oxidase (PPO) and dicamba degrading enzymes as disclosed in WO 02/068607, or phenoxyaceticacid- and phenoxypropionicacid-derivative degrading enzymes as disclosed in WO 2008141154 or WO 2005107437. The combinations generated can also include multiple copies of any one of the polynucleotides of interest.

Consequently, Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of a herbicides. In one embodiment, the post-emergent application of the herbicides is about 7 to 10 days following planting of safener-treated seeds. In some embodiments, the safener is cloquintocet, dichlormid, fluxofenim, or combinations thereof.

Methods of controlling weeds or undesired vegetation

In other aspects, the present invention provides a method for controlling weeds at a locus for growth of a plant or plant part thereof, the method comprising: applying a composition comprising a herbicides to the locus.

In some aspects, the present invention provides a method for controlling weeds at a locus for growth of a plant, the method comprising: applying an herbicide composition comprising herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a wildtype or mutated TriA polypeptide encoded by the polynucleotide, the expression of the wildtype or mutated TriA polypeptide conferring to the plant tolerance to herbicides.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a herbicide-tolerant plant of the invention. The method comprises applying an effective amount of a herbicides to the weeds and to the auxinic herbicide-tolerant plant, wherein the plant has increased tolerance to auxinic herbicide when compared to a wild-type plant. In some embodiments, the herbicide-tolerant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

In other aspects, herbicide(s) (e.g., herbicides) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15: 1, pigment blue 80, pigment yellow 1, pigment yellow 13, pigment red 1 12, pigment red 48:2, pigment red 48: 1, pigment red 57: 1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the herbicides as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising herbicides and at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with herbicides or with a formulation comprising the herbicides is carried out by spraying or dusting the seeds before sowing of the plants and before emergence of the plants.

In other embodiments, in the treatment of seeds, the corresponding formulations are applied by treating the seeds with an effective amount of herbicides or a formulation comprising the herbicides.

In other aspects, the present invention provides a method for combating undesired vegetation or controlling weeds comprising contacting the seeds of the herbicide-tolerant plants of the present invention before sowing and/or after pregermination with herbicides. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepiclium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solarium, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of herbicides or a formulation comprising the herbicides.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a herbicides A.I. In some embodiments, the treatment comprises application of an agronomically acceptable composition that does not contain a herbicides A.I., wherein the composition comprises one or more of agronomically-acceptable carriers, diluents, excipients, plant growth regulators, and the like. In other embodiments, the treatment comprises application of an agronomically acceptable composition that does not contain a herbicides A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Bacterial Strains

Chemical competent *Escherichia coli* TOP10 (Life Technologies; US) and BL21(DE3) Gold (Agilent Technologies; Germany) was used a recipient in transformation experiments. Transformation was done as described by Maniatis et al. Molecular Cloning: A Laboratory Manual, Cold Spring Habor Laboratory Press, Cold Spring Habor; N.Y. (1982). *Agrobacterium tumefaciens* was used to introduce the T-DNA region into *Arabidopsis*, corn and soybean.

Bacterial cultures were routinely grown on Luria broth (LB) or at 37° C. on LB mixed with agar (15% w/v). LB was also supplemented with antibiotic kanamycin and/or chloramphenicol where required. Plasmid DNA was prepared using GeneJet Plasmid Miniprep kit (Thermo Scientific, US). TriA and variants of thereof were generated by gene synthesis (Eurofins, Germany). Synthesized genes harboring XhoI and NcoI restriction sites were cloned into pET24d N-HIS vector with kanamycin resistance. Chaperone plasmid pGro7 (chaperones groEL and groES) with chloramphenicol resistance was obtained from TaKaRa (Japan).

Example 2: Gene Synthesis, Restriction Digestion and Cloning

Gene synthesis an appropriate cloning into the pMK-RQ vector was done by Eurofins (Germany). Restriction enzymes were purchased from New England Restriction enzymes were used according to manufactures instructions.

Example 3: Protein Purification

TriA and variants thereof were produced in *E. coli* BL21 (DE3) Gold (Agilent Technologies, Germany). Therefore *E. coli* was transformed with appropriate pET24d N-HIS tag expression vector and chaperone plasmid pGro7 (chaperones groEL and groES). Bacterial strains were grown at 30° C. in 100 mL LB for 20 h and protein expression induced with 0.1 mM IPTG at 25° C. for 20 hs. Cells were harvested by centrifugation at 3000 rpm at 4° C. for 20 min, resuspended in Bug Buster protein extraction reagent (Novagen, Germany) according to manufactures instructions. Lysates were clarified by centrifugation. Samples of bovine serum albumin (5, 10, and 20 g) were loaded onto each gel analyzed by densitometry to provide an internal standard. Protein determinations were verified using Coomassie protein assay dye, according to manufactures instruction (Thermo Scientific; USA). The HIS-tagged enzymes were purified by metal ion affinity chromatography using Ni-IDA 1000 kit (Macherey-Nagel, Germany) following manufactures instructions. Protein purity was accessed by SDS-PAGE using NuPAGE Novex 4-12% Bis-Tris pre-cast gels (Life Technologies; USA) stained with Coomassie Brilliant Blue (Serva, Germany). Protein concentrations were estimated by measuring absorbance at 280 nm using Lambda Bio+ (Perkin Elmer, USA).

Example 4: Enzyme Kinetics

Resting cell suspension containing triA gene were incubated with various azines, melamine and atrazine and the culture filtrate was analyzed by UPLC-HR-MS. Substrates were obtained either from Sigma-Aldrich or synthesized internally. Synthetic standards and enzyme reaction products were analysed by UPLC-HR-MS (Thermo/Dionex UPLC UltiMate3000 coupled to a QExactive high resolution mass spectrometer). A Waters Acquity HSS T3 column (2.1 mm; 100 mm; 1.8 uM) was used with a mobile phase water/acetonitrile (0.1% formic acid) with a flow rate of 0.6 ul $min^{-1}$. Enzymes were used solved 25 mM sodium phosphate buffer (pH 7.2) with substrate concentration in the range of 1 nM to 10 nM at 30° C. Over time, the original azine peak disappeared whereas the formed OH-Metabolite (reaction product) increased. The product was identified by determination of the exact formula and by analysis of the accurate MS-MS fragments. Moreover for some of the formed products authentic standards were co-eluted. Degradation was calculated against the cells harboring the empty vector as control.

Example 5: Directed Evolution of Amidohydrolase

The azines were docked into the active site of the triA model (based on the trzN crystal structure) by superimposing the molecules onto melamine. On this basis, the residues that form the active site and substrate binding pocket were identified. The main regions responsible for coordination of the active-site metal ion; residues known to be essential for the amidohydrolase activity; residues that form the hydrophobic "base" of the active site or are essential for hydrolase activity interactions with the aromatic ring of the substrate, were not changed. However, amino were modified in order to expand the enzyme pocket. The model was used on the one hand to predict amino acids targets away from the active site that may influence the acceptance of triazines in general, on the other hand the model was used to identify space requiring amino acids in the enzyme pocket which could be changed towards smaller amino acids having a similar hydrophobicity to achieve an accommodation of the more bulky azines without altering the enzyme activity.

Example 6: Generation of Herbicide Tolerant Model Plants

Generation of azine-tolerant *Arabidopsis* plants having wildtype or mutated amidohydrolase sequences. For transformation of *Arabidopsis thaliana*, wildtype or amidohydrolase sequences based on SEQ ID NO: 1, encoding SEQ ID NO:2, are cloned with standard cloning techniques as described in Sambrook et al. (Molecular cloning (2001) Cold Spring Harbor Laboratory Press) in a binary vector containing resistance marker gene cassette (AHAS) and mutated amidohydrolase sequence (marked as GOI) in between ubiquitin promoter (PcUbi) and nopaline synthase terminator (NOS) sequence. Binary plasmids are introduced to *Agrobacterium tumefaciens* for plant transformation. *Arabidopsis thaliana* are transformed with wildtype or mutated amidohydrolase sequences by floral dip method as described by McElver and Singh (WO 2008/124495). Transgenic *Arabidopsis* plants are subjected to TaqMan analysis for analysis of the number of integration loci.

Example 7: Test for Herbicide Tolerant Model Plants

For selection of azine resistant *Arabidopsis thaliana* plants, expressing triA and variants thereof, are used. Selected *Arabidopsis thaliana* lines were assayed for improved resistance to azines like 6-cyclopentyl-N4-(2,3,4, 5,6-pentafluorophenyl)-1,3,5-triazine-2,4-diamine in 48-well plates. Therefore, T2-seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v). Four to five seeds per well are plated on solid nutrient medium consisting of half-strength murashige skoog nutrient solution, pH 5.8 (Murashige and Skoog (1962) Physiologia 40 Plantarum 15: 473-497). Compounds are dissolved in dimethylsulfoxid (DMSO) and added to the medium prior to solidification (final DMSO concentration 0.1%). Multi well plates are incubated in a growth chamber at 22° C., 75% relative humidity and 110 μmol Phot*m-2*s-1 with 14: 10 h light: dark photoperiod. Growth inhibition is evaluated seven to ten days after seeding in comparison to wild type plants. Tolerance factors are calculated based on IC50 values of growth inhibition of transformed versus non-transformed *Arabidopsis* plants. Additionally, transgenic T2 or T3 *Arabidopsis* plants are tested for improved tolerance to cellulose biosynthesis-inhibiting herbicides in greenhouse studies.

Example 8: Generation and Test of Herbicide Tolerance Crops

Binary vectors are generated as described in EXAMPLE 9. Soybean cv Jake are transformed as previously described by Siminszky et al., Phytochem Rev. 5:445-458 (2006). After regeneration, transformants are transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events are transplanted to larger pots and allowed to grow in the growth chamber. An optimal shoot for cutting is about 3-4 inches tall, with at least two nodes present. Each cutting is taken from the original transformant (mother plant) and dipped into rooting hormone powder (indole-3-butyric acid, IBA). The cutting is then placed in oasis wedges inside a bio-dome. The mother plant is taken to maturity in the greenhouse and harvested for seed. Wild type cuttings are also taken simultaneously to serve as negative controls. The cuttings are kept in the bio-dome for 5-7 days. 7-10 days after transfer to oasis wedges, the roots are treated via nutrient solution with the herbicide. Typical phytotox symptoms, like club shaped root, are evaluated 3-4 days after treatment. Less or no injury of transgenic plants compared to wildtype plants are interpreted as herbicide tolerance.

Figure 3:
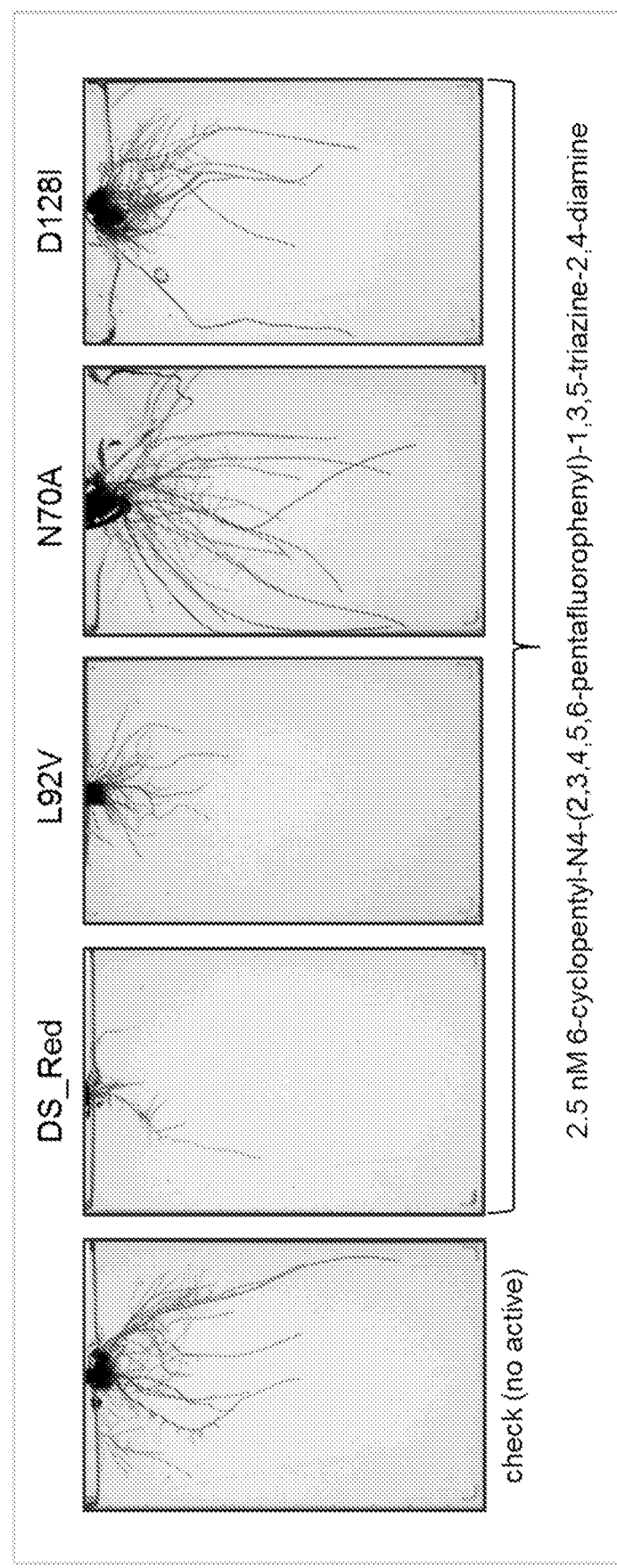
FIG. 3 shows root development of corn transformed with DSred or a triA-variant in the absence or presence of 6-cyclopentyl-N4-(2,3,4,5,6-pentafluorophenyl)-1,3,5-triazine-2,4-diamine.
Figure 4:
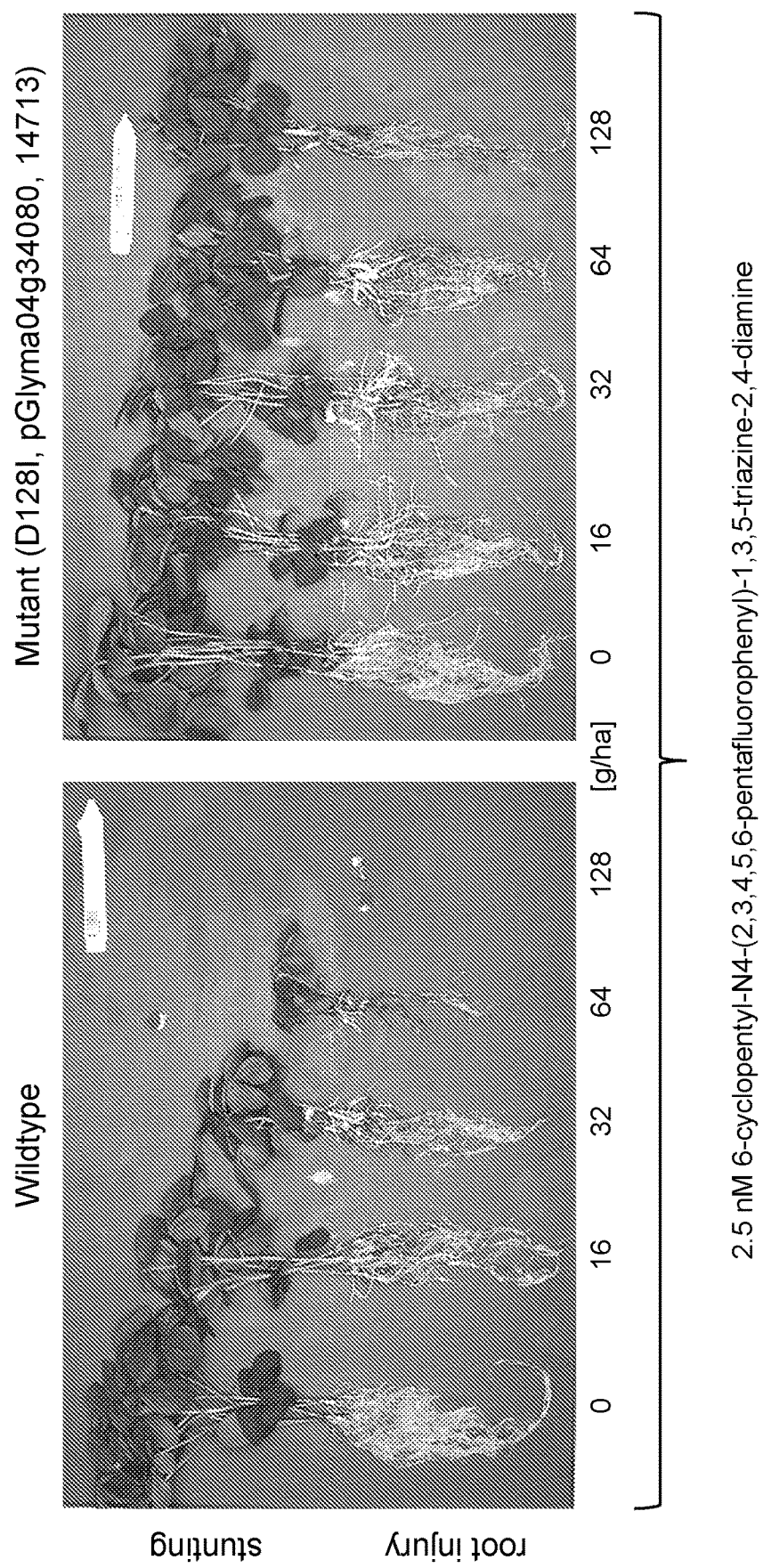
FIG. 4 shows an example for the development of soybean plants transformed mutated form of triA in combination with a root specific promoter and in reference to the wildtype (variety JAKE). The T1 seeds have been germinated and treated under pre-emergence conditions with 6-cyclopentyl-N4-(2,3,4,5,6-pentafluorophenyl)-1,3,5-triazine-2,4-diamine. at the indicated rates

Immature corn embryos were transformed according to the procedure outlined in Peng et al. (WO2006/136596). Plants are tested for the presence of the T-DNA by Taqman analysis with the target being the nos terminator which is present in all constructs. Healthy looking plants are sent to the greenhouse for hardening and subsequent spray testing. The plants are individually transplanted into MetroMix 360 soil in 4" pots. Once in the greenhouse (day/night cycle of 27° C./21° C. with 14 hour day length supported by 600 W high pressure sodium lights), they are allowed to grow for 14 days. Transgenic corn plants are cultivated to T1 seeds for herbicide tolerance testing. 14 days after transfer, the roots are treated via nutrient solution with the herbicide. Typical phytotox symptoms, like club shaped root, are evaluated 3-4 days after treatment. Less or no injury of transgenic plants compared to wildtype plants are interpreted as herbicide tolerance. For post emergence treatment, the test plants are first grown to a height of 3 to 15 cm, depending on the plant habit, and only then treated with the herbicides. For this purpose, the test plants are either sown directly, grown in the same containers or they are first grown separately and transplanted into the test containers a few days prior to treatment. Herbicide injury evaluations are taken at 2 and 3 weeks after treatment. Plant injury is rated on a scale of 0% to 100%, 0% being no injury and 100% being complete death. The results are shown in the following Tables 2, 3 and 4, and in FIGS. 3 and 4

TABLE 2

| Aminoacid exchanged | Root injury [%] |
|---|---|
| N70N | 80 |
| N70A | 0 |
| L92V | 50 |
| Q96M | n.d. |
| D128I | 0 |
| M155V | 10 |
| F157 | 50 |
| N70LQ71I | n.d. |
| N70SQ71L | n.d. |
| L88AL92A | 0 |
| Q71I_L92V_M155V_F157I | n.d. |

TABLE 3

| aminoacid exchange | Event | Tolerancefactor |
|---|---|---|
| N70A | 13359 | ++ |
| N70A | 13684 | ++ |
| N70A | 13713 | ++ |
| N70A | 13901 | ++ |
| N70A | 13920 | ++ |
| N70A | 13932 | ++ |
| N70A | 13996 | − |
| N70A | 13998 | ++ |
| N70A | 14038 | ++ |
| N70A | 14041 | ++ |
| N70A | 14086 | ++ |
| N70A | 14103 | − |
| L92V | 13988 | ++ |
| L92V | 14720 | ++ |
| L92V | 13791 | ++ |
| L92V | 13802 | ++ |
| L92V | 13982 | + |
| L92V | 13571 | + |
| L92V | 13821 | + |
| L92V | 13627 | − |
| Q96M | 14765 | ++ |
| Q96M | 14411 | ++ |
| Q96M | 13947 | ++ |
| Q96M | 14406 | ++ |
| Q96M | 14402 | ++ |
| Q96M | 14408 | + |
| Q96M | 14403 | − |
| D128I | 13737 | + |
| D128I | 13768 | ++ |
| D128I | 13779 | ++ |
| D128I | 13808 | + |
| D128I | 13994 | ++ |
| D128I | 14001 | ++ |
| D128I | 14049 | ++ |
| M155V | 13552 | − |
| M155V | 13745 | ++ |
| M155V | 14029 | ++ |
| M155V | 14033 | ++ |
| M155V | 14080 | ++ |
| M155V | 14478 | ++ |
| M155V | 14826 | ++ |
| N70LQ71I | 14096 | +++ |
| N70LQ71I | 13710 | ++ |
| N70LQ71I | 13906 | ++ |
| N70LQ71I | 13824 | ++ |
| N70LQ71I | 14208 | ++ |
| N70LQ71I | 14181 | ++ |
| N70LQ71I | 14177 | ++ |
| N70LQ71I | 13398 | +++ |
| N70LQ71I | 14153 | ++ |
| N70LQ71I | 14028 | ++ |
| N70LQ71I | 13396 | − |
| N70LQ71I | 14755 | +++ |
| N70SQ71L | 13798 | +++ |
| N70SQ71L | 13733 | +++ |
| N70SQ71L | 14000 | ++ |
| N70SQ71L | 14108 | ++ |
| N70SQ71L | 14045 | ++ |
| N70SQ71L | 13716 | ++ |
| N70SQ71L | 13763 | ++ |
| N70SQ71L | 13577 | ++ |
| L88AL92A | 13636 | ++ |
| L88AL92A | 13807 | ++ |
| L88AL92A | 14149 | ++ |
| L88AL92A | 14645 | ++ |
| L88AL92A | 14760 | + |
| L88AL92A | 13634 | − | excellent 6-8 +++
very good-good 2-6 ++
slight 1-2 +
no tolerance 0 −

TABLE 4

| Aminoacid exchange | Promoter | Event | Tolerancefactor |
|---|---|---|---|
| D128I | p-pcUBI | 13737 | + |
| D128I | p-pcUBI | 13768 | ++ |
| D128I | p-pcUBI | 13779 | ++ |
| D128I | p-pcUBI | 13808 | + |

TABLE 4-continued

| Aminoacid exchange | Promoter | Event | Tolerancefactor |
|---|---|---|---|
| D128I | p-pcUBI | 13994 | ++ |
| D128I | p-pcUBI | 14001 | ++ |
| D128I | p-pcUBI | 14049 | ++ |
| D128I | p-ET11820a | 14657 | +++ |
| D128I | p-ET11820a | 14651 | +++ |
| D128I | p-ET11820a | 14757 | ++ |
| D128I | p-ET11820a | 14656 | ++ |
| D128I | p-ET11820a | 14659 | ++ |
| D128I | p-ET11820a | 14649 | ++ |
| D128I | p-ET11820a | 14631 | ++ |
| D128I | p-Glyma04g34080 | 14630 | ++ |
| D128I | p-Glyma04g34080 | 14640 | ++ |
| D128I | p-Glyma04g34080 | 14653 | ++ |
| D128I | p-Glyma04g34080 | 14655 | ++ |
| D128I | p-Glyma04g34080 | 14673 | ++ |
| D128I | p-Glyma04g34080 | 14713 | +++ |
| D128I | p-Glyma04g34080 | 14717 | ++ |
| D128I | p-Glyma04g34080 | 14719 | ++ |
| D128I | p-Glyma04g34080 | 14725 | ++ |
| D128I | p-Glyma04g34080 | 14650 | ++ |
| M155V | p-pcUBI | 13552 | − |
| M155V | p-pcUBI | 13745 | ++ |
| M155V | p-pcUBI | 14029 | ++ |
| M155V | p-pcUBI | 14033 | ++ |
| M155V | p-pcUBI | 14080 | ++ |
| M155V | p-pcUBI | 14478 | ++ |
| M155V | p-pcUBI | 14826 | ++ |
| M155V | p-ET11820a | 14628 | − |
| M155V | p-ET11820a | 14641 | ++ |
| M155V | p-ET11820a | 14648 | ++ |
| M155V | p-ET11820a | 14652 | ++ |
| M155V | p-ET11820a | 14663 | + |
| M155V | p-ET11820a | 14664 | + |
| M155V | p-ET11820a | 14674 | − |
| M155V | p-ET11820a | 14723 | + |
| M155V | p-ET11820a | 14750 | ++ |
| M155V | p-Glyma04g34080 | 14646 | ++ |
| M155V | p-Glyma04g34080 | 14654 | ++ |
| M155V | p-Glyma04g34080 | 14716 | ++ |
| M155V | p-Glyma04g34080 | 14729 | +++ |
| M155V | p-Glyma04g34080 | 14772 | ++ |

The legend of values of Table 3 applies likewise to Table 4.

Example 9: Binary Vector Construction

Cloning methods e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of E. coli cells and culture of bacteria were performed as described in Sambrook et al. (1989) (Cold Spring Harbor Laboratory Press: ISBN 0-87965-309-6). Polymerase chain reaction was performed using Phusion™ High-Fidelity DNA Polymerase (NEB, Frankfurt, Germany) according to the manufactures instructions. In general, primers used in PCR were designed such, that at least 20 nucleotides of the 3' end of the primer anneal perfectly with the template to amplify. Restriction sites were added by attaching the corresponding nucleotides of the recognition sites to the 5' end of the primer. Fusion PCR, for example described by K. Heckman and L. R. Pease, Nature Protocols (2207) 2, 924-932 was used as an alternative method to join two fragments of interest, e.g. a promoter to a gene or a gene to a terminator. Gene Synthesis, as for example described by Czar et al. (Trends in Biotechnology, 2009, 27(2): 63-72), was performed by Life Technologies using their Geneart® service.

Genes were assessed for codon usage and the presence of restriction sites that might impede cloning efforts. Where necessary genes were codon optimized using standard protocols for maximum expression in the crop plant (for example see Puigbo et al. 2007 and Gasper et al. 2012) as well as removal of undesired restriction sites. Genes were either synthesized by GeneArt (Regensburg) or PCR-amplified using Phusion™ High-Fidelity DNA Polymerase (NEB, Frankfurt, Germany) according to the manufactures instructions from cDNA. In both cases a NcoI and/or AscI restriction site at the 5'terminus, and a Pac I restriction site at the 3' terminus were introduced to enable cloning of these genes between functional elements such as promoters and terminators using these restriction sites. Promoter-terminator modules or promoter-intron-terminator modules were created by complete synthesis by GeneArt (Regensburg) or by joining the corresponding expression elements using fusion PCR and cloning the PCR-product into the TOPO-vector pCR2.1 (Invitrogen) according to the manufactures instructions. While joining terminator sequences to promoter sequences or promoter-intron sequences either via synthesis of whole cassettes or using fusion PCR, recognition sequences for the restriction endonucleases were added to either side of the modules, and the recognition sites for the restriction endonucleases NcoI, AscI and PacI were introduced between promoter and terminator or between introns and terminator. To obtain the final expression modules, PCR-amplified genes were cloned between promoter and terminator or intron and terminator via NcoI and/or Pac I restriction sites.

Alternatively, gene synthesis, as for example described by Czar et al. (Trends in Biotechnology, 2009, 27(2): 63-72), can be performed by Life Technologies using their Geneart® service. Standard methods like cloning, restriction, molecular analysis, transformation of E. coli cells and culture of bacteria can be performed as described in Sambrook et al. (1989) (Cold Spring Harbor Laboratory Press: ISBN 0-87965-309-6). Polymerase chain reaction can be performed using Phusion™ High-Fidelity DNA Polymerase (NEB, Frankfurt, Germany) according to the manufactures instructions. Fusion PCR can be done as described by K. Heckman and L. R. Pease, Nature Protocols (2207) 2, 924-932. In both cases a NcoI and/or AscI restriction site at the 5'terminus, and a PacI restriction site at the 3' terminus can be introduced to enable cloning of these genes between functional elements. Promoter-terminator modules or promoter-intron-terminator modules were created by complete synthesis by GeneArt (Regensburg) or by joining the corresponding expression elements using fusion PCR and cloning the PCR-product into the TOPO-vector pCR2.1 (Invitrogen) according to the manufactures instructions. While joining terminator sequences to promoter sequences or promoter-intron sequences either via synthesis of whole cassettes or using fusion PCR, recognition sequences for the restriction endonucleases can be added to either side of the modules, and the recognition sites for the restriction endonucleases NcoI, AscI and PacI can be introduced between promoter and terminator or between introns and terminator. To obtain the final expression modules, PCR-amplified genes can be cloned between promoter and terminator or intron and terminator via NcoI and/or Pac I restriction sites. Genes of interest can be codon optimized using standard protocols for maximum expression in the crop plant (for example see Puigbo et al. 2007 and Gasper et al. 2012) as well as removal of undesired restriction sites and synthesized by GeneArt (Regensburg, Germany).

REFERENCES

Esser H O, Dupuis G, Ebert E, Marco G J, Vogel C (1975) s-Triazines. In: Kearney P C, Kaufman D J (eds) Herbicides, chemistry, degradation and mode of action. Marcel Dekker, New York, pp 129-208

Seffernick J L, McTavish H, Osborne J P, de Souza M L, Sadowsky M J, Wackett L P (2002) Atrazine chlorohydrolase from *Pseudomonas* sp. strain ADP is a metalloenzyme. Biochemistry 41: 14430-14437

Wackett et al.; Biodegradation of atrazine and related s-triazine compounds: from enzymes to field studies, Applied Microbiology and Biotechnology; 58 (1), 39-45, 2002 de Souza M L, Sadowsky M J, Wackett L P (1996) Atrazine chlorohydrolase from *Pseudomonas* sp strain ADP: Gene sequence, enzyme purification, and protein characterization. Journal of Bacteriology 178: 4894-4900.

Sadowsky et al.; U.S. Pat. No. 6,369,299, Transgenic plants expressing bacterial atrazine degrading gene AtzA Padgette S. R. et al., Site directed mutagenesis of a conserved region of the 5-Enolpyruvylshikimate-3-phosphate synthase actives-site; J. Biol. Chem., 266, 33, 1991

Maniatis et al. Molecular Cloning: A Laboratory Manual, Cold Spring Habor Laboratory Press, Cold Spring Habor; N.Y. (1982)

Gasper P., Oliveira J-L., Frommlet J., Santos M. A. S., Moura G. (2012) EuGene: maximizing synthetic gene design for heterologous expression. Bioinformatics 28(20), 2683-2684.

Murashige and Skoog 1962 Physiologia 40 Plantarum 15: 473-497, Molecular cloning Cold Spring Harbor Laboratory Press (2001)

Komori T., Imayama T., Kato N., Ishida Y., Ueiki J., Komari T. (2007) Current Status of Binary Vectors and Sub-binary Vectors. Plant Physiology 145, 1155-1160.

Puigbo P., Guzman E., Romeu A., Garcia-Valve A. (2007) OPTIMIZER: A Web Server for Optimizing the Codon Usage of DNA Sequences. Nucleic Acids Research 35 web server edition. W126-W131.

Siminszky B., Plant cytochrome P450-mediated herbicide metabolism, Phytochem Rev. 5:445-458, 2006

The invention claimed is:

1. A plant, plant part, or plant cell comprising a polynucleotide encoding a mutant TriA polypeptide having at least 80% identity to the sequence of SEQ ID NO: 2, wherein the amino acid sequence of the mutant TriA polypeptide differs from the wildtype amino acid sequence of a TriA polypeptide at one or more amino acids corresponding to positions 70, 71, 88, 91, 92, 96, 126, 128, 155, 157, 167, 220 of SEQ ID NO: 2, wherein the expression of said polynucleotide confers to the plant, plant part, or plant cell tolerance to herbicides.

2. The plant or plant part of claim 1, wherein the expression of said polynucleotide confers to the plant, plant part, or plant cell tolerance to a compound which inhibits cellulose biosynthesis.

3. The plant, plant part, or plant cell of claim 1, wherein the mutant TriA polypeptide has at least 85% amino acid sequence identity to SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

4. The plant part of claim 1 comprising a seed, wherein the seed is capable of germination into a plant comprising in at least some of its cells a polynucleotide operably linked to a promoter operable in plant cells, the promoter capable of expressing the mutant TriA polypeptide encoded by the polynucleotide, the expression of the mutant TriA polypeptide conferring to the plant tolerance to herbicides.

5. The plant, plant part, or plant cell of claim 1, wherein the polynucleotide is operably linked to a promoter operable in a plant cell.

6. A product prepared from the plant, plant part, or plant cell of claim 1, wherein the product comprises the polynucleotide encoding the mutant TriA polypeptide.

7. The product of claim 6, wherein the product is fodder, seed meal, oil, or seed-treatment-coated seed.

8. The plant, plant part, or plant cell of claim 1, wherein the plant, plant part, or plant cell further comprises a second herbicide-tolerant trait.

9. A method for producing a plant product, the method comprising processing the plant or plant part of claim 1 to obtain the plant product, wherein the plant product comprises the polynucleotide encoding the mutant TriA polypeptide.

10. The method of claim 9, wherein the plant product is fodder, seed meal, oil, or seed-treatment-coated seeds.

11. The plant, plant part, or plant cell of claim 1, wherein the mutant TriA polypeptide has at least 90% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

12. The plant, plant part, or plant cell of claim 1, wherein the mutant TriA polypeptide has at least 95% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

13. A plant, plant part, or plant cell comprising a polynucleotide encoding a mutant TriA polypeptide wherein the mutant TriA polypeptide comprises the sequence of SEQ ID NO: 2, wherein the amino acid sequence differs from the wildtype amino acid sequence at one or more amino acids corresponding to positions 70, 71, 88, 91, 92, 96, 126, 128, 155, 157, 167, 220 of SEQ ID NO: 2.

14. A method for controlling weeds at a locus for growth of a plant, the method comprising: (a) applying an herbicide composition comprising herbicides to the locus; and (b) planting a seed at the locus, wherein the seed comprises a polynucleotide encoding a mutant TriA polypeptide having at least 80% identity to the sequence of SEQ ID NO: 2, wherein the amino acid sequence of the mutant TriA polypeptide differs from the wildtype amino acid sequence of a TriA polypeptide at one or more amino acids corresponding to positions 70, 71, 88, 91, 92, 96, 126, 128, 155, 157, 167, 220 of SEQ ID NO: 2, wherein the seed is capable of producing a plant that comprises in at least some of its cells the polynucleotide operably linked to a promoter operable in plant cells, the promoter capable of expressing the mutant TriA polypeptide encoded by the polynucleotide, the expression of the mutant TriA polypeptide conferring to the plant tolerance to herbicides.

15. The method of claim 14, wherein herbicide composition is applied to the weeds and to the plant produced by the seed.

16. The method according to claim 14, wherein the herbicide comprises a compound which inhibits cellulose biosynthesis.

17. The method of claim 14, wherein the mutant TriA polypeptide has at least 85% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

18. The method of claim 14, wherein the mutant TriA polypeptide has at least 90% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

19. The method of claim 14, wherein the mutant TriA polypeptide has at least 95% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

20. An isolated and/or recombinantly produced and/or synthetic nucleic acid molecule comprising:
a nucleic acid molecule encoding a mutated TriA polypeptide having 80% or more identity with the amino acid sequence of the TriA polypeptide sequence of SEQ ID NO: 2, wherein the amino acid sequence of the mutated TriA polypeptide differs from the wildtype amino acid sequence of a TriA polypeptide at one or more amino acids corresponding to positions 70, 71, 88, 91, 92, 96, 126, 128, 155, 157, 167, 220 of SEQ ID NO: 2, and
wherein expression of the nucleic acid molecule in a plant cell, a plant or a part thereof confers increased herbicide tolerance or resistance thereto, as compared to a corresponding, non-transformed, wild type plant cell, a plant or a part thereof.

21. An expression cassette comprising the nucleic acid molecule as defined in claim 20, and a promoter operable in plant cells.

22. The expression cassette of claim 21, wherein the promoter is a root-specific promoter.

23. A vector comprising the nucleic acid molecule as defined in claim 20.

24. The isolated and/or recombinantly produced and/or synthetic nucleic acid molecule of claim 20, wherein the mutated TriA polypeptide has at least 85% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

25. The isolated and/or recombinantly produced and/or synthetic nucleic acid molecule of claim 20, wherein the mutated TriA polypeptide has at least 90% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

26. The isolated and/or recombinantly produced and/or synthetic nucleic acid molecule of claim 20, wherein the mutated TriA polypeptide has at least 95% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

27. An isolated, recombinant and/or chemically synthesized mutant TriA polypeptide comprising an amino acid sequence having at least 80% identity to the sequence of SEQ ID NO: 2, wherein the amino acid sequence of the mutant TriA polypeptide differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

28. The isolated, recombinant and/or chemically synthesized mutated TriA polypeptide of claim 27, wherein the mutant TriA polypeptide has at least 85% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

29. The isolated, recombinant and/or chemically synthesized mutated TriA polypeptide of claim 27, wherein the mutant TriA polypeptide has at least 90% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

30. The isolated, recombinant and/or chemically synthesized mutated TriA polypeptide of claim 27, wherein the mutant TriA polypeptide has at least 95% identity to the sequence of SEQ ID NO: 2 and differs from the wildtype amino acid sequence of a TriA polypeptide at one or more amino acids corresponding to positions 70, 71, 88, 91, 92, 96, 126, 128, 155, 157, 167, 220 of SEQ ID NO: 2.

* * * * *